(12) United States Patent
Castelli et al.

(10) Patent No.: US 12,109,205 B2
(45) Date of Patent: *Oct. 8, 2024

(54) METHODS OF TREATING FABRY PATIENTS HAVING RENAL IMPAIRMENT

(71) Applicant: Amicus Therapeutics, Inc., Cranbury, NJ (US)

(72) Inventors: Jeff Castelli, New Hope, PA (US); Elfrida Benjamin, Millstone Township, NJ (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 337 days.

This patent is subject to a terminal disclaimer.

(21) Appl. No.: 17/078,840

(22) Filed: Oct. 23, 2020

(65) Prior Publication Data

US 2021/0038583 A1   Feb. 11, 2021

Related U.S. Application Data

(60) Continuation of application No. 16/817,881, filed on Mar. 13, 2020, now Pat. No. 10,857,141, which is a continuation of application No. 16/678,183, filed on Nov. 8, 2019, now Pat. No. 10,874,655, which is a division of application No. 16/284,582, filed on Feb. 25, 2019, now Pat. No. 10,471,053, which is a division of application No. 15/992,336, filed on May 30, 2018, now Pat. No. 10,251,873.

(60) Provisional application No. 62/626,953, filed on Feb. 6, 2018, provisional application No. 62/512,458, filed on May 30, 2017.

(51) Int. Cl.
*A61K 31/445* (2006.01)
*A61P 13/12* (2006.01)
*A61K 9/48* (2006.01)

(52) U.S. Cl.
CPC ............ *A61K 31/445* (2013.01); *A61P 13/12* (2018.01); *A61K 9/48* (2013.01)

(58) Field of Classification Search
CPC .................................................. A61K 31/445
USPC ....................................................... 514/315
See application file for complete search history.

(56) References Cited

U.S. PATENT DOCUMENTS

| | | | |
|---|---|---|---|
| 7,851,143 B2 | 12/2010 | Kaneski et al. |
| 7,973,157 B2 | 7/2011 | Major et al. |
| 8,321,148 B2 | 11/2012 | Lockhart et al. |
| 8,592,362 B2 | 11/2013 | Benjamin et al. |
| 9,000,011 B2 | 4/2015 | Lockhart et al. |
| 9,056,101 B2 | 6/2015 | Lockhart |
| 9,066,939 B2 | 6/2015 | Schiffmann et al. |
| 9,095,584 B2 | 8/2015 | Benjamin et al. |
| 9,206,457 B2 | 12/2015 | Do |
| 9,480,682 B2 | 11/2016 | Lockhart et al. |
| 9,545,397 B2 | 1/2017 | Benjamin et al. |
| 9,694,056 B2 | 7/2017 | Khanna et al. |
| 9,750,732 B2 | 9/2017 | Schiffmann et al. |
| 9,987,263 B2 | 6/2018 | Lockhart et al. |
| 9,999,618 B2 | 6/2018 | Castelli et al. |
| 10,076,514 B2 | 9/2018 | Benjamin |
| 10,155,027 B2 | 12/2018 | Khanna et al. |
| 10,251,873 B2 | 4/2019 | Castelli et al. |
| 10,357,548 B2 | 7/2019 | Khanna |
| 10,383,864 B2 | 8/2019 | Lockhart et al. |
| 10,406,143 B2 | 9/2019 | Lockhart et al. |
| 10,471,053 B2 | 11/2019 | Castelli et al. |
| 10,525,045 B2 | 1/2020 | Castelli et al. |
| 10,537,564 B2 | 6/2020 | Benjamin |
| 10,792,278 B2 | 10/2020 | Castelli et al. |
| 10,792,279 B2 | 10/2020 | Castelli et al. |
| 10,799,491 B2 | 10/2020 | Castelli et al. |
| 10,806,727 B2 | 10/2020 | Castelli et al. |
| 10,813,921 B2 | 10/2020 | Benjamin et al. |
| 10,849,889 B2 | 12/2020 | Castelli et al. |
| 10,849,890 B2 | 12/2020 | Castelli et al. |
| 10,857,141 B2 | 12/2020 | Castelli et al. |
| 10,857,142 B2 | 12/2020 | Castelli et al. |
| 10,874,655 B2 | 12/2020 | Castelli et al. |
| 10,874,656 B2 | 12/2020 | Castelli et al. |
| 10,874,657 B2 | 12/2020 | Castelli et al. |
| 10,925,866 B2 | 2/2021 | Castelli et al. |
| RE48,608 E | 6/2021 | Benjamin et al. |
| 2011/0152319 A1 | 6/2011 | Benjamin et al. |
| 2014/0219986 A1 | 8/2014 | Greene et al. |
| 2017/0051267 A1 | 2/2017 | Calhoun |
| 2018/0153999 A1 | 6/2018 | Greene et al. |
| 2018/0360812 A1 | 12/2018 | Castelli et al. |
| 2018/0360814 A1 | 12/2018 | Castelli et al. |
| 2019/0000818 A1 | 1/2019 | Benjamin et al. |

(Continued)

FOREIGN PATENT DOCUMENTS

| | | |
|---|---|---|
| WO | 2007137072 A2 | 11/2007 |
| WO | 2008045015 A1 | 4/2008 |

(Continued)

OTHER PUBLICATIONS

Amicus Therapeutics Announces Positive Phase 3 Data From Fabry Monotherapy Study 012, Amicus Therapeutics Press Release, Aug. 20, 2014.

(Continued)

*Primary Examiner* — Raymond J Henley, III

(74) *Attorney, Agent, or Firm* — Servilla Whitney LLC

(57) ABSTRACT

Provided are methods for treatment of Fabry disease in patients having HEK assay amenable mutations in α-galactosidase A. Certain methods comprise administering migalastat or a salt thereof every other day, such as administering about 150 mg of migalastat hydrochloride every other day.

97 Claims, 21 Drawing Sheets

Specification includes a Sequence Listing.

(56) References Cited

U.S. PATENT DOCUMENTS

| | | |
|---|---|---|
| 2019/0183869 A1 | 6/2019 | Castelli |
| 2019/0358302 A1 | 11/2019 | Gotcschall |
| 2019/0388409 A1 | 12/2019 | Lockhart et al. |
| 2020/0215043 A1 | 7/2020 | Benjamin |
| 2020/0222377 A1 | 7/2020 | Castelli et al. |
| 2020/0268890 A1 | 8/2020 | Greene et al. |
| 2021/0030730 A1 | 2/2021 | Castelli et al. |
| 2021/0038579 A1 | 2/2021 | Barth et al. |
| 2021/0038581 A1 | 2/2021 | Castelli et al. |
| 2021/0038582 A1 | 2/2021 | Castelli et al. |
| 2021/0038583 A1 | 2/2021 | Castelli et al. |
| 2021/0038624 A1 | 2/2021 | Barth |
| 2021/0038625 A1 | 2/2021 | Benjamin et al. |
| 2021/0069161 A1 | 3/2021 | Castelli et al. |
| 2021/0069162 A1 | 3/2021 | Castelli et al. |
| 2021/0085660 A1 | 3/2021 | Castelli et al. |
| 2021/0085661 A1 | 3/2021 | Castelli et al. |
| 2021/0251971 A1 | 8/2021 | Benjamin et al. |
| 2021/0251972 A1 | 8/2021 | Skuban |
| 2021/0315875 A1 | 10/2021 | Benjamin |

FOREIGN PATENT DOCUMENTS

| | | |
|---|---|---|
| WO | 2008134628 A3 | 11/2008 |
| WO | 2009102895 A3 | 8/2009 |
| WO | 2010048532 A1 | 4/2010 |
| WO | 2010138608 A1 | 12/2010 |
| WO | 2011063048 A2 | 5/2011 |
| WO | 2012071451 A2 | 5/2012 |
| WO | 2012125402 A3 | 9/2012 |
| WO | 2012/154681 A1 | 11/2012 |
| WO | 2013091897 A1 | 6/2013 |
| WO | 2014014938 A1 | 1/2014 |
| WO | 2017165164 A1 | 9/2017 |
| WO | 2018017721 A1 | 1/2018 |
| WO | 2018132471 A1 | 7/2018 |
| WO | 2018222655 A1 | 12/2018 |
| WO | 2019017938 A1 | 1/2019 |
| WO | 2019046244 A1 | 3/2019 |
| WO | 2019157047 A1 | 8/2019 |
| WO | 2019157056 A1 | 8/2019 |
| WO | 2020040806 A1 | 2/2020 |
| WO | 2020252129 A1 | 12/2020 |

OTHER PUBLICATIONS

Amicus Therapeutics Announces Presentations and Posters at 12th Annual WORLDSymposium™ 2016, Amicus Therapeutics Press Release, Feb. 10, 2016.
Amicus Therapeutics, Current Report Pursuant to Section 13 or 15(d) of the Securities Exchange Act of 1934 (Form 8-K) (Mar. 3, 2016).
MSDS—Deoxygalactonojirimycin (hydrochloride), according to Regulation (EC) No. 1907/2006 as amended by (EC) No. 2015/830 and US OSHA HCS 2015, 1-5.
Benjamin, Elfrida R., et al.,"The validation of pharmacogenetics for the identification of Fabry patients to be treated with migalastat", Genetics in Medicine, vol. 19, No. 4, Sep. 22, 2016, 430-438.
Benjamin, E. R., et al., "The Validation of Pharmacogenetics in the Identification of Target Fabry Patients for Treatment with Migalastat", Posters at WORLDSymposium™ 2016, Mar. 1, 2016.
Bichet, D. G., et al., "Persistence of Positive Renal and Cardiac Effects of Migalastat in Fabry Patients with Amenable Mutations Following 30 Months of Treatment in the ATTRACT Study", Posters at WORLDSymposium™ 2016, Mar. 1, 2016.
Germain, Dominique P., et al., "Efficacy of the pharmacologic chaperone migalastat in a subset of male patients with the classic phenotype of Fabry disease and migalastat-amenable variants: data from the phase 3 randomized, multicenter, double-blind clinical trial and extension study", Genetics in Medicine, vol. 21, No. 9, Feb. 6, 2019, 1987-1997.
Germain, D.P., et al., "Treatment of Fabry's Disease with the Pharmacologic Chaperone Migalastat", The New England Journal of Medicine 375;6, Aug. 11, 2016, 545-555.
Hughes, Derralynn A., et al., "Oral pharmacological chaperone migalastat compared with enzyme replacement therapy in Fabry disease: 18-month results from the randomised phase III ATTRACT study", J Med Genet 2017; 54, Nov. 10, 2016, 288-296.
Hughes, D., et al., "Phenotype of Fabry Disease in Patients with Mutations Amenable to Migalastat", Posters at WORLDSymposium™ 2016, Mar. 1, 2016.
Johnson, F. K., et al., "Comparison of Integrated White Blood Cell Alpha-Galactosidase A Activity Exposure Between Every-Other-Day Orally Administered Migalastat and Biweekly Infusions of Agalsidase Beta or Agalsidase Alfa", Posters at WORLDSymposium™ 2016, Mar. 1, 2016.
Khanna, Richie, et al., "Co-Administration of the Pharmacological Chaperone AT2221 with A Proprietary Recombinant Human Acid Alpha-Glucosidase Leads to Greater Plasma Exposure and Substrate Reduction Compared to Alglucosidase Alfa", Posters atWORLDSymposium™ 2016, Mar. 1, 2016.
Lukas, Jan, et al., "Functional and Clinical Consequences of Novel Alpha-Galactosidase A Mutations in Fabry Disease", Human Mutation, vol. 0, No. 0, Sep. 29, 2015, 1-9.
Lukas, Jan, et al., "Functional Characterisation of Alpha-Galactosidase A Mutations as a Basis for a New Classification System in Fabry Disease", PLOS Genetics, vol. 9 Issue 8,(e1003632), Aug. 1, 2013, 1-10.
Najafian, B., et al., "Six months of Migalastat Treatment Reduces Podocyte Globotriaosylceramide Content in Adult Male Patients with Fabry Disease", Posters at WORLDSymposium™ 2016, Mar. 1, 2016.
Narita, Ichiei, et al., "Efficacy and safety of migalastat in a Japanese population: a subgroup analysis of the ATT RAC T study", Clinical and Experimental Nephrology (2020) 24, Dec. 30, 2019, 157-166.
"A Phase 2, Open-Label, Multicenter, Ascending-Dose, 12-Week Study to Evaluate the Safety, Tolerability, Pharmacokinetics, and Pharmacodynamics of AT1001 in Patients with Fabry Disease", ClinicalTrials.gov Archive, Sep. 21, 2005.
"A Phase 2, Open-Label, Multiple Dose Level, 12-Week Study to Evaluate the Safety, Tolerability, and Pharmacodynamics of AT1001 in Female Patients With Fabry Disease", ClinicalTrials.gov Archive, Mar. 17, 2006.
"A Phase 2, Open-Label, Multiple Dose Level, 12-Week Study to Evaluate the Safety, Tolerability, and Pharmacodynamics of AT1001 in Female Patients with Fabry Disease", EU Clinical Trials Register, Feb. 13, 2013.
"A Phase 2, Open-Label, Single Dose Level, 12-Week Study to Evaluate the Safety, Tolerability, and Pharmacodynamics of AT1001 in Patients With Fabry Disease", ClinicalTrials.gov Archive, Jan. 30, 2006.
"A Phase 2, Open-Label, Single Dose Level, 24-Week Study to Evaluate the Safety, Tolerability, and Pharmacodynamics of AT1001 in Patients With Fabry Disease", ClinicalTrials.gov Archive, Jan. 30, 2006.
"A Phase 2, Open-Label, Single Dose Level, 24-Week Study to Evaluate the Safety, Tolerability, and Pharmacodynamics of AT1001 in Patients with Fabry Disease", EU Clinical Trials Register, Oct. 17, 2005.
"Study of the Effects of Oral AT1001 (Migalastat Hydrochloride) in Patients With Fabry Disease", ClinicalTrials.gov Archive, as of Mar. 31, 2016, http://clinicaltrials.gov/ct2/history/NCR00925301?V_55.
"GALAFOLD Product Information (original version)", May 30, 2016, 45 pages.
"GALAFOLD Summary of Product Characteristics", Aug. 14, 2018, 49 pages.
"Galafold U.S. Label", Revised Aug. 10, 2018, 24 pages.
"Long-Term Migalastat Treatment Stabilizes Renal Function in Patients With Fabry Disease: Results From a Phase 3 Clinical Study (AT1001-041)", Presented at the 13th International Congress of Inborn Errors of Metabolism; Sep. 5-8, 2017; Rio de Janeiro, Brazil, 1 page.

(56) References Cited

OTHER PUBLICATIONS

PCT Application No. PCT/US20/14531; Filed Jan. 22, 2020. "Methods of Reducing Cerebrovascular Events in Patients With Fabry Disease".

PCT International Search Report and Written Opinion in PCT/US2018/035032 dated Sep. 27, 2018, 18 pages.

U.S. Appl. No. 16/222,305, filed Dec. 17, 2018. Method To Predict Response To Pharmacological Chaperone Treatment Of Diseases.

U.S. Appl. No. 16/642,620, filed Feb. 27, 2020. "Methods Of Enhancing And/Or Stabilizing Cardiac Function In Patients With Fabry Disease".

Williams, Hadis , et al., "Effects of Long-Term Migalastat Treatment on Renal Function by Baseline Proteinuria in Patients (PTS) with Fabry Disease", Nephrology Dialysis Transplantation, vol. 33, 2018 (Supplement 1): i346-i348.

U.S. Appl. No. 16/744,884, filed Jan. 16, 2020. "Methods Of Treating Fabry Disease In Patients Having The G9331A Mutation In The GLA Gene".

U.S. Appl. No. 16/806,404, filed Mar. 2, 2020. "Dosing Regimens For The Treatment Of Fabry Disease".

U.S. Appl. No. 16/817,877, filed Mar. 13, 2020. "Methods Of Treating Fabry Patients Having Renal Impairment".

U.S. Appl. No. 16/678,183, filed Nov. 11, 2019. "Methods Of Treating Fabry Patients Having Renal Impairment".

U.S. Appl. No. 16/817,888, filed Mar. 13, 2020. "Methods Of Treating Fabry Patients Having Renal Impairment".

U.S. Appl. No. 16/817,895, filed Mar. 13, 2020. "Methods Of Treating Fabry Patients Having Renal Impairment".

U.S. Appl. No. 16/817,900, filed Mar. 13, 2020. "Methods Of Treating Fabry Patients Having Renal Impairment".

U.S. Appl. No. 16/817,908, filed Mar. 13, 2020. "Methods Of Treating Fabry Patients Having Renal Impairment".

U.S. Appl. No. 16/817,911, filed Mar. 13, 2020. "Methods Of Treating Fabry Patients Having Renal Impairment".

U.S. Appl. No. 16/817,918, filed Mar. 13, 2020. "Methods Of Treating Fabry Patients Having Renal Impairment".

U.S. Appl. No. 16/817,925, filed Mar. 13, 2020. "Methods Of Treating Fabry Patients Having Renal Impairment".

U.S. Appl. No. 16/817,927, filed Mar. 13, 2020. "Methods Of Treating Fabry Patients Having Renal Impairment".

Feldt-Rasmussen, U., et al., "Response of Patients With Fabry Disease With the Amenable GLA Mutation p. N215S to Treatment With Migalastat", Presented at the 13th International Congress of Inborn Errors of Metabolism; Sep. 5-8, 2017; Rio de Janeiro, Brazil.

Hughes, D. A., et al., "Response of Patients With Fabry Disease With the Amenable GLA Mutation p.N215S to Treatment With Migalastat (ATTRACT Study)", Presented at the 13th Annual WORLDSymposium, Feb. 13-17, 2017, San Diego, CA, 1 page.

Johnson, Franklin K., et al., "An Open-Label Study to Determine the Pharmacokinetics and Safety of Migalastat HCI in Subjects with Impaired Renal Function and Healthy Subjects with Normal Renal Function", American College of Clinical Pharmacology, Clinical Pharmacology in Drug Development 2015, 4(4) 256-261.

Johnson, F. K., et al., "Pharmacokinetic Simulation of a 150-mg Every Other Day Dose Regimen for the Pharmacological Chaperone Migalastat HCI in Fabry Disease", Presented at the 2017 College of Clinical Pharmacology Annual Meeting, Sep. 17-19, 2017, San Diego, CA, 1 page.

Nicholls, K., et al., "Renal Outcomes With Up to 9 Years of Migalastat in Patients With Fabry Disease: Results From an Open-label Extension Study", Presented at the 14th Annual WORLDSymposium, Feb. 5-9, 2018, San Diego, CA, 1 page.

Schiffmann, R., et al., "Long-Term Migalastat Treatment Stabilizes Renal Function in Patients With Fabry Disease: Results from a Phase 3 Clinical Study (AT1001-041)", Presented at the 54th European Renal Association—European Dialysis and Transplant Association Congress; Jun. 3-6, 2017; Madrid, Spain, 1 page.

Skuban, Nina , et al., "Clinical Outcomes with Migalastat in Patients with Fabry Disease Based on Degree of Renal Impairment: Results from Phase 3 Trials", Nephrology Dialysis Transplantation, vol. 33, 2018 (Supplement 1): i346.

Sunder-Plassmann, Gere , et al., "Migalastat for the treatment of Fabry disease", Expert Opinion on Orphan Drugs, 2018, vol. 6, No. 5, pp. 301-309.

Germain, Dominique P., et al., "Safety and pharmacodynamic effects of a pharmacological chaperone on !-galactosidase A activity and globotriaosylceramide clearance in Fabry disease: report from two phase 2 clinical studies", Orphanet Journal of Rare Diseases 2012, 7:91, 1-11.

Giugliani, R., et al., "A Phase 2 study of migalastat hydrochloride in females with Fabry disease: Selection of population, safety and pharmacodynamic effects", Molecular Genetics and Metabolism 109, 2013, 86-92.

U.S. Appl. No. 17/148,817, filed Jan. 14, 2021, 170 pages.

J Inherit Metab Dis (2007) 30 (Supple 1).

"Fabry mutants list", http://fabry-database.org/mutants/, accessed Jan. 24, 2023.

"Galafold EP Label Summary of Product Characteristics", Feb. 2021, 59 pgs.

"Galafold EP Label Summary of Product Characteristics", May 2022, 59 pages.

"Galafold Product Information", Dec. 2021, 28 pages.

"Galafold Summary of Product Characteristics", Feb. 2021, 28 pages.

"Lukas 2013 Supplementary Table".

"Table S3. List of mutations and their reference.".

Ashley, Grace Ann, "a-Galactosidase A: Mutation analysis in patients with Fabry disease and expression and regulation in transgenic mice", A dissertation submitted to the Graduate Faculty o f the Mount Sinai Graduate School of Biological Sciences, Biomedical Sciences Doctoral Program (2001).

Ataides, Thiago Lacerda, et al., "Clinical Nephrology, Primary and Secondary Glomerulonephritis—1", Nephrology Dialysis Transplantation 30 (Supplement 3): iii104-iii124, 2015 doi:10.1093/ndt/gfv171.55.

Benjamin, E. R., et al., "The pharmacological eliaperone 1-deoxygalactonojirimycin Increases a-galactosidase A levels in Fabry patient cell lines", J Inherit Metab Dis (2009 ) 32:424-440 DOT I(U007/sl0545-009-1 077-0.

Benjamin , et al., "The Validation of Pharmacogenetics for the Identification of Fabry Patients for Treatment with Migalastat", Supplementary Information (2017).

Brennan, Paul , et al., "Case-finding in Fabry disease: experience from the North of England", J Inherit Metab Dis (2014) 37:103-107 DOI 10.1007/s10545-013-9629-8.

Brennan, P. , et al., "Case-finding in Fabry disease: experience from the North of England", Supplementary Online Material (2014).

Csányi, Beáta , et al., "Identification of a Novel GLA Gene Mutation, p.Ile239Met, in Fabry Disease With a Predominant Cardiac Phenotype", Novel P.ILE239MET Gla Mutation in Fabry Disease, vol. 158, No. 3, May 2017.

Desnick , et al., "Posters Metabolic Disorders", The American Society of Human Genetics (2015).

Dobrovolny, Robert , et al., "Relationship between X-inactivation and clinical Involvement In Fabry heterozygotes. Eleven novel mutations in the a-galactosidase A gene in the Czech and Slovak population", J Mol Med (2005) 83: 647-654 DOI 10.1007/s00109-005-0656-2.

Doi, Kent , et al., "High-throughput screening identified disease-causing mutants and functional variants of a-galactosidase A gene in Japanese male hemodialysis patients", Journal of Human Genetics (2012) 57, 575-579.

Echevarria, L. , et al., "X-chromosome inactivation in female patients with Fabry disease", Clinical Genetics 2016: 89:44-54.

Benjamin, Elfrida R., et al., "The validation of pharmacogenetics for the identification of Fabry patients to be treated with migalastat", Genetics in Medicine, vol. 19, No. 4, Sep. 22, 2016 (Sep. 22, 2016), pp. 430-138, XP055582063, US ISSN: 1098-3600, DOI: 10. 1038/gim.2016. 122 table 11SA.

(56) References Cited

OTHER PUBLICATIONS

Fan, Jian-Qiang, et al., "Accelerated transport and maturation of lysosomal alpha-galactosidase A in Fabry lymphoblasts by an enzyme inhibitor", Nat. Med. vol. 5 No. 1, 1999, 112-115.
Favalli, Valentina, et al., "Genetic Screening of Anderson-Fabry Disease in Probands Referred From Multispecialty Clinics", Journal of the American College of Cardiology, vol. 68, No. 10, 2016.
Flanagan, John J., et al., "The pharmacological chaperone 1-deoxynojirimycin increases the activity and lysosomal trafficking of multiple mutant forms of acid alpha-glucosidase", Human Mutation, vol. 30, Issue 12, 1683-1692.
Froissart, Roseline, et al., "Fabry disease: D313Y is an a-galactosidase A sequence variant that causes pseudodeficient activity in plasma", Molecular Genetics and Metabolism 80 (2003) 307-314.
Fukutomi, Motoki, et al., "Japanese patients with Fabry disease predominantly showing cardiac and neurological manifestation with novel missense mutation: R220P", Journal of Cardiology 62 (2013) 63-69.
Garman, Scott C., et al., "Structural basis of Fabry disease", Molecular Genetics and Metabolism 77 (2002) 3-11.
Garman, Scott C., et al., "The Molecular Defect Leading to Fabry Disease: Structure of Human a-Galactosidase", J. Mol. Biol. (2004) 337, 319-335.
Germain, Dominique P., et al., "Safety and pharmacodynamic effects of a pharmacological chaperone on a-glactosidase A. activity and globotriaosylceramide clearance in Fabry disease: report from two phase 2 clinical studies", Orphanet Journal of Rare Diseases 7:91, 2012, 11 pgs.
Havndrup, Ole, et al., "Fabry disease mimicking hypertrophic cardiomyopathy: genetic screening needed for establishing the diagnosis in women", European Journal of Heart Failure (2010) 12, 535-540.
Ichinose, Mayuri, et al., "Significance of screening for Fabry disease among male dialysis patients", Clin Exp Nephrol (2005) 9:228-232.
Ishii, Satoshi, et al., "Role of Ser-65 in the activity of a-galactosidase A: characterization of a point mutation (S65T) detected in a patient with Fabry disease", Archives of biochemistry and biophysics, 377(2), May 15, 2000 (May 15, 2000), 228-233.
Iwafuchi, Yoichi, et al., "Enzyme replacement therapy in a patient of heterozygous Fabry disease: clinical and pathological evaluations by repeat kidney biopsy and a successful pregnancy", CEN Case Rep (2017) 6:210-214.
Johnson, Franklin K., et al., "An Open-Label Study to Determine the Pharmacokinetics and Safety of Migalastat HCI in Subjects With Impaired Renal Function and Healthy Subjects With Normal Renal Function", Clinical Pharmacology in Drug Development, vol. 4, pp. 256-261 (2015).
Johnson, Britt, et al., "Analysis of Lyso-Globotriaosylsphingosine in Dried Blood Spots", Ann Lab Med 2013;33:274-278.
Kawano, Makoto, et al., "Significance of Asymmetric Basal Posterior Wall Thinning in Patients With Cardiac Fabry's Disease", The American Journal of Cardiology (2007).
Kobayashi, H., et al., "A retrospective ESI-MS/MS analysis of newborn blood spots from 18 symptomatic patients with organic acid and fatty acid oxidation disorders diagnosed either in infancy or in childhood", J Inherit Metab Dis Short Report #065 (2007).
Koulousios, Konstantinos, et al., "Fabry disease due to D313Y and novel GLA mutations", BMJ Open 2017;7:e017098. doi: 10.1136/bmjopen-2017-017098.
Kroepfl, TH., et al., "A novel 6 bp insertion in exon 7 associated with an unusual phenotype in a family with Fabry disease", J. Inherit. Metab. Dis. 25 (2002) 695-696.
Lee, Sheng-Hung, et al., "High-throughput detection of common sequence variations of Fabry disease in Taiwan using DNA mass spectrometry", Molecular Genetics and Metabolism 111 (2014) 507-512.
Liao, Hsuan-Chieh, et al., "Detecting multiple lysosomal storage diseases by tandem mass spectrometry—A national newborn screening program in Taiwan", Clinica Chimica Acta 431 (2014) 80-86.
Liao, Hsuan-Chieh, et al., "Functional and biological studies of a-galactosidase A variants with uncertain significance from newborn screening in Taiwan", Molecular Genetics and Metabolism 123 (2018) 140-147.
Lin, Hsiang-Yu, et al., "Clinical observations on enzyme replacement therapy in patients with Fabry disease and the switch from agalsidase beta to agalsidase alfa", Journal of the Chinese Medical Association xx (2013) 1-8.
Lin, Hsiang-Yu, et al., "High Incidence of the Cardiac Variant of Fabry Disease Revealed by Newborn Screening in the Taiwan Chinese Population", Circ Cardiovasc Genet, Oct. 2009, pages, pp. 450-456.
Linthorst, Gabor E., et al., "a-Galactosidase A deficiency in Dutch patients on dialysis: a critical appraisal of screening for Fabry disease", Nephrol Dial Transplant (2003) 18: 1581-1584.
Lukas, Jan, et al., "Functional and Clinical Consequences of Novel a-Galactosidase A Mutations in Fabry Disease", Human Mutation, vol. 00, No. 0, 1-9, 2015.
Lukas, Jan, et al., "Functional Characterisation of Alpha-Galactosidase A Mutations as a Basis for a New Classification System in Fabry Disease", PLoS Genet 9(8): e1003632. doi:10.1371/journal.pgen.1003632.
Matsuda, Mitsuhiro, et al., "Novel G144D mutation of the GLA gene in a Chinese patient with Fabry disease", The Journal of Dermatology 2014.
Matsuzawa, Fumiko, et al., ""Fabry disease: correlation between structural changes in [alpha] -galactosidase, and clinical and biochemical phenotypes",", Human Genetics, Springer, Berlin, DE, vol. 117, No. 4, Aug. 1, 2005, 317-328.
Mehta, A, et al., "Enzyme replacement therapy with agalsidase alfa in patients with Fabry's disease: an analysis of registry data", Lavet 2009, vol. 374: 1986-96.
Mignani, Renzo, et al., "Agalsidase therapy in patients with Fabry disease on renal replacement therapy: a nationwide study in Italy", Nephrol Dial Transplant (2008) 23:1628-1635, Dec. 5, 2007.
Mulls, K., et al., "Measurement of urinary CDH and CTH by tandem mass spectrometry in patients hemizygous and heterozygous for Fabry disease", J. Inherit. Metab.Dis. 28 (2005) 3548.
Nakagawa, Naoki, et al., "Clinical and Genetic Investigation of a Japanese Family With Cardiac Fabry Disease", Int Heart J, vol. 52, No. 5, Sep. 2011.
Namazova-Baranova, Leyla Seymurovna, et al., "Fabry disease in children: a federal screening programme in Russia", Eur J Pediatr (2017) 176:1385-1391.
Okumiya, Toshika, et al., "Galactose Stabilizes Various Missense Mutants of «-Galactosidase in Fabry Disease", Biochemical and Biophysical Research Communications, vol. 214, No. 3, Sep. 25, 1995, pp. 1219-1224.
Okur, Ilyas, et al., "Screening for Fabry disease in patients undergoing dialysis for chronic renal failure in Turkey dentification of new case with novel mutation", Gene 527(2013)42-47.
Pan, Xiaoxia, et al., "Genotype: A Crucial but Not Unique Factor Affecting the Clinical Phenotypes in Fabry Disease", PLoS ONE 11(8): e0161330.
Pereira, F.S., et al., "Genomic analysis of Brazilian patients with Fabry disease", Brazilian Journal of Medical and Biological Research (2007) 40: ISSN 0100-879X.
Prabakaran, Thaneas, et al., "Long-term enzyme replacement therapy is associated with reduced proteinuria and preserved proximal tubular function in women with Fabry disease", Nephrol Dial Transplant (2014) 29: 619-625.
Ranieri, Michela, et al., "Fabry Disease: Recognition, Diagnosis, and Treatment of Neurological Features", Curr Treat Options Neurol (2016) IS: 33.
Saito, Seiji, et al., "Comparative Study of Structural Changes Caused by Different Substitutions at the Same Residue on a-Galactosidase A", PLoS ONE 8(12): e84267 doi:10.1371/journal.pone.0084267.
Savostyanov, K.V., et al., "The New Genome Variants in Russian Children with Genetically Determined Cardiomyopathies Revealed with Massive Parallel Sequencing", Annals of the Russian Academy of Medical Sciences. 2017;72 (4):242-253.

(56) References Cited

OTHER PUBLICATIONS

Schiffmann, R., et al., "Cardiac Outcomes With Long-term Migalastat Treatment in Patients With Fabry Disease: Results From Phase 3 Trials", 2018.
Scott, C. Ronald, et al., "Identification of infants at risk for developing Fabry, Pompe or Mucopolysaccharidosis-I from newborn blood spots by tandem mass spectrome", Pediatr. Aug. 2013; 163(2): 498-503. doi: 10.1016/j.ipeds.2013.01.031.
Serebrinsky, G., "Late onset variants in Fabry disease: Results in high risk population screenings in Argentina", Molecular Genetics and Metabolism Reports 4 (2015) 19-24.
Sheng, Sen, et al., "Fabry's disease and stroke: Effectiveness of enzyme replacement therapy (ERT) in stroke prevention, a review with meta-analysis", Journal of Clinical Neuroscience 65 (2019) 83-86.
Shin, Sang H., "Prediction of Response of Mutated a-Galactosidase A to a Pharmacological Chaperone", Pharmacogenetics and Genomics, Lippincott Williams & Wilkins, Philadelphia, PA, US, vol. 18, No. 9, Sep. 1, 2008, pp. 773-780.
Sirrs, S., et al., "Baseline characteristics of patients enrolled in the Canadian Fabry Disease Initiative", Molecular Genetics and Metabolism 99 (2010) 367-373.
Spada, Marco, et al., "High Incidence of Later-Onset Fabry Disease Revealed by Newborn Screening", The American Journal of Human Genetics, vol. 79, Jul. 2006.
Sunder-Plassmann, Gere, et al., "Migalastat for the treatment of Fabry disease", Expert Opinion on Orphan Drugs, 6:5, 301-309, DOI: 10.1 080/21 678707.201 8. 1 469978.
Takahashi, Naoki, "A heterozygous female with Fabry disease due to a novel α-galactosidase A mutation exhibits a unique synaptopodin distribution in vacuolated podocytes", Clin Nephrol. May 2015;83(5):301-8. doi: 10.5414/CN108317. PMID: 25295576., Oct. 8, 2014.
Tsukimura, Takahiro, et al., "Plasma mutant α-galactosidase A protein and globotriaosylsphingosine level in Fabry disease", Molecular Genetics and Metabolism Reports 1 (2014) 288-298.
Tuttolomondo, Antonino, et al., "Novel alpha-galactosidase A mutation in a female with recurrent strokes", Clinical Biochemistry 45 (2012) 1525-1530.
Umeda, Toshiko, et al., "Identification of a novel GLA mutation (F69 L) in a Japanese patient with late-onset Fabry disease", Human Genome Variation (2015) 2, 15044; doi:10.1038/hgv.2015.44.
Van Der Tol, Linda, et al., "In Patients with an a-Galactosidase A Variant, Small Nerve Fibre Assessment Cannot Confirm a Diagnosis of Fabry Disease", JIMD Reports DOI 10.1007/8904_2015_503, Nov. 14, 2015.
Vedder, Anouk C., et al., "Treatment of Fabry Disease: Outcome of a Comparative Trial with Agalsidase Alfa or Beta at a Dose of 0.2 mg/kg", PLoS ONE 2(7): e598. doi:10.1371/journal.pone.0000598 (2007).
Wu, Yi Shuan, et al., "Migalastat Tissue Distribution: Extrapolation From Mice to Humans Using Pharmacokinetic Modeling and Comparison With Agalsidase Beta Tissue Distribution in Mice", Clinical Pharmacology in Drug Development 2021, 10(9) 1075-1088.
Ebrahim, Hatim Y., et al., "Functional analysis of variant lysosomal acid glycosidases of Anderson-Fabry and Pompe disease in a human embryonic kidney epithelial cell line (HEK 293 T)", 2012, 10 pgs.
Sakac, Dejan, et al., "Fabry disease, do we think enough about this multisystemic disorder?—A presentation of three cases in a Serbial family", 2012, 620-622.
Citro, Valentina, et al., "The Large Phenotypic Spectrum of Fabry Disease Requires Graduated Diagnosis and Personalized Therapy: A Meta-Analysis Can Help to Differentiate Missense Mutations", Int. J. Mol. Sci. 2016, 17, 2010.
Thomas, Alison Sian Buchanan, "Vascular Events in Fabry and Gaucher Disease", Thesis submitted to Cancer Institute for the degree of MD (Res) (2014).

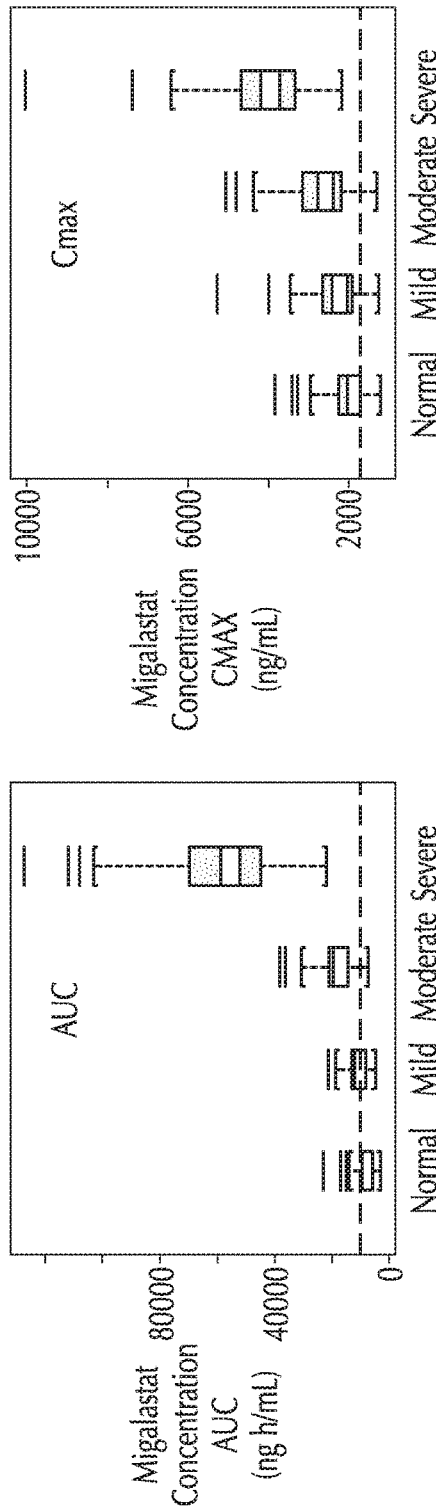
FIG. 9A
FIG. 9C
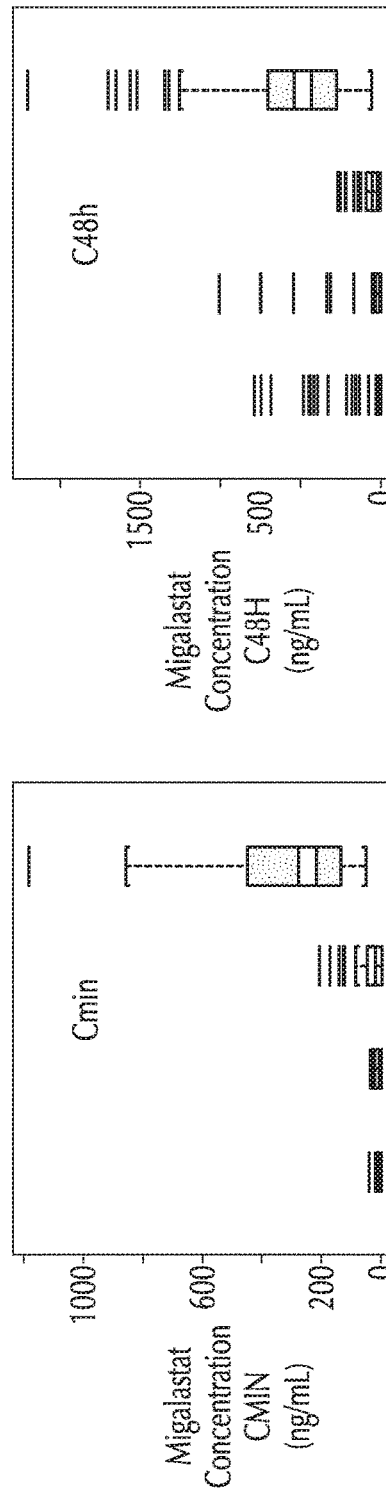
FIG. 9B
FIG. 9D

```
cccttctgtaggggcagagaggttctacttcattactgcgtctcctgggaaggccatcag    60
gactgctggctaaagtgggaaccaggactctttgtgagttaagaatttgtgtatttatat   120
gtgtgttatacacattttttaaaaaactgtaacgacatcaggttgagcagtcgtctccgg   180
gtggtgaattatgtgtattttttaaattttatactatattgttattttttcaaatgttcgaa  240
attgaatatgtagattgttgttatcagcagaaaaataaacattattcaaatactctattc   300
agtaaagtaatttattgggcgcctttgtcaagcacgcatttgcctagatgtgactctaca   360
gataaaattcacttggggcctcccctta cagacaatcaggcagtggagactgagtgcctg   420
aatggatagaccagcactcagaccactattttcagtatctgttttcttaactcagggcc    480
gtggttttcaaacgttttcgccttacggtcacccttagggtccccgagaccggcccag     540
acagacagatatacaaaaacacatacacagtcatgagcgtccaccatttccccaccaggc   600
gcagcacaggcggcttcccggcactgagatggggggggaggagggagagagcgcgagggg    660
gagggaaagcagagaacgaaagaggcggaggcggccccgaaccccgctctggtcttca     720
tcatcaccaccctgggtccccagttcccacccacacaccaacctctaacgataccgggt    780
aattttcctccttcttccctcaaacggctatagcgagacggtagacgacgaccagaacta   840
cttctgctcacgtaagcgagtaatcacgtgagcgcctacgtcatgtgagatctcggtcac   900
gtgagcaactctcggcttaaactcgggatcactaaggtgccgcacttccttctggtatgg   960
aaatagggcgggtcaatatcaagaaaggaagagggtgattggttagcggaacgtcttacg  1020
tgactgattattggtctacctctggggataaccgtcccagttgccagagaaacaataacg  1080
tcattatttaataagtcatcggtgattggtccgcccctgaggttaatcttaaaagcccag  1140
gttacccgcggaaatttatgctgtccggtcaccgtgacaatgcagctgaggaacccagaa  1200
ctacatctgggctgcgcgcttgcgcttcgcttcctggccctcgtttcctgggacatccct  1260
ggggctagagcactggacaatggattggcaaggacgcctaccatgggctggctgcactgg  1320
gagcgcttcatgtgcaaccttgactgccaggaagagccagattcctgcatcaggtatcag  1380
atattgggtactcccttcccttcttttccatgtgtttgggtgtgtttggggaactgga    1440
gagtctcaacgggaacagttgagcccgagggagagctccccacccgactctgctgctgc   1500
ttttttatccccagcaaactgtcccgaatcaggactagccctaaacttctctgtgtgac   1560
cttcctgggatgggagtccggccagcggcccctgtttctttctctctctctctctctct   1620
cgttctccttctctttctctttctcttctttcctctctcttctctctctccctgcccgg   1680
ttctcttttttcactgctccttgcagagcagggccaccccataggcagtgtgcccaaagt  1740
agccctgcccggttctattcagacccttcttgtgaacttctgctcttcctctgccgggtg  1800
ctaaccgttagaacatctagggtgggtaggaggaatggggaactaagattcgtgccattt  1860
tttctccttttggggtcgtggatttctcggcagtatctcgagggagttagagagaccata  1920
aggtcgctgagatctctcccacctcgcccatgagcgtggcatcaggctggaaggttgaca  1980
tggaggaactttatacatttacacctttgcgtgagggttgaggctggattagataggtat  2040
tgaacatatctgaccctcacaatccttatctgtaaattgggattacaaccttttaatttc  2100
agggagctgacaaaaaaatctgaaaaatagttcttatctcacacaggtgagttttcaag   2160
gagataacctatttaaagtacatagcacagcgcttgaccattcaactgcgcttacagagc  2220
aaatgttcaatgggaaatgaatgtaaatctacaaatctgaatgaatatgtgtattttc   2280
tggagagaggatatttaccttcttcaaattctcaagggctctgtgatttaaaaaaggt    2340
taggaatcactgatagatgttggtaaaaggtggcagtcacagtacatttctgtgtccata  2400
agttattcctatgaatatctttatagataaagtcaggatgttggtcagacatcacagaag  2460
aaattggccttgtaagtttcatgtgaccctgtggtacagtatgtgtggcaattttccca   2520
tcacggattttttttattggtatttgcatctgattataaaactaatgcatgatcattgc   2580
aaaaaatgtagataaagaagagcaaatgaaaataaagatttcccccaccgttccacca    2640
cccagaaataatcatggttttaaatgttaatatacaaccttacaattgttttctatataaa  2700
tgaaaacatagatttctttatttcattattttccataaaaaatggatcatgtttatgtca  2760
tgtttggctaatggcaagaccctggcacccagtctgggctcaaattctgcctcattgtta  2820
cttagccctgtgacattgggtaaattcacttttttttttttttttttttgagacgggg    2880
```

FIG. 14A

```
tctcgctctgtcgcccaggctggagtgcagtggcacgatctcggctcactgcaagtccgc      2940
ctcctggttcacgccattcttctgcctcagcctcccgagtagctgggactacaggcgcc      3000
tgccaccacgcctggctctttttttttttttttttttttttagtacagacggggtttcac     3060
catgttagccagggtggtctcaatctcctgacctcgtgattcgcccgcctcagcctcca      3120
aagtgctggtgtgagccaccgtgcccagccttactttttttttgagagggggtctcact     3180
ctgtcacccaggttggagtgcagtggcgcgatctctgctcagtgcaaactccacctcccg     3240
ggtttaagcagttctcctgtcgtagtctcctgagtagctgggattacaggcacaccacca    3300
cggccagctaattttgtattttcagtagagacgggtttcaccatgttgcccaagctggt      3360
ctcgaactcctggcctcaagtgatctgcccgccttggcctcccagagtgctgggattaca    3420
ggtgtgagccaccgcacccggcctcttttttcttttttagtctatcataccttgcaaata    3480
cagtggttcttcctatgtgttggttttgatatttatgtaatcaaacacatcagttttcc     3540
tttctgatttctgactttggggtcatgctgagaaagtcctttcctacctgaagataatac    3600
agtatatacgtttcttactagtattttgtggattttaaaatatttaaatctttagtcc      3660
atctgaacttgttcttctatcagaaatgccacatttaataaataataagtcccatggtat    3720
cagatggctggaaggacctcttcgaaactttgtttaattccattaatctgtgtattctt     3780
attctaatgctaatagttccacactagcttcctttatcttttttttctttttttttttt    3840
ttttgagctggagtttcgctcttgttgcccaggctggagtacaatgtcacgatctcggtt    3900
caccgcaacctccgcctcccaggttcaagcaattctcctgcctcatcctcgcgagtagct    3960
ggaattacaggcatgcgccaccacgcctagctattttgtatttttagtagagatggggtt   4020
tctccatgttggtcaggctggtctcaaactcccagcctcaggtgatctgcctgcctcggc    4080
ctcccaaaatgctgttattacaggcgtgagccaccacgcccagccttcatcttttaatga    4140
atgtacatgtatgtaatcttttaggtgaacttttgtaatgttgtgccaagttccttaaa    4200
aagccctttggaagctgggcaggtggccacgcctgtaatcccagcatttgggagtctg     4260
aggcaggtggatcacttgaggccaggagttcaagactagcctagccaaaatgcaaaaccc    4320
tgtctctactaaagatacaaaaattagccggatgcgatggcacatgcctgtaatctcagc    4380
tactcgggaggctgaggtagaagaatcgcttgaaccggggaggcagaggttgcagtgagc    4440
aagatggcgccactgcactccagcctgggtgacagagggagactccatctcaaaaaaaa    4500
aaaaaaaaaagataaaaggaaacctaagtactcttgggctttgttaaggatttgtt      4560
aaatatacaaaggattgcagggaaaattaacttattttaatattgagtatgcttatcca    4620
agagcaaaataatatttctccatttattcaaatcatttaggagcatcatagttttaacat   4680
atgggccttgcacgtatcttaaatttatctctaggcattttaggttgttcagttgttctt   4740
gtgaatgggatcttttctccaaataggattattgttgatatctgttgattatgttaact    4800
ttgtagtttctgactttactgaactgtcttcttagatctaatactcttttcaatttcatc   4860
atatatttctcattcctattttgtttggggttttagggcgggaatattaacgggataag   4920
agagacaaaagaaaatctggaaaaacaattcattttaccttacattgcttgtgattacta   4980
ccacactattactgggttggaaaaaattgtgaaatcccaaggtgcctaataaatgggagg    5040
tacctaagtgttcatttaatgaattgtaatgattattggaatttctctttcagtgagaag    5100
ctcttcatggagatggcagagctcatggtctcagaaggctggaaggatgcaggttatgag    5160
tacctctgcattgatgactgttggatggctccccaaagagattcagaaggcagacttcag    5220
gcagaccctcagcgctttcctcatgggattcgccagctagctaattatgtgagtttatag    5280
ataatgttcttgttcattcagaggactgtaagcacttctgtacagaagcttgtttagaaa    5340
cagccctcatggccgggcgtggtggctcacgctgtaatcccaacactttgggaggccgag    5400
gcgggtggatcacctgaggtcaagagttcaagaccagcctggccaacatggtgaaacccc    5460
aactctattaaaagtacaaaaattagctgggcatggtggtgaacgcctgtaaccccagc    5520
tacttgggaggctgaggcaggagaatcgcttgaacccaggaggtggaagtttcagtgagc    5580
tgagatcacgccattgcactctagcctgggcaacaaaagagaaactccatctcaaaaaaa    5640
aaaacaaggaaaaaagaaacagccctcatgacacttagaaagtagaatagctggctgtt    5700
atctgaacattgaattgtaaggcttatcaggtggactttgcattccatcagcagacaatt    5760
```

FIG. 14B

```
ttttttttttttttttttttgagatggagtctcattctgtctcccaggctggagggcagtg    5820
gtgcgatctcggctcactgcaagctccacctcctgggttcatgccattctcctgcctcag    5880
cctcccaagtagctgggaccacaggcacccgccaccatgcccagttaattttttgtattt    5940
ttagtagagacggggtttcaccatgttagccaagatggtctcgatctcctgacctcgtga    6000
tccgcccacctcggcctcccaaagtgctgggattacaggcatgagccaccgcgcctagcc    6060
tacaaatgttttgtaatagctcttgaggcccatcttggagttctccttttgctaaaacca    6120
ctgaactctctaggaggaaaaaggaacttggttcttgacatatgtgtgcatgtatttcca    6180
tataacctttaggaagctattgcaatggtactataaactagaattttagaagatagaagg    6240
aaaatattctggagatcattgaagagaaatggagtccaacactagttaaagatgatgaag    6300
acagattttttttttgacggagtctcgctctgtcgcccaggctggagtgcagtggcaca    6360
atctcagctcactgcaaccctccacctcttgggttcaagtgattctcctgcctcagcctc    6420
ccaagtagctgggactacaggcgcaccaccacgcccggctaattttttgtatttttagt    6480
agagacaaggttttcaccatattcgccaggctggtctcgaactcctgaccttgtaatccgc    6540
ccaccttggcctcccaaagtgctgggattacaggcatgagccaccgcccggccgatga    6600
agacagattttattcagtactaccacagtagaggaaagagccaagttcaattccaaatac    6660
aacaaagacaggtggagatttatagccaatgagcagattgaggggtcagtggatggaat    6720
atttaagaagacatcaaggg tagggagcttcttgctaaagcttcatgtacttaaacaaga    6780
agggtgggggatgagggaaattgatcagatatcaatggtggcagtattgacttagcagga    6840
ttcttgctaagaggtcttgctaggacagacataggaagccaaggtggaggtctagtcgaa    6900
aagaaggctcatcagagaagtctaactaaagtttggtcaagaagagtcttttgtcaaggta    6960
aatctatcatttccctcaaaaggtaattttcaggatcccatcaggaagattagcatggct    7020
gctagctttctcctcagttctgggctatagctcacatgcctagtttgaactagctcagca    7080
gaactgggggatttattctttgtcttccaacaaactcatctggatgattttggggttg    7140
tggggaaaagccccccaatacctggtgaagtaaccttgtctcttccccagcctggaatgg    7200
ttctctctttctgctacctcacgattgtgcttctacaatggtgactcttttcctccctct    7260
catttcaggttcacagcaaaggactgaagctagggatttatgcagatgttggaaataaaa    7320
cctgcgcaggcttccctgggagttttggatactacgacattgatgcccagacctttgctg    7380
actggggagtagatctgctaaaatttgatggttgttactgtgacagtttggaaaatttgg    7440
cagatggtaatgtttcattccagagatttagccacaaaggaaagaactttgaggccatgg    7500
tagctgagccaaagaaccaatcttcagaattttaaatacccctgtcacaatactggaaata    7560
attattctccatgtgccagagctcccatctcttctctttcagttcattaattaattaatt    7620
aattcatgtaaaatccatgcatacctaaccatagctaatattgtgcacttataattcaag    7680
agggctctaagagttaattagtaattgtaactctctataacatcatttaggggagtccag    7740
gttgtcaatcggtcacagagaaagaagcatcttcattcctgccttcctcaatatacaca    7800
ccatctctgcactacttcctcagaacaatcccagcagtctggaggtactttacacaatt    7860
taagcacagagcaactgcctgtccctgctgctagtttaaacatgaaccttccaggtagcc    7920
tcttcttaaaatatacagccccagctgggcatgatggctcatgcctgtaatcctagcact    7980
ttgggaggctgaggcgggtggattacttgaggtcaggagttcgagaccaccctggccaac    8040
atggtgaaaccccatctctagtaaaaatacaaaaattagctgactttggtggcacatgcc    8100
tgtaatcccagctacttgggaagctgagacagaagagtcacttgaacctgggaaacagag    8160
gttgcagtgagccaagatcgcaccactgcactccaccctggatgacagactgaaccccat    8220
ctcaaaaattaaaataaaataaaataactatatatatagccccagctggaaatt    8280
catttcttccttatttttacccattgttttctcatacaggttataagcacatgtccttg    8340
gccctgaataggactggcagaagcattgtgtactcctgtgagtggcctctttatatgtgg    8400
cccttcaaaaggtgagatagtgagcccagaatccaatagaactgtactgatagatagaa    8460
cttgacaacaaaggaaaccaaggtctccttcaaagtccaacgttacttactatcatccta    8520
ccatctctcccaggttccaaccacttctcaccatcccactgctgtaattatagcctaag    8580
ctaccatcacctggaaagtcatccttgtgtcttcccctttatttcaccattcatgtcctg    8640
```

FIG. 14C

```
tctatcaacagtccttccaccagtatctctaaaatatctcctgaatcagcccacttcctt    8700
ccatcttcactacatgcaccctggccttccaagctactatcggctctcaaccagactgct    8760
gggaccacctgatctctctgcttccactctgtctcaaccccatctatttccaagcagc     8820
actagagttatcatattaaaatgtaaatatcagttttttttttaaagaaaaaaaccctga    8880
gacttaacagagttataaaaaatataaatgtcatcatcagttccctgcttaaaacccta    8940
actcgcttccaattgcacttggaatgaaaccaaactgcactgatccagcccttgcctgcc    9000
tccccaaagtccaaggggtcatggctcttccctggctacactggttttctttctgtccc   9060
tcaacactgcaagcctattgctgccccagggcctttacacttgcttttttctgcctaga   9120
acagttcttccccaaagattttaaagggccgggctccttaacattgaagtcgcagacca   9180
aacgccacatatgcagacagttcttctctaactactttaaaatagccctctgtccattca  9240
ttcttcatcacattaacctgtttaattttcttcagagctccacactatttggaagtat    9300
ttgttgacttgttaccatgtctccccactagagtgtaagtttcatgagggcagggacctt  9360
gtctgactttgactgtatctctcgcatatggttaagtgttaaatagttatttatggaatg  9420
aatccctattattccctcattatctctgcaaaatagtcttttttctcaacatcttaaacc  9480
tgatatcccacctgcctatctacaaactttttttttgcgacagagtctcactgtcaccca  9540
ggctagagtgcagtggcgccatctcggctcactgcaacctccgcctcccgggtttaagcg  9600
attctcttgcctcagcctcccagtagctgggattataggcgtgcgctaccacatctggct  9660
aattttttgtattttagtagagatggtttcaccatgttggccaggcttgtctcgaactcc  9720
tgacctcagatgatccacctgcctcggcctcccaaagtgctgggattacaggcatgagcc  9780
accgtgcccagcctctacaaacttttattccattaacaaactatatgctgggatttaag   9840
ttttcttaatacttgatggagtcctatgtaattttcgagcttttaattttactaagacca  9900
ttttagttctgattatagaagtaaattaactttaagggatttcaagttatatggcctact  9960
tctgaagcaaacttcttacagtgaaaattcattataagggtttagacctccttatggaga  10020
cgttcaatctgtaaactcaagagaaggctacaagtgcctcctttaaactgttttcatctc  10080
acaaggatgttagtagaaagtaaacagaagagtcatatctgttttcacagcccaattata  10140
cagaaatccgacagtactgcaatcactggcgaaattttgctgacattgatgattcctgga  10200
aaagtataaagagtatcttggactggacatcttttaaccaggagagaattgttgatgttg  10260
ctggaccagggggttggaatgacccagatatggtaaaaacttgagccctccttgttcaag  10320
accctgcggtaggcttgtttcctattttgacattcaaggtaaatacaggtaaagttcctg  10380
ggaggaggctttatgtgagagtacttagagcaggatgctgtggaaagtggtttctccata  10440
tgggtcatctaggtaactttaagaatgttcctcctctcttgtttgaattatttcattct   10500
ttttctcagttagtgattggcaactttggcctcagctggaatcagcaagtaactcagatg  10560
gccctctgggctatcatggctgctcctttattcatgtctaatgacctccgacacatcagc  10620
cctcaagccaaagctctccttcaggataaggacgtaattgccatcaatcaggacccttg   10680
ggcaagcaagggtaccagcttagacaggtaaataagagtatatattttaagatggcttta  10740
tacccaataccaactttgtcttgggcctaaatctattttttccttgctcttgatgt      10800
tactatcagtaataaagcttcttgctagaaacattactttatttccaaaataatgctaca  10860
ggatcattttaattttcctacaagtgcttgatagttctgacattaagaatgaatgccaa   10920
actaacagggccacttatcactagttgctaagcaaccacactttcttggttttttcaggga 10980
gacaactttgaagtgtgggaacgacctctctcaggcttagcctgggctgtagctatgata  11040
aaccggcaggagattggtggacctcgctcttataccatcgcagttgcttccctgggtaaa  11100
ggagtggcctgtaatcctgcctgcttcatcacacagctcctcctgtgaaaaggaagcta   11160
gggttctatgaatggacttcaaggttaagaagtcacataaatcccacaggcactgttttg  11220
cttcagctagaaaatacaatgcagatgtcattaaaagacttactttaaaatgtttatttt  11280
attgccaactactacttcctgtccaccttttctccattcactttaaaagctcaaggcta   11340
ggtggctcatgcctgtaatcccagcactttgggaggctgaggcgggcagatcacctgagg  11400
tcgggactttgagacccgcctggacaacatggtgaaaccccatttctaataaaaatataa  11460
aaattagccaggtgtggtggcgcacctgtggtcccagctactctggggctgaggcatga   11520
```

FIG. 14D

```
gaatcgcttgaacccgggagtggaggttgcattgagctgagatcatgccacctcactcca   11580
gcctgggcaacaaagattccatctcaaaaaaaaaaaaaagccaggcacagtggctcatg    11640
cctggaatcccagcacttttggaagctgaggcaggcagatcacttgaggttaggatttca   11700
agaccagcctggctaacatagtaaagccctgtctctactaaaaatacaaaaattagccag   11760
gtatggtggcgagcttctgtagccccagctactcaggagactgaggcaggagaatcactt   11820
gaacccgggaagtggggggtgcagtgacccaagatcacgccactgcattccagcctggg    11880
caacagagcaagactccatctcaaaaaaaaagttctatttccttgaataaaattttccg    11940
aagtttaaacttaggaataaaactattaaacccgtatttactcatccagatacccaccc   12000
cccttgttgagattctctcccaattatcaaaatgtgtagcatatttaactaccaagagct   12060
aaacatcattaagactgaaatgtattaagaaggatgtataggccaggcacggtgtctcac   12120
gcctgtaatcccaacactttgggaggccaagtcgggcggatcacgaggtcaggagatgga   12180
gaccatcctggccaacatggtgaaaccccctctctactaaaaatacaaaaattagccagg   12240
caggtggcaggcacctgtaatcccagctactccagaggctgaggcaggacaatcacttga   12300
acctgggaggcagaggctgcagtgagctgaggttgtaccaattgcactccagcctaggta   12360
acgagcaacactccatctcaaaaaagaaaaaaaaaagatgtataatttggaactgtta    12420
agaggcattttaaaga                                              12436
```

FIG. 14E

```
MQLRNPELHL GCALALRFLA LVSWDIPGAR ALDNGLARTP TMGWLHWERF MCNLDCQEEP   60
DSCISEKLFM EMAELMVSEG WKDAGYEYLC IDDCWMAPQR DSEGRLQADP QRFPHGIRQL  120
ANYVHSKGLK LGIYADVGNK TCAGFPGSFG YYDIDAQTFA DWGVDLLKFD GCYCDSLENL  180
ADGYKHMSLA LNRTGRSIVY SCEWPLYMWP FQKPNYTEIR QYCNHWRNFA DIDDSWKSIK  240
SILDWTSFNQ ERIVDVAGPG GWNDPDMLVI GNFGLSWNQQ VTQMALWAIM AAPLFMSNDL  300
RHISPQAKAL LQDKDVIAIN QDPLGKQGYQ LRQGDNFEVW ERPLSGLAWA VAMINRQEIG  360
GPRSYTIAVA SLGKGVACNP ACFITQLLPV KRKLGFYEWT SRLRSHINPT GTVLLQLENT  420
MQMSLKDLL                                                         429
```

FIG. 15

METHODS OF TREATING FABRY PATIENTS HAVING RENAL IMPAIRMENT

CROSS-REFERENCE TO RELATED APPLICATIONS

This application is a continuation of U.S. application Ser. No. 16/817,881, filed Mar. 13, 2020, which is a continuation of U.S. application Ser. No. 16/678,183, filed Nov. 8, 2019, which is a divisional of U.S. application Ser. No. 16/284,582, filed Feb. 25, 2019, now U.S. Pat. No. 10,471,053, which is a divisional of U.S. application Ser. No. 15/992,336, filed May 30, 2018, now U.S. Pat. No. 10,251,873, which claims the benefit under 35 U.S.C. § 119(e) to U.S. Provisional Application No. 62/512,458, filed May 30, 2017, and U.S. Provisional Application No. 62/626,953, filed Feb. 6, 2018, the entire contents of which are incorporated herein by reference in their entirety.

TECHNICAL FIELD

Principles and embodiments of the present invention relate generally to the use of pharmacological chaperones for the treatment of Fabry disease, particularly in patients with varying degrees of renal impairment.

BACKGROUND

Many human diseases result from mutations that cause changes in the amino acid sequence of a protein which reduce its stability and may prevent it from folding properly. Proteins generally fold in a specific region of the cell known as the endoplasmic reticulum, or ER. The cell has quality control mechanisms that ensure that proteins are folded into their correct three-dimensional shape before they can move from the ER to the appropriate destination in the cell, a process generally referred to as protein trafficking. Misfolded proteins are often eliminated by the quality control mechanisms after initially being retained in the ER. In certain instances, misfolded proteins can accumulate in the ER before being eliminated. The retention of misfolded proteins in the ER interrupts their proper trafficking, and the resulting reduced biological activity can lead to impaired cellular function and ultimately to disease. In addition, the accumulation of misfolded proteins in the ER may lead to various types of stress on cells, which may also contribute to cellular dysfunction and disease.

Such mutations can lead to lysosomal storage disorders (LSDs), which are characterized by deficiencies of lysosomal enzymes due to mutations in the genes encoding the lysosomal enzymes. The resultant disease causes the pathologic accumulation of substrates of those enzymes, which include lipids, carbohydrates, and polysaccharides. Although there are many different mutant genotypes associated with each LSD, many of the mutations are missense mutations which can lead to the production of a less stable enzyme. These less stable enzymes are sometimes prematurely degraded by the ER-associated degradation pathway. This results in the enzyme deficiency in the lysosome, and the pathologic accumulation of substrate. Such mutant enzymes are sometimes referred to in the pertinent art as "folding mutants" or "conformational mutants."

Fabry Disease is a LSD caused by a mutation to the GLA gene, which encodes the enzyme α-galactosidase A (α-Gal A). α-Gal A is required for glycosphingolipid metabolism. The mutation causes the substrate globotriaosylceramide (GL-3) to accumulate in various tissues and organs. Males with Fabry disease are hemizygotes because the disease genes are encoded on the X chromosome. Fabry disease is estimated to affect 1 in 40,000 and 60,000 males, and occurs less frequently in females.

There have been several approaches to treatment of Fabry disease. One approved therapy for treating Fabry disease is enzyme replacement therapy (ERT), which typically involves intravenous infusion of a purified form of the corresponding wild-type protein. Two α-Gal A products are currently available for the treatment of Fabry disease: agalsidase alfa (Replagal®, Shire Human Genetic Therapies) and agalsidase beta (Fabrazyme®; Sanofi Genzyme Corporation). ERT has several drawbacks, however. One of the main complications with ERT is rapid degradation of the infused protein, which leads to the need for numerous, costly high dose infusions. ERT has several additional caveats, such as difficulties with large-scale generation, purification, and storage of properly folded protein; obtaining glycosylated native protein; generation of an anti-protein immune response; and inability of protein to cross the blood-brain barrier to mitigate central nervous system pathologies (i.e., low bioavailability). In addition, replacement enzyme cannot penetrate the heart or kidney in sufficient amounts to reduce substrate accumulation in the renal podocytes or cardiac myocytes, which figure prominently in Fabry pathology.

Another approach to treating some enzyme deficiencies involves the use of small molecule inhibitors to reduce production of the natural substrate of deficient enzyme proteins, thereby ameliorating the pathology. This "substrate reduction" approach has been specifically described for a class of about 40 LSDs that include glycosphingolipid storage disorders. The small molecule inhibitors proposed for use as therapy are specific for inhibiting the enzymes involved in synthesis of glycolipids, reducing the amount of cellular glycolipid that needs to be broken down by the deficient enzyme.

A third approach to treating Fabry disease has been treatment with what are called pharmacological chaperones (PCs). Such PCs include small molecule inhibitors of α-Gal A, which can bind to the α-Gal A to increase the stability of both mutant enzyme and the corresponding wild type.

One problem with current treatments is difficulty in treating patients exhibiting renal impairment, which is very common in Fabry patients and progresses with disease. On average, it take between about 10-20 years for patients to decline from normal kidney function to severe renal impairment, with some countries reporting even faster declines. By some estimates, about 10% of Fabry patients receiving ERT may have moderate renal impairment. Another 25% of males and 5% of females receiving ERT have an estimated glomerular filtration rate (eGFR) of less than 30, corresponding to severe kidney impairment or even renal failure. Of these, about half have severe kidney impairment, and about half are on dialysis.

Unfortunately, renal impairment will progress despite ERT treatment. A patient having an eGFR of 30 may deteriorate to the point of needing dialysis in two to five years. About 30% of patients receiving ERT will end up on dialysis or needing a kidney transplant, depending on the start of ERT. The earlier ERT is commenced, the longer renal function may be preserved, but commencement of ERT may be delayed because Fabry disease is rare and often misdiagnosed.

Further, and as discussed above, ERT often does not sufficiently penetrate the kidneys to reduce substrate accumulation, thereby allowing further damage during disease progression. With PC treatment, the kidneys are often how the drug is cleared from the body, and renal impairment may affect drug pharmacokinetics and/or drug pharmacodynamics. Thus, there is still a need for a treatment of Fabry patients who have renal impairment.

SUMMARY

Various aspects of the present invention relate to the treatment of Fabry patients having renal impairment and/or elevated proteinuria using migalastat. Such treatment can include stabilizing renal function, reducing left ventricular mass index (LVMi), reducing plasma globotriaosylsphingosine (lyso-Gb$_3$) and/or increasing α-Gal A activity in the patient.

One aspect of the present invention pertains to a method for the treatment of Fabry disease in a patient having renal impairment, the method comprising administering to the patient an effective amount of migalastat or salt thereof at a frequency of once every other day. In one or more embodiments, the effective amount is about 100 mg to about 150 mg free base equivalent (FBE).

In one or more embodiments, the patient has mild or moderate renal impairment.

In one or more embodiments, the patient has mild renal impairment.

In one or more embodiments, the patient has moderate renal impairment.

In one or more embodiments, the patient has severe renal impairment.

In one or more embodiments, the patient is an ERT-experienced patient.

In one or more embodiments, the patient is an ERT-naïve patient.

In one or more embodiments, the patient has a proteinuria level of less than 100 mg/24 hr prior to initiating the administration of the migalastat or salt thereof.

In one or more embodiments, the patient has a proteinuria level of 100 to 1,000 mg/24 hr prior to initiating the administration of the migalastat or salt thereof.

In one or more embodiments, the patient has a proteinuria level of greater than 1,000 mg/24 hr prior to initiating the administration of the migalastat or salt thereof.

In one or more embodiments, the migalastat or salt thereof enhances α-Gal A activity in the patient. In one or more embodiments, the α-Gal A activity is white blood cell (WBC) α-Gal A activity.

In one or more embodiments, the administration of the migalastat or salt thereof is effective to reduce LVMi in the patient.

In one or more embodiments, the administration of the migalastat or salt thereof is effective to stabilize plasma lyso-Gb$_3$ in the patient.

In one or more embodiments, the administration of the migalastat or salt thereof is effective to stabilize renal function in the patient.

In one or more embodiments, the effective amount is about 123 mg FBE.

In one or more embodiments, the effective amount is about 123 mg of migalastat free base.

In one or more embodiments, the salt of migalastat is migalastat hydrochloride.

In one or more embodiments, the effective amount is about 150 mg of migalastat hydrochloride.

In one or more embodiments, the migalastat or salt thereof is in an oral dosage form. In one or more embodiments, the oral dosage form comprises a tablet, a capsule or a solution.

In one or more embodiments, the migalastat or salt thereof is administered for at least 28 days.

In one or more embodiments, the migalastat or salt thereof is administered for at least 6 months.

In one or more embodiments, the migalastat or salt thereof is administered for at least 12 months.

Another aspect of the present invention pertains to the use of migalastat to stabilize renal function in a patient diagnosed with Fabry disease and having renal impairment. In various embodiments, the method comprises administering to the patient about 100 mg to about 150 mg FBE of migalastat or salt thereof at a frequency of once every other day.

In one or more embodiments, the patient has mild or moderate renal impairment.

In one or more embodiments, the patient has mild renal impairment.

In one or more embodiments, the patient has moderate renal impairment.

In one or more embodiments, the patient has severe renal impairment.

In one or more embodiments, the patient is an ERT-experienced patient.

In one or more embodiments, the patient is an ERT-naïve patient.

In one or more embodiments, the patient has a proteinuria level of less than 100 mg/24 hr prior to initiating the administration of the migalastat or salt thereof.

In one or more embodiments, the patient has a proteinuria level of 100 to 1,000 mg/24 hr prior to initiating the administration of the migalastat or salt thereof.

In one or more embodiments, the patient has a proteinuria level of greater than 1,000 mg/24 hr prior to initiating the administration of the migalastat or salt thereof.

In one or more embodiments, the migalastat or salt thereof enhances α-Gal A activity.

In one or more embodiments, the effective amount is about 123 mg FBE.

In one or more embodiments, the effective amount is about 123 mg of migalastat free base.

In one or more embodiments, the salt of migalastat is migalastat hydrochloride.

In one or more embodiments, the effective amount is about 150 mg of migalastat hydrochloride.

In one or more embodiments, the migalastat or salt thereof is in an oral dosage form. In one or more embodiments, the oral dosage form comprises a tablet, a capsule or a solution.

In one or more embodiments, the migalastat or salt thereof is administered for at least 28 days.

In one or more embodiments, the migalastat or salt thereof is administered for at least 6 months.

In one or more embodiments, the migalastat or salt thereof is administered for at least 12 months.

In one or more embodiments, administration of the effective amount of the migalastat or salt thereof to a group of patients having mild or moderate renal impairment provides a mean annualized rate of change in eGFR$_{CKD-EPI}$ of greater than $-1.0$ mL/min/1.73 m$^2$.

In one or more embodiments, administration of the effective amount of the migalastat or salt thereof to a group of patients having mild renal impairment provides a mean annualized rate of change in eGFR$_{CKD-EPI}$ of greater than $-1.0$ mL/min/1.73 m$^2$.

In one or more embodiments, administration of the effective amount of the migalastat or salt thereof to a group of patients having moderate renal impairment provides a mean annualized rate of change in eGFR$_{CKD-EPI}$ of greater than −1.0 mL/min/1.73 m$^2$.

Another aspect of the present invention pertains to the use of migalastat to stabilize plasma lyso-Gb$_3$ in a patient diagnosed with Fabry disease and having renal impairment. In various embodiments, the method comprises administering to the patient about 100 mg to about 150 mg FBE of migalastat or salt thereof at a frequency of once every other day.

In one or more embodiments, the patient has mild or moderate renal impairment.

In one or more embodiments, the patient has mild renal impairment.

In one or more embodiments, the patient has moderate renal impairment.

In one or more embodiments, the patient has severe renal impairment.

In one or more embodiments, the patient is an ERT-experienced patient.

In one or more embodiments, the patient is an ERT-naïve patient.

In one or more embodiments, the patient has a proteinuria level of less than 100 mg/24 hr prior to initiating the administration of the migalastat or salt thereof.

In one or more embodiments, the patient has a proteinuria level of 100 to 1,000 mg/24 hr prior to initiating the administration of the migalastat or salt thereof.

In one or more embodiments, the patient has a proteinuria level of greater than 1,000 mg/24 hr prior to initiating the administration of the migalastat or salt thereof.

In one or more embodiments, the migalastat or salt thereof enhances α-Gal A activity.

In one or more embodiments, the effective amount is about 123 mg FBE.

In one or more embodiments, the effective amount is about 123 mg of migalastat free base.

In one or more embodiments, the salt of migalastat is migalastat hydrochloride.

In one or more embodiments, the effective amount is about 150 mg of migalastat hydrochloride.

In one or more embodiments, the migalastat or salt thereof is in an oral dosage form. In one or more embodiments, the oral dosage form comprises a tablet, a capsule or a solution.

In one or more embodiments, the migalastat or salt thereof is administered for at least 28 days.

In one or more embodiments, the migalastat or salt thereof is administered for at least 6 months.

In one or more embodiments, the migalastat or salt thereof is administered for at least 12 months.

In one or more embodiments, administration of the effective amount of the migalastat or salt thereof to a group of ERT-naïve patients having moderate renal impairment provides a mean reduction of plasma lyso-Gb$_3$ of at least about 5 nmol/L after 24 months of the administration of the migalastat or salt thereof.

Another aspect of the present invention pertains to the use of migalastat to reduce LVMi in a patient diagnosed with Fabry disease and having renal impairment. In various embodiments, the method comprises administering to the patient about 100 mg to about 150 mg FBE of migalastat or salt thereof at a frequency of once every other day.

In one or more embodiments, the patient has mild or moderate renal impairment.

In one or more embodiments, the patient has mild renal impairment.

In one or more embodiments, the patient has moderate renal impairment.

In one or more embodiments, the patient has severe renal impairment.

In one or more embodiments, the patient is an ERT-experienced patient.

In one or more embodiments, the patient is an ERT-naïve patient.

In one or more embodiments, the patient has a proteinuria level of less than 100 mg/24 hr prior to initiating the administration of the migalastat or salt thereof.

In one or more embodiments, the patient has a proteinuria level of 100 to 1,000 mg/24 hr prior to initiating the administration of the migalastat or salt thereof.

In one or more embodiments, the patient has a proteinuria level of greater than 1,000 mg/24 hr prior to initiating the administration of the migalastat or salt thereof.

In one or more embodiments, the migalastat or salt thereof enhances α-Gal A activity.

In one or more embodiments, the effective amount is about 123 mg FBE.

In one or more embodiments, the effective amount is about 123 mg of migalastat free base.

In one or more embodiments, the salt of migalastat is migalastat hydrochloride.

In one or more embodiments, the effective amount is about 150 mg of migalastat hydrochloride.

In one or more embodiments, the migalastat or salt thereof is in an oral dosage form. In one or more embodiments, the oral dosage form comprises a tablet, a capsule or a solution.

In one or more embodiments, the migalastat or salt thereof is administered for at least 28 days.

In one or more embodiments, the migalastat or salt thereof is administered for at least 6 months.

In one or more embodiments, the migalastat or salt thereof is administered for at least 12 months.

In one or more embodiments, administration of the effective amount of the migalastat or salt thereof to a group of ERT-naïve patients having moderate renal impairment provides a mean reduction of LVMi of at least about 2 g/m$^2$ after 24 months of the administration of the migalastat or salt thereof.

In one or more embodiments, administration of the effective amount of the migalastat or salt thereof to a group of ERT-experienced patients having moderate renal impairment provides a mean reduction of LVMi of at least about 2 g/m$^2$ after 18 months of the administration of the migalastat or salt thereof.

Another aspect of the present invention pertains to the use of migalastat to increase WBC α-Gal A activity in a patient diagnosed with Fabry disease and having renal impairment. In various embodiments, the method comprises administering to the patient about 100 mg to about 150 mg FBE of migalastat or salt thereof at a frequency of once every other day.

In one or more embodiments, the patient has mild or moderate renal impairment.

In one or more embodiments, the patient has mild renal impairment.

In one or more embodiments, the patient has moderate renal impairment.

In one or more embodiments, the patient has severe renal impairment.

In one or more embodiments, the patient is an ERT-experienced patient.

In one or more embodiments, the patient is an ERT-naïve patient.

In one or more embodiments, the patient has a proteinuria level of less than 100 mg/24 hr prior to initiating the administration of the migalastat or salt thereof.

In one or more embodiments, the patient has a proteinuria level of 100 to 1,000 mg/24 hr prior to initiating the administration of the migalastat or salt thereof.

In one or more embodiments, the patient has a proteinuria level of greater than 1,000 mg/24 hr prior to initiating the administration of the migalastat or salt thereof.

In one or more embodiments, the effective amount is about 123 mg FBE.

In one or more embodiments, the effective amount is about 123 mg of migalastat free base.

In one or more embodiments, the salt of migalastat is migalastat hydrochloride.

In one or more embodiments, the effective amount is about 150 mg of migalastat hydrochloride.

In one or more embodiments, the migalastat or salt thereof is in an oral dosage form. In one or more embodiments, the oral dosage form comprises a tablet, a capsule or a solution.

In one or more embodiments, the migalastat or salt thereof is administered for at least 28 days.

In one or more embodiments, the migalastat or salt thereof is administered for at least 6 months.

In one or more embodiments, the migalastat or salt thereof is administered for at least 12 months.

In one or more embodiments, administration of the effective amount of the migalastat or salt thereof to a group of ERT-naïve patients having moderate renal impairment provides a mean increase in WBC α-Gal A activity of at least about 1 4 MU/hr/mg after 24 months of the administration of the migalastat or salt thereof.

In one or more embodiments, administration of the effective amount of the migalastat or salt thereof to a group of ERT-experienced patients having moderate renal impairment provides a mean increase in WBC α-Gal A activity of at least about 1 4 MU/hr/mg after 18 months of the administration of the migalastat or salt thereof.

Another aspect of the present invention pertains to the use of migalastat to stabilize renal function in a patient diagnosed with Fabry disease and having elevated proteinuria. In various embodiments, the method comprises administering to the patient about 100 mg to about 150 mg FBE of migalastat or salt thereof at a frequency of once every other day.

In one or more embodiments, the patient has mild or moderate renal impairment.

In one or more embodiments, the patient has mild renal impairment.

In one or more embodiments, the patient has moderate renal impairment.

In one or more embodiments, the patient has severe renal impairment.

In one or more embodiments, the patient is an ERT-experienced patient.

In one or more embodiments, the patient is an ERT-naïve patient.

In one or more embodiments, the patient has a proteinuria level of 100 to 1,000 mg/24 hr prior to initiating the administration of the migalastat or salt thereof.

In one or more embodiments, the patient has a proteinuria level of greater than 1,000 mg/24 hr prior to initiating the administration of the migalastat or salt thereof.

In one or more embodiments, the migalastat or salt thereof enhances α-Gal A activity.

In one or more embodiments, the effective amount is about 123 mg FBE.

In one or more embodiments, the effective amount is about 123 mg of migalastat free base.

In one or more embodiments, the salt of migalastat is migalastat hydrochloride.

In one or more embodiments, the effective amount is about 150 mg of migalastat hydrochloride.

In one or more embodiments, the migalastat or salt thereof is in an oral dosage form. In one or more embodiments, the oral dosage form comprises a tablet, a capsule or a solution.

In one or more embodiments, the migalastat or salt thereof is administered for at least 28 days.

In one or more embodiments, the migalastat or salt thereof is administered for at least 6 months.

In one or more embodiments, the migalastat or salt thereof is administered for at least 12 months.

In one or more embodiments, administration of the effective amount of the migalastat or salt thereof to a group of patients having a proteinuria level of 100 to 1,000 mg/24 hr prior to initiating the administration of the migalastat or salt thereof provides a mean annualized rate of change in $eGFR_{CKD-EPI}$ of greater than −2.0 mL/min/1.73 m2.

In one or more embodiments, administration of the effective amount of the migalastat or salt thereof to a group of patients having a proteinuria level of greater than 1,000 mg/24 hr prior to initiating the administration of the migalastat or salt thereof provides a mean annualized rate of change in $eGFR_{CKD-EPI}$ of greater than −5.0 mL/min/1.73 m$^2$.

Another aspect of the present invention pertains to a method for the treatment of Fabry disease in a patient having elevated proteinuria, the method comprising administering to the patient an effective amount of migalastat or salt thereof at a frequency of once every other day. In one or more embodiments, the effective amount is about 100 mg to about 150 mg FBE.

In one or more embodiments, the patient has mild or moderate renal impairment.

In one or more embodiments, the patient has mild renal impairment.

In one or more embodiments, the patient has moderate renal impairment.

In one or more embodiments, the patient has severe renal impairment.

In one or more embodiments, the patient is an ERT-experienced patient.

In one or more embodiments, the patient is an ERT-naïve patient.

In one or more embodiments, the patient has a proteinuria level of 100 to 1,000 mg/24 hr prior to initiating the administration of the migalastat or salt thereof.

In one or more embodiments, the patient has a proteinuria level of greater than 1,000 mg/24 hr prior to initiating the administration of the migalastat or salt thereof.

In one or more embodiments, the migalastat or salt thereof enhances α-Gal A activity.

In one or more embodiments, the effective amount is about 123 mg FBE.

In one or more embodiments, the effective amount is about 123 mg of migalastat free base.

In one or more embodiments, the salt of migalastat is migalastat hydrochloride.

In one or more embodiments, the effective amount is about 150 mg of migalastat hydrochloride.

In one or more embodiments, the migalastat or salt thereof is in an oral dosage form. In one or more embodiments, the oral dosage form comprises a tablet, a capsule or a solution.

In one or more embodiments, the migalastat or salt thereof is administered for at least 28 days.

In one or more embodiments, the migalastat or salt thereof is administered for at least 6 months.

In one or more embodiments, the migalastat or salt thereof is administered for at least 12 months.

In one or more embodiments, administration of the effective amount of the migalastat or salt thereof to a group of patients having a proteinuria level of 100 to 1,000 mg/24 hr prior to initiating the administration of the migalastat or salt thereof provides a mean annualized rate of change in $eGFR_{CKD-EPI}$ of greater than −2.0 mL/min/1.73 m2.

In one or more embodiments, administration of the effective amount of the migalastat or salt thereof to a group of patients having a proteinuria level of greater than 1,000 mg/24 hr prior to initiating the administration of the migalastat or salt thereof provides a mean annualized rate of change in $eGFR_{CKD-EPI}$ of greater than −5.0 mL/min/1.73 $m^2$.

Various embodiments are listed below. It will be understood that the embodiments listed below may be combined not only as listed below, but in other suitable combinations in accordance with the scope of the invention.

BRIEF DESCRIPTION OF THE DRAWINGS

FIGS. 9A-D show $C_{max}$, AUC, $C_{min}$ and $C_{48}$, respectively, for normal, mild, moderate and severe renal impairment subjects;

FIG. 14A-E show the full DNA sequence of human wild type GLA gene (SEQ ID NO: 1); and FIG. 15 shows the wild type GLA protein (SEQ ID NO: 2).

DETAILED DESCRIPTION

Figure 1A:
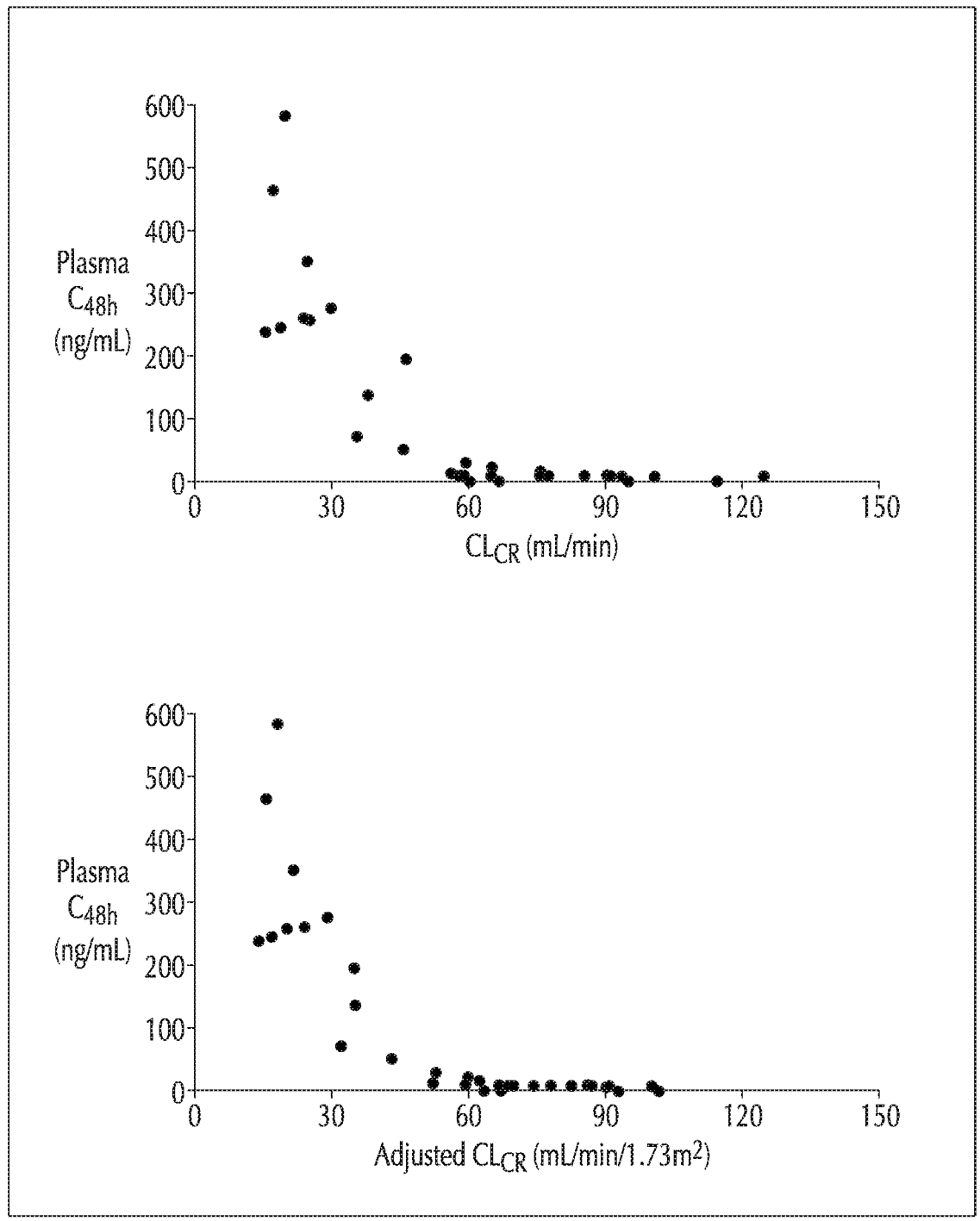
FIG. 1A shows the migalastat plasma concentrations for non-Fabry patients with varying degrees of renal impairment as a function of $CL_{CR}$.

Before describing several exemplary embodiments of the invention, it is to be understood that the invention is not limited to the details of construction or process steps set forth in the following description. The invention is capable of other embodiments and of being practiced or being carried out in various ways.

It has surprisingly been discovered that migalastat therapy stabilizes renal function, reduces LVMi, reduces plasma lyso-$Gb_3$ and increases WBC α-Gal A activity in Fabry patients with mild and moderate renal impairment. Accordingly, various aspects of the present invention pertain to particular dosing regimens of migalastat for Fabry patients having renal impairment. Migalastat is a pharmacological chaperone used in the treatment of Fabry disease. This pharmacological chaperone is usually cleared from the body by the kidneys. However, patients who have renal impairment (a common problem for Fabry patients) may not be able to clear the migalastat from the body, and it was not previously known how patients with both Fabry disease and renal impairment would respond to migalastat therapy. Because pharmacological chaperones are also inhibitors, balancing the enzyme-enhancing and inhibitory effects of pharmacological chaperones such as migalastat is very difficult. Moreover, due to the complex interactions between Fabry disease and renal function, and the lack of knowledge on the role of a pharmacological chaperone, migalastat dosing for Fabry patients with renal impairment is difficult to ascertain without significant clinical data and/or computer modeling.

Accordingly, aspects of the present invention pertain to methods of treating Fabry patients having renal impairment and/or elevated proteinuria using migalastat or a salt thereof, such as by stabilizing renal function, reducing LVMi, reducing plasma lyso-$Gb_3$ and/or increasing α-Gal A activity in the patient.

In one or more embodiments, the method comprises administering to the patient about 100 mg to about 150 mg FBE of migalastat or salt thereof at a frequency of once every other day. The patient may have mild, moderate or severe renal impairment. In one or more embodiments, the patient has mild or moderate renal impairment. In specific embodiments, the patient has mild renal impairment. In other specific embodiments, the patient has moderate renal impairment.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Fabry disease" refers to an X-linked inborn error of glycosphingolipid catabolism due to deficient lysosomal α-Gal A activity. This defect causes accumulation of the substrate globotriaosylceramide ("GL-3", also known as $Gb_3$ or ceramide trihexoside) and related glycosphingolipids in vascular endothelial lysosomes of the heart, kidneys, skin, and other tissues. Another substrate of the enzyme is plasma globotriaosylsphingosine ("plasma lyso-$Gb_3$").

A "carrier" is a female who has one X chromosome with a defective α-Gal A gene and one X chromosome with the normal gene and in whom X chromosome inactivation of the normal allele is present in one or more cell types. A carrier is often diagnosed with Fabry disease.

A "patient" refers to a subject who has been diagnosed with or is suspected of having a particular disease. The patient may be human or animal.

A "Fabry patient" refers to an individual who has been diagnosed with or suspected of having Fabry disease and has a mutated α-Gal A as defined further below. Characteristic markers of Fabry disease can occur in male hemizygotes and female carriers with the same prevalence, although females typically are less severely affected.

The term "ERT-naïve patient" refers to a Fabry patient that has never received ERT or has not received ERT for at least 6 months prior to initiating migalastat therapy.

The term "ERT-experienced patient" refers to a Fabry patient that was receiving ERT immediately prior to initiating migalastat therapy. In some embodiments, the ERT-experienced patient has received at least 12 months of ERT immediately prior to initiating migalastat therapy.

Human α-galactosidase A (α-Gal A) refers to an enzyme encoded by the human GLA gene. The full DNA sequence of α-Gal A, including introns and exons, is available in GenBank Accession No. X14448.1 and shown in SEQ ID NO: 1 and FIGS. 14A-E. The human α-Gal A enzyme consists of 429 amino acids and is available in GenBank Accession Nos. X14448.1 and U78027.1 and shown in SEQ ID NO: 2 and FIG. 15.

The term "mutant protein" includes a protein which has a mutation in the gene encoding the protein which results in the inability of the protein to achieve a stable conformation under the conditions normally present in the ER. The failure to achieve a stable conformation results in a substantial amount of the enzyme being degraded, rather than being transported to the lysosome. Such a mutation is sometimes called a "conformational mutant." Such mutations include, but are not limited to, missense mutations, and in-frame small deletions and insertions.

As used herein in one embodiment, the term "mutant α-Gal A" includes an α-Gal A which has a mutation in the gene encoding α-Gal A which results in the inability of the enzyme to achieve a stable conformation under the conditions normally present in the ER. The failure to achieve a stable conformation results in a substantial amount of the enzyme being degraded, rather than being transported to the lysosome.

As used herein, the term "specific pharmacological chaperone" ("SPC") or "pharmacological chaperone" ("PC") refers to any molecule including a small molecule, protein, peptide, nucleic acid, carbohydrate, etc. that specifically binds to a protein and has one or more of the following effects: (i) enhances the formation of a stable molecular conformation of the protein; (ii) induces trafficking of the protein from the ER to another cellular location, preferably a native cellular location, i.e., prevents ER-associated degradation of the protein; (iii) prevents aggregation of misfolded proteins; and/or (iv) restores or enhances at least partial wild-type function and/or activity to the protein. A compound that specifically binds to e.g., α-Gal A, means that it binds to and exerts a chaperone effect on the enzyme and not a generic group of related or unrelated enzymes. More specifically, this term does not refer to endogenous chaperones, such as BiP, or to non-specific agents which have demonstrated non-specific chaperone activity against various proteins, such as glycerol, DMSO or deuterated water, i.e., chemical chaperones. In one or more embodiments of the present invention, the PC may be a reversible competitive inhibitor.

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

As used herein, the term "specifically binds" refers to the interaction of a pharmacological chaperone with a protein such as α-Gal A, specifically, an interaction with amino acid residues of the protein that directly participate in contacting the pharmacological chaperone. A pharmacological chaperone specifically binds a target protein, e.g., α-Gal A, to exert a chaperone effect on the protein and not a generic group of related or unrelated proteins. The amino acid residues of a protein that interact with any given pharmacological chaperone may or may not be within the protein's "active site." Specific binding can be evaluated through routine binding assays or through structural studies, e.g., co-crystallization, NMR, and the like. The active site for α-Gal A is the substrate binding site.

"Deficient α-Gal A activity" refers to α-Gal A activity in cells from a patient which is below the normal range as compared (using the same methods) to the activity in normal individuals not having or suspected of having Fabry or any other disease (especially a blood disease).

As used herein, the terms "enhance α-Gal A activity" or "increase α-Gal A activity" refer to increasing the amount of α-Gal A that adopts a stable conformation in a cell contacted with a pharmacological chaperone specific for the α-Gal A, relative to the amount in a cell (preferably of the same cell-type or the same cell, e.g., at an earlier time) not contacted with the pharmacological chaperone specific for the α-Gal A. This term also refers to increasing the trafficking of α-Gal A to the lysosome in a cell contacted with a pharmacological chaperone specific for the α-Gal A, relative to the trafficking of α-Gal A not contacted with the pharmacological chaperone specific for the protein. These terms refer to both wild-type and mutant α-Gal A. In one embodiment, the increase in the amount of α-Gal A in the cell is measured by measuring the hydrolysis of an artificial substrate in lysates from cells that have been treated with the PC. An increase in hydrolysis is indicative of increased α-Gal A activity.

The term "α-Gal A activity" refers to the normal physiological function of a wild-type α-Gal A in a cell. For example, α-Gal A activity includes hydrolysis of GL-3.

A "responder" is an individual diagnosed with or suspected of having a lysosomal storage disorder, such, for example Fabry disease, whose cells exhibit sufficiently increased α-Gal A activity, respectively, and/or amelioration of symptoms or enhancement in surrogate markers, in response to contact with a PC. Non-limiting examples of enhancements in surrogate markers for Fabry are lyso-Gb$_3$ and those disclosed in U.S. Patent Application Publication No. US 2010/0113517, which is hereby incorporated by reference in its entirety.

Non-limiting examples of improvements in surrogate markers for Fabry disease disclosed in US 2010/0113517 include increases in α-Gal A levels or activity in cells (e.g., fibroblasts) and tissue; reductions in of GL-3 accumulation; decreased plasma concentrations of homocysteine and vascular cell adhesion molecule-1 (VCAM-1); decreased GL-3 accumulation within myocardial cells and valvular fibrocytes; reduction in plasma lyso-Gb$_3$; reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin; the absence of laminated inclusion bodies (Zebra bodies) in glomerular epithelial cells; improvements in renal function; mitigation of hypohidrosis; the absence of angiokeratomas; and improvements hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities). Another type of clinical marker that can be assessed for Fabry disease is the prevalence of deleterious cardiovascular manifestations. Common cardiac-related signs and symptoms of Fabry disease include left ventricular hypertrophy, valvular disease (especially mitral valve prolapse and/or regurgitation), premature coronary artery disease, angina, myocardial infarction, conduction abnormalities, arrhythmias, congestive heart failure.

As used herein, the phrase "stabilizing renal function" and similar terms, among others things, refer to reducing decline in renal function and/or restoring renal function. As untreated Fabry patients are expected to have significant decreases in renal function, improvements in the rate of renal function deterioration and/or improvements in renal function demonstrate a benefit of migalastat therapy as described herein. In particular, stabilizing renal function may manifest in a Fabry patient, regardless of the severity of kidney function and whether ERT-naïve or experienced, by improving renal function or delaying the rate of renal function deterioration when compared to an analogous patient not treated with a therapy of the present invention, for example, as much as 0.2 mL/min/1.73 m$^2$ for one particular patient population. An advantage of the method of treatment disclosed herein compared to non-treatment (no chaperone or ERT-treatment) or ERT-treatment is that Fabry patients treated with the present invention exhibit less or no decline in his or her renal function. For example, improvements may be observed with ERT-treatment initially but the renal function of ERT-treated patients experiences a precipitous decline after the initial two or three years of the therapy—similar to the degree of decline observed prior to ERT-treatment. In contrast, the therapy described herein clears lysosomal GL-3 more efficiently and has been shown to elicit improvement in patients (e.g., see Example 5) not expected to improve, for example, in an ERT-experienced patient. Clinical data to date using the therapy described herein is expected to deliver continued improvements in patient outcomes even after two years post-treatment. Thus, in some embodiments, a patient treated with the therapy described herein continues to stabilize renal function for more than two years after treatment (e.g., by improving a glomerular filtration rate (GFR) or delaying the rate of decline of a GFR in the patient).

"Renal impairment" refers to a patient having a GFR less than 90 mL/min/1.73 m$^2$. Two of the most commonly used equations for calculating an estimated glomerular filtration rate (eGFR) from serum creatinine are the Chronic Kidney Disease Epidemiology Collaboration (CKD-EPI) equation and the Modification of Diet in Renal Disease (MDRD), which are referred to as eGFR$_{CKD-EPI}$ and eGFR$_{MDRD}$, respectively. The severity of chronic kidney disease has been defined in six stages:
  a. (Stage 0) Normal kidney function—GFR above 90 mL/min/1.73 m$^2$ and no proteinuria;
  b. (Stage 1)—GFR above 90 mL/min/1.73 m$^2$ with evidence of kidney damage;
  c. (Stage 2) (mild)—GFR of 60 to 89 mL/min/1.73 m$^2$ with evidence of kidney damage;
  d. (Stage 3) (moderate)—GFR of 30 to 59 mL/min/1.73 m$^2$;
  e. (Stage 4) (severe)—GFR of 15 to 29 mL/min/1.73 m$^2$;
  f. (Stage 5) kidney failure—GFR less than 15 mL/min/1.73 m$^2$.

"Elevated proteinuria" refers to urine protein levels that are above the normal range. The normal range for urine protein is 0-150 mg per day, so elevated proteinuria is urine protein levels about 150 mg per day.

As used herein, the phrase "stabilize plasma lyso-Gb$_3$" and similar terms refer to reducing the increase in plasma lyso-Gb$_3$ and/or reducing plasma lyso-Gb$_3$. As untreated Fabry patients are expected to have significant increases in plasma lyso-Gb$_3$, improvements in the rate of plasma lyso-Gb$_3$ accumulation and/or improvements in plasma lyso-Gb$_3$ demonstrate a benefit of migalastat therapy as described herein.

The dose that achieves one or more of the aforementioned responses is a "therapeutically effective dose."

The phrase "pharmaceutically acceptable" refers to molecular entities and compositions that are physiologically tolerable and do not typically produce untoward reactions when administered to a human. In some embodiments, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" in reference to a pharmaceutical carrier refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

The term "enzyme replacement therapy" or "ERT" refers to the introduction of a non-native, purified enzyme into an individual having a deficiency in such enzyme. The administered protein can be obtained from natural sources or by recombinant expression (as described in greater detail below). The term also refers to the introduction of a purified enzyme in an individual otherwise requiring or benefiting from administration of a purified enzyme, e.g., suffering from enzyme insufficiency. The introduced enzyme may be a purified, recombinant enzyme produced in vitro, or protein purified from isolated tissue or fluid, such as, e.g., placenta or animal milk, or from plants.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

As used herein, the term "free base equivalent" or "FBE" refers to the amount of migalastat present in the migalastat or salt thereof. In other words, the term "FBE" means either an amount of migalastat free base, or the equivalent amount of migalastat free base that is provided by a salt of migalastat. For example, due to the weight of the hydrochloride salt, 150 mg of migalastat hydrochloride only provides as much migalastat as 123 mg of the free base form of migalastat. Other salts are expected to have different conversion factors, depending on the molecular weight of the salt.

The term "migalastat" encompasses migalastat free base or a pharmaceutically acceptable salt thereof (e.g., migalastat HCl), unless specifically indicated to the contrary.

Fabry Disease

Fabry disease is a rare, progressive and devastating X-linked lysosomal storage disorder. Mutations in the GLA gene result in a deficiency of the lysosomal enzyme, α-Gal A, which is required for glycosphingolipid metabolism. Beginning early in life, the reduction in α-Gal A activity results in an accumulation of glycosphingolipids, including GL-3 and plasma lyso-Gb$_3$, and leads to the symptoms and life-limiting sequalae of Fabry disease, including pain, gastrointestinal symptoms, renal failure, cardiomyopathy, cerebrovascular events, and early mortality. Early initiation of therapy and lifelong treatment provide an opportunity to slow disease progression and prolong life expectancy.

Fabry disease encompasses a spectrum of disease severity and age of onset, although it has traditionally been divided into 2 main phenotypes, "classic" and "late-onset". The classic phenotype has been ascribed primarily to males with undetectable to low α-Gal A activity and earlier onset of renal, cardiac and/or cerebrovascular manifestations. The late-onset phenotype has been ascribed primarily to males with higher residual α-Gal A activity and later onset of these disease manifestations. Heterozygous female carriers typically express the late-onset phenotype but depending on the pattern of X-chromosome inactivation may also display the classic phenotype.

More than 800 Fabry disease-causing GLA mutations have been identified.

Approximately 60% are missense mutations, resulting in single amino acid substitutions in the α-Gal A enzyme. Missense GLA mutations often result in the production of abnormally folded and unstable forms of α-Gal A and the majority are associated with the classic phenotype. Normal cellular quality control mechanisms in the endoplasmic reticulum block the transit of these abnormal proteins to lysosomes and target them for premature degradation and elimination. Many missense mutant forms are targets for migalastat, an α-Gal A—specific pharmacological chaperone.

The clinical manifestations of Fabry disease span a broad spectrum of severity and roughly correlate with a patient's residual α-GAL levels. The majority of currently treated patients are referred to as classic Fabry disease patients, most of whom are males. These patients experience disease of various organs, including the kidneys, heart and brain, with disease symptoms first appearing in adolescence and typically progressing in severity until death in the fourth or fifth decade of life. A number of recent studies suggest that there are a large number of undiagnosed males and females that have a range of Fabry disease symptoms, such as impaired cardiac or renal function and strokes, that usually first appear in adulthood. Individuals with this type of Fabry disease, referred to as late-onset Fabry disease, tend to have higher residual α-GAL levels than classic Fabry disease patients. Individuals with late-onset Fabry disease typically first experience disease symptoms in adulthood, and often have disease symptoms focused on a single organ, such as enlargement of the left ventricle or progressive kidney failure. In addition, late-onset Fabry disease may also present in the form of strokes of unknown cause.

Fabry patients have progressive kidney impairment, and untreated patients exhibit end-stage renal impairment by the fifth decade of life. Deficiency in α-Gal A activity leads to accumulation of GL-3 and related glycosphingolipids in many cell types including cells in the kidney. GL-3 accumulates in podocytes, epithelial cells and the tubular cells of the distal tubule and loop of Henle. Impairment in kidney function can manifest as proteinuria and reduced glomerular filtration rate.

Because Fabry disease can cause progressive worsening in renal function, it is important to understand the pharmacokinetics (PK) of potential therapeutic agents in individuals with renal impairment and particularly so for therapeutic agents that are predominantly cleared by renal excretion. Impairment of renal function may lead to accumulation of the therapeutic agent to levels that become toxic.

Because Fabry disease is rare, involves multiple organs, has a wide age range of onset, and is heterogeneous, proper diagnosis is a challenge. Awareness is low among health care professionals and misdiagnoses are frequent. Diagnosis of Fabry disease is most often confirmed on the basis of decreased α-Gal A activity in plasma or peripheral leukocytes (WBCs) once a patient is symptomatic, coupled with mutational analysis. In females, diagnosis is even more challenging since the enzymatic identification of carrier females is less reliable due to random X-chromosomal inactivation in some cells of carriers. For example, some obligate carriers (daughters of classically affected males) have α-Gal A enzyme activities ranging from normal to very low activities. Since carriers can have normal α-Gal A enzyme activity in leukocytes, only the identification of an α-Gal A mutation by genetic testing provides precise carrier identification and/or diagnosis.

Mutant forms of α-galactosidase A considered to be amenable to migalastat are defined as showing a relative increase (+10 μM migalastat) of ≥1.20-fold and an absolute increase (+10 μM migalastat) of ≥3.0% wild-type when the mutant form of α-galactosidase A is expressed in HEK-293 cells (referred to as the "HEK assay") according to Good Laboratory Practice (GLP)-validated in vitro assay (GLP HEK or Migalastat Amenability Assay). Such mutations are also referred to herein as "HEK assay amenable" mutations.

Previous screening methods have been provided that assess enzyme enhancement prior to the initiation of treatment. For example, an assay using HEK-293 cells has been utilized in clinical trials to predict whether a given mutation will be responsive to pharmacological chaperone (e.g., migalastat) treatment. In this assay, cDNA constructs are created. The corresponding α-Gal A mutant forms are transiently expressed in HEK-293 cells. Cells are then incubated±migalastat (17 nM to 1 mM) for 4 to 5 days. After, α-Gal A levels are measured in cell lysates using a synthetic fluorogenic substrate (4-MU-α-Gal) or by western blot. This has been done for known disease-causing missense or small in-frame insertion/deletion mutations. Mutations that have previously been identified as responsive to a PC (e.g. migalastat) using these methods are listed in U.S. Pat. No. 8,592,362, which is hereby incorporated by reference in its entirety.

Pharmacological Chaperones

The binding of small molecule inhibitors of enzymes associated with LSDs can increase the stability of both mutant enzyme and the corresponding wild-type enzyme (see U.S. Pat. Nos. 6,274,597; 6,583,158; 6,589,964; 6,599,919; 6,916,829; and 7,141,582 all incorporated herein by reference). In particular, administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. The original theory behind this strategy was as follows: since the mutant enzyme protein is unstable in the ER (Ishii et al., Biochem. Biophys. Res. Comm. 1996; 220: 812-815), the enzyme protein is retarded in the normal transport pathway (ER→Golgi apparatus→endosomes→lysosome) and prematurely degraded. Therefore, a compound which binds to and increases the stability of a mutant enzyme, may serve as a "chaperone" for the enzyme and increase the amount that can exit the ER and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the ER and be trafficked to lysosomes.

In one or more embodiments, the pharmacological chaperone comprises migalastat or a salt thereof. The compound migalastat, also known as 1-deoxygalactonojirimycin (1-DGJ) or (2R,3S,4R,5S)-2-(hydroxymethyl) piperdine-3,4,5-triol is a compound having the following chemical formula:

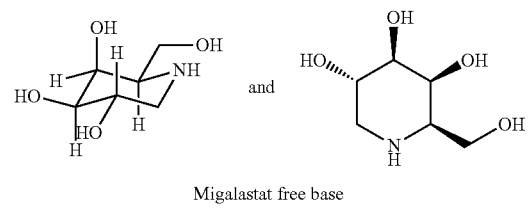 [SMILES: OCC1NCC(O)C(O)C1O ; OC[C@H]1NC[C@H](O)[C@@H](O)[C@H]1O]

Migalastat free base

As discussed herein, pharmaceutically acceptable salts of migalastat may also be used in the present invention. When a salt of migalastat is used, the dosage of the salt will be adjusted so that the dose of migalastat received by the patient is equivalent to the amount which would have been received had the migalastat free base been used. One example of a pharmaceutically acceptable salt of migalastat is migalastat HCl:

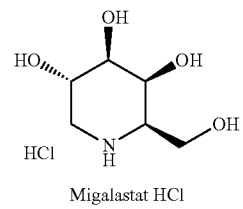 [SMILES: OC[C@H]1NC[C@H](O)[C@@H](O)[C@H]1O ; Cl]

Migalastat HCl

Migalastat is a low molecular weight iminosugar and is an analogue of the terminal galactose of GL-3. In vitro and in vivo pharmacologic studies have demonstrated that migalastat acts as a pharmacological chaperone, selectively and reversibly binding, with high affinity, to the active site of wild-type α-Gal A and specific mutant forms of α-Gal A, the genotypes of which are referred to as HEK assay amenable mutations. Migalastat binding stabilizes these mutant forms of α-Gal A in the endoplasmic reticulum facilitating their proper trafficking to lysosomes where dissociation of migalastat allows α-Gal A to reduce the level of GL-3 and other substrates. Approximately 30-50% of patients with Fabry disease have HEK assay amenable mutations; the majority of which are associated with the classic phenotype of the disease. A list of HEK assay amenable mutations includes at least those mutations listed in Table 1 below. In one or more embodiments, if a double mutation is present on the same chromosome (males and females), that patient is considered HEK assay amenable if the double mutation is present in one entry in Table 1 (e.g., D55V/Q57L). In some embodiments, if a double mutation is present on different chromosomes (only in females) that patient is considered HEK assay amenable if either one of the individual mutations is present in Table 1. In addition to Table 1 below, HEK assay amenable mutations can also be found in the summary of product characteristics and/or prescribing information for GALAFOLD™ in various countries in which GALAFOLD™ is approved for use, or at the website www.galafoldamenabilitytable.com, each of which is hereby incorporated by reference in its entirety.

TABLE 1

| Nucleotide change | Nucleotide change | Protein sequence change |
| --- | --- | --- |
| c.7C > G | c.C7G | L3V |
| c.8T > C | c.T8C | L3P |
| c.[11G > T; 620A > C] | c.G11T/A620C | R4M/Y207S |
| c.37G > A | c.G37A | A13T |
| c.37G > C | c.G37C | A13P |
| c.43G > A | c.G43A | A15T |
| c.44C > G | c.C44G | A15G |
| c.53T > G | c.T53G | F18C |
| c.58G > C | c.G58C | A20P |
| c.59C > A | c.C59A | A20D |
| c.70T > C or c.70T > A | c.T70C or c.T70A | W24R |
| c.70T > G | c.T70G | W24G |
| c.72G > C or c.72G > T | c.G72C or c.G72T | W24C |
| c.95T > C | c.T95C | L32P |
| c.97G > T | c.G97T | D33Y |
| c.98A > G | c.A98G | D33G |
| c.100A > G | c.A100G | N34D |
| c.101A > C | c.A101C | N34T |
| c.101A > G | c.A101G | N34S |
| c.102T > G or c.102T > A | c.T102G or c.T102A | N34K |
| c.103G > C or c.103G > A | c.G103C or c.G103A | G35R |
| c.104G > A | c.G104A | G35E |
| c.104G > T | c.G104T | G35V |
| c.107T > C | c.T107C | L36S |
| c.107T > G | c.T107G | L36W |
| c.108G > C or c.108G > T | c.G108C or c.G108T | L36F |
| c.109G > A | c.G109A | A37T |
| c.110C > T | c.C110T | A37V |
| c.122C > T | c.C122T | T41I |
| c.124A > C or c.124A > T | c.A124C or c.A124T | M42L |
| c.124A > G | c.A124G | M42V |
| c.125T > A | c.T125A | M42K |
| c.125T > C | c.T125C | M42T |
| c.125T > G | c.T125G | M42R |
| c.126G > A or c.126G > C or c.126G > T | c.G126A or c.G126C or c.G126T | M42I |
| c.137A > C | c.A137C | H46P |
| c.142G > C | c.G142C | E48Q |
| c.152T > A | c.T152A | M51K |
| c.153G > A or c.153G > T or c.153G > C | c.G153A or c.G153T or c.G153C | M51I |
| c.157A > G | c.A157G | N53D |
| c.[157A > C; 158A > T] | c.A157C/A158T | N53L |
| c.160C > T | c.C160T | L54F |
| c.161T > C | c.T161C | L54P |
| c.164A > G | c.A164G | D55G |
| c.164A > T | c.A164T | D55V |
| c.[164A > T; 170A > T] | c.A164T/A170T | D55V/Q57L |
| c.167G > T | c.G167T | C56F |
| c.167G > A | c.G167A | C56Y |
| c.170A > T | c.A170T | Q57L |
| c.175G > A | c.G175A | E59K |
| c.178C > A | c.C178A | P60T |
| c.178C > T | c.C178T | P60S |
| c.179C > T | c.C179T | P60L |
| c.196G > A | c.G196A | E66K |
| c.197A > G | c.A197G | E66G |
| c.207C > A or c.207C > G | c.C207A or c.C207G | F69L |
| c.214A > G | c.A214G | M72V |
| c.216G > A or c.216G > T or c.216G > C | c.G216A or c.G216T or c.G216C | M72I |
| c.218C > T | c.C218T | A73V |
| c.227T > C | c.T227C | M76T |
| c.239G > A | c.G239A | G80D |
| c.247G > A | c.G247A | D83N |
| c.253G > A | c.G253A | G85S |
| c.254G > A | c.G254A | G85D |
| c.[253G > A; 254G > A] | c.G253A/G254A | G85N |
| c.[253G > A; 254G > T; 255T > G] | c.G253A/G254T/T255G | G85M |
| c.261G > C or c.261G > T | c.G261C or c.G261T | E87D |
| c.265C > T | c.C265T | L89F |
| c.272T > C | c.T272C | I91T |
| c.288G > A or c.288G > T or c.288G > C | c.G288A or c.G288T or c.G288C | M96I |
| c.289G > C | c.G289C | A97P |
| c.290C > T | c.C290T | A97V |
| c.305C > T | c.C305T | S102L |
| c.311G > T | c.G311T | G104V |

TABLE 1-continued

| Nucleotide change | Nucleotide change | Protein sequence change |
|---|---|---|
| c.316C > T | c.C316T | L106F |
| c.322G > A | c.G322A | A108T |
| c.326A > G | c.A326G | D109G |
| c.334C > G | c.C334G | R112G |
| c.335G > A | c.G335A | R112H |
| c.337T > A | c.T337A | F113I |
| c.337T > C or c.339T > A or c.339T > G | c.T337C or c.T339A or c.T339G | F113L |
| c.352C > T | c.C352T | R118C |
| c.361G > A | c.G361A | A121T |
| c.368A > G | c.A368G | Y123C |
| c.373C > T | c.C373T | H125Y |
| c.374A > T | c.A374T | H125L |
| c.376A > G | c.A376G | S126G |
| c.383G > A | c.G383A | G128E |
| c.399T > G | c.T399G | I133M |
| c.404C > T | c.C404T | A135V |
| c.408T > A or c.408T > G | c.T408A or c.T408G | D136E |
| c.416A > G | c.A416G | N139S |
| c.419A > C | c.A419C | K140T |
| c.427G > A | c.G427A | A143T |
| c.431G > A | c.G431A | G144D |
| c.431G > T | c.G431T | G144V |
| c.434T > C | c.T434C | F145S |
| c.436C > T | c.C436T | P146S |
| c.437C > G | c.C437G | P146R |
| c.454T > C | c.T454C | Y152H |
| c.455A > G | c.A455G | Y152C |
| c.466G > A | c.G466A | A156T |
| c.467C > T | c.C467T | A156V |
| c.471G > C or c.471G > T | c.G471C or c.G471T | Q157H |
| c.484T > G | c.T484G | W162G |
| c.493G > C | c.G493C | D165H |
| c.494A > G | c.A494G | D165G |
| c.[496C > G; 497T > G] | c.C496G/T497G | L166G |
| c.496C > G | c.C496G | L166V |
| c.496_497delinsTC | c.496_497delinsTC | L166S |
| c.499C > G | c.C499G | L167V |
| c.506T > C | c.T506C | F169S |
| c.511G > A | c.G511A | G171S |
| c.520T > C | c.T520C | C174R |
| c.520T > G | c.T520G | C174G |
| c.525C > G or c.525C > A | c.C525G or c.C525A | D175E |
| c.539T > G | c.T539G | L180W |
| c.540G > C | c.G540C | L180F |
| c.548G > C | c.G548C | G183A |
| c.548G > A | c.G548A | G183D |
| c.550T > A | c.T550A | Y184N |
| c.551A > G | c.A551G | Y184C |
| c.553A > G | c.A553G | K185E |
| c.559A > G | c.A559G | M187V |
| c.559_564dup | c.559_564dup | p.M187_S188dup |
| c.560T > C | c.T560C | M187T |
| c.561G > T or c.561G > A or c.561G > C | c.G561T or c.G561A or c.G561C | M187I |
| c.572T > A | c.T572A | L191Q |
| c.581C > T | c.C581T | T194I |
| c.584G > T | c.G584T | G195V |
| c.586A > G | c.A586G | R196G |
| c.593T > C | c.T593C | I198T |
| c.595G > A | c.G595A | V199M |
| c.596T > C | c.T596C | V199A |
| c.596T > G | c.T596G | V199G |
| c.599A > G | c.A599G | Y200C |
| c.602C > T | c.C602T | S201F |
| c.602C > A | c.C602A | S201Y |
| c.608A > T | c.A608T | E203V |
| c.609G > C or c.609G > T | c.G609C or c.G609T | E203D |
| c.613C > A | c.C613A | P205T |
| c.613C > T | c.C613T | P205S |
| c.614C > T | c.C614T | P205L |
| c.619T > C | c.T619C | Y207H |
| c.620A > C | c.A620C | Y207S |
| c.623T > G | c.T623G | M208R |
| c.628C > T | c.C628T | P210S |
| c.629C > T | c.C629T | P210L |
| c.638A > G | c.A638G | K213R |
| c.638A > T | c.A638T | K213M |

TABLE 1-continued

| Nucleotide change | Nucleotide change | Protein sequence change |
| --- | --- | --- |
| c.640C > T | c.C640T | P214S |
| c.641C > T | c.C641T | P214L |
| c.643A > G | c.A643G | N215D |
| c.644A > G | c.A644G | N215S |
| c.644A > T | c.A644T | N215I |
| c.[644A > G; 937G > T] | c.A644G/G937T | N215S/D313Y |
| c.646T > G | c.T646G | Y216D |
| c.647A > G | c.A647G | Y216C |
| c.655A > C | c.A655C | I219L |
| c.656T > A | c.T656A | I219N |
| c.656T > C | c.T656C | I219T |
| c.659G > A | c.G659A | R220Q |
| c.659G > C | c.G659C | R220P |
| c.662A > C | c.A662C | Q221P |
| c.671A > C | c.A671C | N224T |
| c.671A > G | c.A671G | N224S |
| c.673C > G | c.C673G | H225D |
| c.683A > G | c.A683G | N228S |
| c.687T > A or c.687T > G | c.T687A or c.T687G | F229L |
| c.695T > C | c.T695C | I232T |
| c.713G > A | c.G713A | S238N |
| c.716T > C | c.T716C | I239T |
| c.720G > C or c.720G > T | c.G720C or c.G720T | K240N |
| c.724A > G | c.A724G | I242V |
| c.724A > T | c.A724T | I242F |
| c.725T > A | c.T725A | I242N |
| c.725T > C | c.T725C | I242T |
| c.728T > G | c.T728G | L243W |
| c.729G > C or c.729G > T | c.G729C or c.G729T | L243F |
| c.730G > A | c.G730A | D244N |
| c.730G > C | c.G730C | D244H |
| c.733T > G | c.T733G | W245G |
| c.740C > G | c.C740G | S247C |
| c.747C > G or c.747C > A | c.C747G or c.C747A | N249K |
| c.749A > C | c.A749C | Q250P |
| c.749A > G | c.A749G | Q250R |
| c.750G > C | c.G750C | Q250H |
| c.758T > C | c.T758C | I253T |
| c.758T > G | c.T758G | I253S |
| c.760-762delGTT | c.760_762delGTT | p.V254del |
| c.769G > C | c.G769C | A257P |
| c.770C > G | c.C770G | A257G |
| c.772G > C or c.772G > A | c.G772C or c.G772A | G258R |
| c.773G > T | c.G773T | G258V |
| c.776C > G | c.C776G | P259R |
| c.776C > T | c.C776T | P259L |
| c.779G > A | c.G779A | G260E |
| c.779G > C | c.G779C | G260A |
| c.781G > A | c.G781A | G261S |
| c.781G > C | c.G781C | G261R |
| c.781G > T | c.G781T | G261C |
| c.788A > G | c.A788G | N263S |
| c.790G > T | c.G790T | D264Y |
| c.794C > T | c.C794T | P265L |
| c.800T > C | c.T800C | M267T |
| c.805G > A | c.G805A | V269M |
| c.806T > C | c.T806C | V269A |
| c.809T > C | c.T809C | I270T |
| c.810T > G | c.T810G | I270M |
| c.811G > A | c.G811A | G271S |
| c.[811G > A; 937G > T] | c.G811A/G937T | G271S/D313Y |
| c.812G > A | c.G812A | G271D |
| c.823C > G | c.C823G | L275V |
| c.827G > A | c.G827A | S276N |
| c.829T > G | c.T829G | W277G |
| c.831G > T or c.831G > C | c.G831T or c.G831C | W277C |
| c.832A > T | c.A832T | N278Y |
| c.835C > G | c.C835G | Q279E |
| c.838C > A | c.C838A | Q280K |
| c.840A > T or c.840A > C | c.A840T or c.A840C | Q280H |
| c.844A > G | c.A844G | T282A |
| c.845C > T | c.C845T | T282I |
| c.850A > G | c.A850G | M284V |
| c.851T > C | c.T851C | M284T |
| c.860G > T | c.G860T | W287L |
| c.862G > C | c.G862C | A288P |
| c.866T > G | c.T866G | I289S |
| c.868A > C or c.868A > T | c.A868C or c.A868T | M290L |

TABLE 1-continued

| Nucleotide change | Nucleotide change | Protein sequence change |
|---|---|---|
| c.869T > C | c.T869C | M290T |
| c.870G > A or c.870G > C or c.870G > T | c.G870A or c.G870C or c.G870T | M290I |
| c.871G > A | c.G871A | A291T |
| c.877C > A | c.C877A | P293T |
| c.881T > C | c.T881C | L294S |
| c.884T > G | c.T884G | F295C |
| c.886A > G | c.A886G | M296V |
| c.886A > T or c.886A > C | c.A886T or c.A886C | M296L |
| c.887T > C | c.T887C | M296T |
| c.888G > A or c.888G > T or c.888G > C | c.G888A or c.G888T or c.G888C | M296I |
| c.893A > G | c.A893G | N298S |
| c.897C > G or c.897C > A | c.C897G or c.C897A | D299E |
| c.898C > T | c.C898T | L300F |
| c.899T > C | c.T899C | L300P |
| c.901C > G | c.C901G | R301G |
| c.902G > C | c.G902C | R301P |
| c.902G > A | c.G902A | R301Q |
| c.902G > T | c.G902T | R301L |
| c.907A > T | c.A907T | I303F |
| c.908T > A | c.T908A | I303N |
| c.911G > A | c.G911A | S304N |
| c.911G > C | c.G911C | S304T |
| c.919G > A | c.G919A | A307T |
| c.922A > G | c.A922G | K308E |
| c.924A > T or c.924A > C | c.A924T or c.A924C | K308N |
| c.925G > C | c.G925C | A309P |
| c.926C > T | c.C926T | A309V |
| c.928C > T | c.C928T | L310F |
| c.931C > G | c.C931G | L311V |
| c.935A > G | c.A935G | Q312R |
| c.936G > T or c.936G > C | c.G936T or c.G936C | Q312H |
| c.937G > T | c.G937T | D313Y |
| c.[937G > T; 1232G > A] | c.G937T/G1232A | D313Y/G411D |
| c.938A > G | c.A938G | D313G |
| c.946G > A | c.G946A | V316I |
| c.947T > G | c.T947G | V316G |
| c.950T > C | c.T950C | I317T |
| c.955A > T | c.A955T | I319F |
| c.956T > C | c.T956C | I319T |
| c.959A > T | c.A959T | N320I |
| c.962A > G | c.A962G | Q321R |
| c.962A > T | c.A962T | Q321L |
| c.963G > C or c.963G > T | c.G963C or c.G963T | Q321H |
| c.964G > A | c.G964A | D322N |
| c.964G > C | c.G964C | D322H |
| c.966C > A or c.966C > G | c.C966A or c.C966G | D322E |
| c.968C > G | c.C968G | P323R |
| c.973G > A | c.G973A | G325S |
| c.973G > C | c.G973C | G325R |
| c.978G > C or c.978G > T | c.G978C or c.G978T | K326N |
| c.979C > G | c.C979G | Q327E |
| c.980A > T | c.A980T | Q327L |
| c.983G > C | c.G983C | G328A |
| c.989A > G | c.A989G | Q330R |
| c.1001G > A | c.G1001A | G334E |
| c.1010T > C | c.T1010C | F337S |
| c.1012G > A | c.G1012A | E338K |
| c.1016T > A | c.T1016A | V339E |
| c.1027C > A | c.C1027A | P343T |
| c.1028C > T | c.C1028T | P343L |
| c.1033T > C | c.T1033C | S345P |
| c.1046G > C | c.G1046C | W349S |
| c.1055C > G | c.C1055G | A352G |
| c.1055C > T | c.C1055T | A352V |
| c.1061T > A | c.T1061A | I354K |
| c.1066C > G | c.C1066G | R356G |
| c.1066C > T | c.C1066T | R356W |
| c.1067G > A | c.G1067A | R356Q |
| c.1067G > C | c.G1067C | R356P |
| c.1072G > C | c.G1072C | E358Q |
| c.1073A > C | c.A1073C | E358A |
| c.1073A > G | c.A1073G | E358G |
| c.1074G > T or c.1074G > C | c.G1074T or c.G1074C | E358D |
| c.1076T > C | c.T1076C | I359T |
| c.1078G > A | c.G1078A | G360S |
| c.1078G > T | c.G1078T | G360C |

TABLE 1-continued

| Nucleotide change | Nucleotide change | Protein sequence change |
|---|---|---|
| c.1079G > A | c.G1079A | G360D |
| c.1082G > A | c.G1082A | G361E |
| c.1082G > C | c.G1082C | G361A |
| c.1084C > A | c.C1084A | P362T |
| c.1085C > T | c.C1085T | P362L |
| c.1087C > T | c.C1087T | R363C |
| c.1088G > A | c.G1088A | R363H |
| c.1102G > A | c.G1102A | A368T |
| c.1117G > A | c.G1117A | G373S |
| c.1124G > A | c.G1124A | G375E |
| c.1153A > G | c.A1153G | T385A |
| c.1168G > A | c.G1168A | V390M |
| c.1172A > C | c.A1172C | K391T |
| c.1184G > A | c.G1184A | G395E |
| c.1184G > C | c.G1184C | G395A |
| c.1192G > A | c.G1192A | E398K |
| c.1202_1203insGACTTC | c.1202_1203insGACTTC | p.T400_S401dup |
| c.1208T > C | c.T1208C | L403S |
| c.1225C > G | c.C1225G | P409A |
| c.1225C > T | c.C1225T | P409S |
| c.1225C > A | c.C1225A | P409T |
| c.1228A > G | c.A1228G | T410A |
| c.1229C > T | c.C1229T | T410I |
| c.1232G > A | c.G1232A | G411D |
| c.1235C > A | c.C1235A | T412N |
| c.1253A > G | c.A1253G | E418G |
| c.1261A > G | c.A1261G | M421V |

Kidney Function in Fabry Patients

Progressive decline in renal function is a major complication of Fabry disease. For example, patients associated with a classic Fabry phenotype exhibit progressive renal impairment that may eventually require dialysis or renal transplantation.

A frequently used method in the art to assess kidney function is GFR. Generally, the GFR is the volume of fluid filtered from the renal glomerular capillaries into the Bowman's capsule per unit time. Clinically, estimates of GFR are made based upon the clearance of creatinine from serum. GFR can be estimated by collecting urine to determine the amount of creatinine that was removed from the blood over a given time interval. Age, body size and gender may also be factored in. The lower the GFR number, the more advanced kidney damage is.

Some studies indicate that untreated Fabry patients experience an average decline in GFR between 7.0 and 18.9 mL/min/1.73 m² per year, while patients receiving ERT may experience an average decline in GFR between 2.0 and 2.7 mL/min/1.73 m² per year, although more rapid declines may occur in patients with more significant proteinuria or with more severe chronic kidney disease.

An estimated GFR (eGFR) is calculated from serum creatinine using an isotope dilution mass spectrometry (IDMS) traceable equation. Two of the most commonly used equations for estimating glomerular filtration rate (GFR) from serum creatinine are the Chronic Kidney Disease Epidemiology Collaboration (CKD-EPI) equation and the Modification of Diet in Renal Disease (MDRD) Study equation. Both the MDRD Study and CKD-EPI equations include variables for age, gender, and race, which may allow providers to observe that CKD is present despite a serum creatinine concentration that appears to fall within or just above the normal reference interval.

The CKD-EPI equation uses a 2-slope "spline" to model the relationship between GFR and serum creatinine, age, sex, and race. CKD-EPI equation expressed as a single equation:

$$GFR = 141 \times \min(S_{cr}/\kappa, 1)^{\alpha} \times \max(S_{cr}/\kappa, 1)^{-1.209} \times 0.993^{Age} \times 1.018 \text{ [if female]} \times 1.159 \text{ [if black]}$$

where:
$S_{cr}$ is serum creatinine in mg/dL,
$\kappa$ is 0.7 for females and 0.9 for males,
$\alpha$ is −0.329 for females and −0.411 for males,
min indicates the minimum of $S_{cr}/\kappa$ or 1, and
max indicates the maximum of $S_{cr}/\kappa$ or 1.

The following is the IDMS-traceable MDRD Study equation (for creatinine methods calibrated to an IDMS reference method):

$$GFR \text{ (mL/min/1.73 m}^2\text{)} = 175 \times (S_{cr})^{-1.154} \times (Age)^{-0.203} \times (0.742 \text{ if female}) \times (1.212 \text{ if African American})$$

The equation does not require weight or height variables because the results are reported normalized to 1.73 m² body surface area, which is an accepted average adult surface area. The equation has been validated extensively in Caucasian and African American populations between the ages of 18 and 70 with impaired kidney function (eGFR <60 mL/min/1.73 m²) and has shown good performance for patients with all common causes of kidney disease.

One method for estimating the creatinine clearance rate ($eC_{Cr}$) is using the Cockcroft-Gault equation, which in turn estimates GFR in mL/min:

$$\text{Creatinine Clearance (mL/min)} = [(140 - \text{Age}) \times \text{Mass (Kg)}^*] \div 72 \times \text{Serum Creatinine(mg/dL)} [* \text{ multiplied by 0.85 if female}]$$

The Cockcroft-Gault equation is the equation suggested for use by the Food and Drug Administration for renal impairment studies. It is common for the creatinine clearance calculated by the Cockcroft-Gault formula to be normalized for a body surface area of 1.73 m². Therefore, this equation can be expressed as the estimated eGFR in mL/min/1.73 m². The normal range of GFR, adjusted for body surface area, is 100-130 mL/min/1.73 m2 in men and 90-120 mL/min/1.73 m2 in women younger than the age of 40.

The severity of chronic kidney disease has been defined in six stages (see also Table 2): (Stage 0) Normal kidney function—GFR above 90 mL/min/1.73 m² and no proteinuria; (Stage 1)—GFR above 90 mL/min/1.73 m² with evidence of kidney damage; (Stage 2) (mild)—GFR of 60 to 89 mL/min/1.73 m² with evidence of kidney damage; (Stage 3) (moderate)—GFR of 30 to 59 mL/min/1.73 m²; (Stage 4) (severe)—GFR of 15 to 29 mL/min/1.73 m²; (Stage 5) kidney failure—GFR less than 15 mL/min/1.73 m². Table 2 below shows the various kidney disease stages with corresponding GFR levels.

TABLE 2

| Chronic Kidney Disease Stage | GFR level (mL/min/1.73 m²) |
| --- | --- |
| Stage 1 (Normal) | ≥90 |
| Stage 2 (Mild) | 60-89 |
| Stage 3 (Moderate) | 30-59 |
| Stage 4 (Severe) | 15-29 |
| Stage 5 (Kidney Failure) | <15 |

Dosing, Formulation and Administration

One or more of the dosing regimens described herein are particularly suitable for Fabry patients who have some degree of renal impairment. Several studies have investigated using 150 mg of migalastat hydrochloride every other day (QOD) in Fabry patients. One study was a 24-month trial, including a 6-month double-blind, placebo-controlled period, in 67 ERT-naïve patients. Another study was an active-controlled, 18-month trial in 57 ERT-experienced patients with a 12-month open-label extension (OLE). Both studies included patients having an estimated glomerular filtration rate (eGFR) of ≥30 mL/min/1.73 m². Accordingly, both studies included Fabry patients with normal renal function as well as patients with mild and moderate renal impairment, but neither study included patients with severe renal impairment.

The studies of migalastat treatment of Fabry patients established that 150 mg of migalastat hydrochloride every other day slowed the progression of the disease as shown by surrogate markers.

Thus, in one or more embodiments, the Fabry patient is administered migalastat or salt thereof at a frequency of once every other day (also referred to as "QOD"). In various embodiments, the doses described herein pertain to migalastat hydrochloride or an equivalent dose of migalastat or a salt thereof other than the hydrochloride salt. In some embodiments, these doses pertain to the free base of migalastat. In alternate embodiments, these doses pertain to a salt of migalastat. In further embodiments, the salt of migalastat is migalastat hydrochloride. The administration of migalastat or a salt of migalastat is referred to herein as "migalastat therapy".

The effective amount of migalastat or salt thereof can be in the range from about 100 mg FBE to about 150 mg FBE. Exemplary doses include about 100 mg FBE, about 105 mg FBE, about 110 mg FBE, about 115 mg FBE, about 120 mg FBE, about 123 mg FBE, about 125 mg FBE, about 130 mg FBE, about 135 mg FBE, about 140 mg FBE, about 145 mg FBE or about 150 mg FBE.

Again, it is noted that 150 mg of migalastat hydrochloride is equivalent to 123 mg of the free base form of migalastat. Thus, in one or more embodiments, the dose is 150 mg of migalastat hydrochloride or an equivalent dose of migalastat or a salt thereof other than the hydrochloride salt, administered at a frequency of once every other day. As set forth above, this dose is referred to as 123 mg FBE of migalastat. In further embodiments, the dose is 150 mg of migalastat hydrochloride administered at a frequency of once every other day. In other embodiments, the dose is 123 mg of the migalastat free base administered at a frequency of once every other day.

In various embodiments, the effective amount is about 122 mg, about 128 mg, about 134 mg, about 140 mg, about 146 mg, about 150 mg, about 152 mg, about 159 mg, about 165 mg, about 171 mg, about 177 mg or about 183 mg of migalastat hydrochloride.

Accordingly, in various embodiments, migalastat therapy includes administering 123 mg FBE at a frequency of once every other day, such as 150 mg of migalastat hydrochloride every other day.

The administration of migalastat or salt thereof may be for a certain period of time. In one or more embodiments, the migalastat or salt thereof is administered for a duration of at least 28 days, such as at least 30, 60 or 90 days or at least 3, 4, 5, 6, 7, 8, 9, 10, 11, 12, 16, 20, 24, 30 or 36 months or at least 1, 2, 3, 4 or 5 years. In various embodiments, the migalastat therapy is long-term migalastat therapy of at least 6 months, such as at least 6, 7, 8, 9, 10, 11, 12, 16, 20, 24, 30 or 36 months or at least 1, 2, 3, 4 or 5 years.

Administration of migalastat or salt thereof according to the present invention may be in a formulation suitable for any route of administration, but is preferably administered in an oral dosage form such as a tablet, capsule or solution. As one example, the patient is orally administered capsules each containing 150 mg migalastat hydrochloride or an equivalent dose of migalastat or a salt thereof other than the hydrochloride salt.

In some embodiments, the PC (e.g., migalastat or salt thereof) is administered orally. In one or more embodiments, the PC (e.g., migalastat or salt thereof) is administered by injection. The PC may be accompanied by a pharmaceutically acceptable carrier, which may depend on the method of administration.

In one or more embodiments, the PC (e.g., migalastat or salt thereof) is administered as monotherapy, and can be in a form suitable for any route of administration, including e.g., orally in the form tablets or capsules or liquid, or in sterile aqueous solution for injection. In other embodiments, the PC is provided in a dry lyophilized powder to be added to the formulation of the replacement enzyme during or immediately after reconstitution to prevent enzyme aggregation in vitro prior to administration.

When the PC (e.g., migalastat or salt thereof) is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active chaperone compound.

The pharmaceutical formulations of the PC (e.g., migalastat or salt thereof) suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the purified enzyme (if any) and the PC (e.g., migalastat or salt thereof) in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, bicarbonate buffer, amino acids, urea, alcohols, ascorbic acid, and phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The route of administration of the chaperone compound may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of the chaperone compound may be by periodic injections of a bolus of the preparation, or may be administered by intravenous or intraperitoneal administration from a reservoir which is external (e.g., an i.v. bag) or internal (e.g., a bioerodable implant).

Embodiments relating to pharmaceutical formulations and administration may be combined with any of the other embodiments of the invention, for example embodiments relating to methods of treating patients with Fabry disease, methods of treating ERT-naïve patients with Fabry disease, methods of reducing kidney GL-3, methods of stabilizing renal function, methods of reducing LVM or LVMi, methods of reducing plasma lyso-Gb$_3$ and/or methods of treating gastrointestinal symptoms (e.g. diarrhea), methods of enhancing α-Gal A in a patient diagnosed with or suspected of having Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to amenable mutations, the PCs and suitable dosages thereof.

In one or more embodiments, the PC (e.g., migalastat or salt thereof) is administered in combination with ERT. ERT increases the amount of protein by exogenously introducing wild-type or biologically functional enzyme by way of infusion. This therapy has been developed for many genetic disorders, including LSDs such as Fabry disease, as referenced above. After the infusion, the exogenous enzyme is expected to be taken up by tissues through non-specific or receptor-specific mechanism. In general, the uptake efficiency is not high, and the circulation time of the exogenous protein is short. In addition, the exogenous protein is unstable and subject to rapid intracellular degradation as well as having the potential for adverse immunological reactions with subsequent treatments. In one or more embodiments, the chaperone is administered at the same time as replacement enzyme (e.g., replacement α-Gal A). In some embodiments, the chaperone is co-formulated with the replacement enzyme (e.g., replacement α-Gal A).

In one or more embodiments, a patient is switched from ERT to migalastat therapy. In some embodiments, a patient on ERT is identified, the patient's ERT is discontinued, and the patient begins receiving migalastat therapy. The migalastat therapy can be in accordance with any of the methods described herein.

Stabilization of Renal Function

The dosing regimens described herein can stabilize renal function in Fabry patients with varying degrees of renal impairment. In one or more embodiments, a Fabry patient having renal impairment is administered about 100 mg to about 150 mg FBE of migalastat or salt thereof at a frequency of once every other day. In one or more embodiments, the patient is administered 123 mg FBE of migalastat or salt thereof, such as 123 mg of migalastat or 150 mg of migalastat hydrochloride every other day. In one or more embodiments, the patient has mild or moderate renal impairment. In specific embodiments, the patient has mild renal impairment. In other specific embodiments, the patient has moderate renal impairment. The patient may be ERT-naïve or ERT-experienced.

The administration of migalastat may be for a certain period of time. In one or more embodiments, the migalastat is administered for at least 28 days, such as at least 30, 60 or 90 days or at least 3, 4, 5, 6, 7, 8, 9, 10, 11, 12, 16, 20 or 24 months or at least 1, 2, 3, 4 or 5 years. In various embodiments, the migalastat therapy is long-term migalastat therapy of at least 6 months, such as at least 6, 7, 8, 9, 10, 11, 12, 16, 20 or 24 months or at least 1, 2, 3, 4 or 5 years.

The migalastat therapy may reduce the decline in renal function for a Fabry patient compared to the same patient without treatment with migalastat therapy. In one or more embodiments, the migalastat therapy provides an annualized change in eGFR$_{CKD-EPI}$ for a patient that is greater than (i.e. more positive than) −5.0 mL/min/1.73 m$^2$/year, such as greater than −4.5, −4.0, −3.5, −3.0, −2.5, −2.0, −1.5, −1.0, −0.9, −0.8, −0.7, −0.6, −0.5, −0.4, −0.3, −0.2, −0.1 or even greater than 0 mL/min/1.73 m$^2$/year. In one or more embodiments, the migalastat therapy provides an annualized change in mGFR$_{iohexol}$ for a patient that is greater than −5.0 mL/min/1.73 m$^2$/year, such as greater than −4.5, −4.0, −3.5, −3.0, −2.5, −2.0, −1.5, −1.0, −0.9, −0.8, −0.7, −0.6, −0.5, −0.4, −0.3, −0.2, −0.1 or even greater than 0 mL/min/1.73 m$^2$/year Accordingly, the migalastat therapy may reduce the decline or even improve the renal function of the patient. These annualized rates of change can be measured over a specific time period, such as over 6 months, 12 months, 18 months, 24 months, 30 months, 36 months, 48 months or 60 months.

The migalastat therapy may reduce the decline in renal function for a group of Fabry patients, such as subpopulations of Fabry patients having varying degrees of renal impairment. In one or more embodiments, the migalastat therapy provides a mean annualized rate of change in eGFR$_{CKD-EPI}$ in Fabry patients having mild, moderate or severe renal impairment that is greater than −5.0 mL/min/1.73 m$^2$/year, such as greater than −4.5, −4.0, −3.5, −3.0, −2.5, −2.0, −1.5, −1.0, −0.9, −0.8, −0.7, −0.6, −0.5, −0.4, −0.3, −0.2, −0.1 or even greater than 0 mL/min/1.73 m$^2$/year. In one or more embodiments, the migalastat therapy provides a mean annualized rate of change in mGFR$_{iohexol}$ in patients having mild, moderate or severe renal impairment that is greater than −5.0 mL/min/1.73 m$^2$/year, such as greater than −4.5, −4.0, −3.5, −3.0, −2.5, −2.0, −1.5, −1.0, −0.9, −0.8, −0.7, −0.6, −0.5, −0.4, −0.3, −0.2, −0.1 or even greater than 0 mL/min/1.73 m$^2$/year. These mean annualized rates of change can be measured over a specific time period, such as over 6 months, 12 months, 18 months, 24 months, 30 months, 36 months, 48 months or 60 months.

Left Ventricular Mass

The dosing regimens described herein can improve LVMi in Fabry patients. The natural history of LVMi and cardiac hypertrophy in untreated Fabry patients regardless of phenotype (Patel, O'Mahony et al. 2015) is a progressive increase in LVMi between +4.07 and +8.0 g/m$^2$/year (Kampmann, Linhart et al. 2008; Wyatt, Henley et al. 2012; Germain, Weidemann et al. 2013). As untreated Fabry patients typically exhibit an increase in LVMi over time, both decreases in and maintenance of LVMi are indications of a benefit of migalastat therapy.

The migalastat therapy may reduce the increase in LVMi for a Fabry patient compared to the same patient without treatment with migalastat therapy. In one or more embodiments, the migalastat therapy provides a change in LVMi for a patient that is less than (i.e., more negative than) 0 g/m$^2$, such as less than or equal to about −0.5, −1, −1.5, −2, −2.5, −3, −3.5, −4, −4.5, −5, −5.5, −6, −7, −8, −9, −10, −11, −12, −13, −14, −15, −16, −17, −18, −19 or −20 g/m$^2$. Expressed differently, in one or more embodiments, the migalastat therapy provides a reduction in LVMi of greater than 0 g/m$^2$, such as reductions of at least about 0.5, 1, 1.5, 2, 2.5, 3, 3.5, 4, 4.5, 5, 5.5, 6, 7, 8, 9, 10, 11, 12, 13, 14, 15, 16, 17, 18, 19 or 20 g/m$^2$. In one or more embodiments, the patient has mild or moderate renal impairment. In specific embodiments, the patient has mild renal impairment. In other specific embodiments, the patient has moderate renal impairment. The patient may be ERT-naïve or ERT-experienced.

In one or more embodiments, the migalastat therapy provides an average decrease of LVMi in a group of ERT-experienced patients of at least about 1 g/m$^2$ after 18 months of administration of migalastat or a salt thereof. In various embodiments, the average decrease in the group of ERT-experienced patients after 18 months of administration of migalastat or a salt thereof is at least about 1, 2, 3, 4, 5, 6, 7, 8, 9 or 10 g/m$^2$.

In one or more embodiments, the migalastat therapy provides an average decrease of LVMi in a group of ERT-experienced patients having moderate renal impairment of at least about 1 g/m$^2$ after 18 months of administration of migalastat or a salt thereof. In various embodiments, the average decrease in the group of ERT-experienced patients after 18 months of administration of migalastat or a salt thereof is at least about 1, 2, 3, 4, 5, 6, 7, 8, 9 or 10 g/m$^2$.

In one or more embodiments, the migalastat therapy provides an average decrease of LVMi in a group of ERT-naïve patients of at least about 1 g/m$^2$ after 24 months of administration of migalastat or a salt thereof. In various embodiments, the average decrease in the group of ERT-naïve patients after 24 months of administration of migalastat or a salt thereof is at least about 1, 2, 3, 4, 5, 6, 7, 8, 9 or 10 g/m$^2$.

In one or more embodiments, the migalastat therapy provides an average decrease of LVMi in a group of ERT-naïve patients having moderate renal impairment of at least about 1 g/m$^2$ after 24 months of administration of migalastat or a salt thereof. In various embodiments, the average decrease in the group of ERT-naïve patients after 24 months of administration of migalastat or a salt thereof is at least about 1, 2, 3, 4, 5, 6, 7, 8, 9 or 10 g/m$^2$.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in various embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

Patents, patent applications, publications, product descriptions, and protocols are cited throughout this application, the disclosures of which are incorporated herein by reference in their entireties for all purposes.

EXAMPLES

Example 1: Pharmacokinetics of Migalastat in Non-Fabry Patients with Renal Impairment A clinical trial was conducted to study the pharmacokinetics and safety of migalastat HCl in non-Fabry subjects with renal impairment. A single 150 mg migalastat HCl dose was administered to subjects with mild, moderate, and severe renal impairment, and normal renal function. The eGFR was estimated by the Cockcroft-Gault equation per the FDA Guidance for renal impairment studies.

Volunteers were enrolled into two cohorts stratified for renal function calculated using the Cockcroft-Gault equation for creatinine clearance ($CL_{CR}$). Subjects were assigned to groups based on an estimated $CL_{CR}$ at screening as calculated using the Cockcroft-Gault equation. For each subject, the following plasma migalastat PK parameters were determined by noncompartmental analysis with WinNonlin® software (Pharsight Corporation, Version 5.2).

$C_{max}$ maximum observed concentration
$t_{max}$ time to maximum concentration
$AUC_{0-t}$ area under the concentration-time curve from Hour 0 to the last measurable concentration, calculated using the linear trapezoidal rule for increasing concentrations and the logarithmic rule for decreasing concentrations
$AUC_{0-\infty}$ area under the concentration-time curve extrapolated to infinity, calculated using the formula:

$$AUC0-\infty = AUC0-t + Ct/\lambda Z$$

where Ct is the last measurable concentration and $\lambda Z$ is the apparent terminal elimination rate constant
$\lambda z$ apparent terminal elimination rate constant, where $\lambda Z$ is the magnitude of the slope of the linear regression of the log concentration versus time profile during the terminal phase
$t_{1/2}$ apparent terminal elimination half-life (whenever possible), where $t_{1/2} = (\ln 2)/\lambda Z$
CL/F oral clearance, calculated as Dose/AUC0-∞
Vd/F oral volume of distribution, calculated as Dose/AUC0-∞·$\lambda Z$
$C_{48}$ concentration at 48 hours post-dose Pharmacokinetic parameters determined were: area under the concentration-time curve (AUC) from time zero to the last measurable concentration post-dose ($AUC_{0-t}$) and extrapolated to infinity ($AUC_{0-\infty}$), maximum observed concentration ($C_{max}$), time to $C_{max}$ ($t_{max}$), concentration at 48 hours post-dose ($C_{48}$), terminal elimination half-life ($t_{1/2}$), oral clearance (CL/F), and apparent terminal elimination rate constant ($\lambda z$).

Study subjects were defined as having renal impairment if creatinine clearance ($CL_{CR}$) was less than 90 mL/min (i.e. $CL_{CR}$<90 mL/min) as determined using the Cockcroft-Gault formula. Subjects were grouped according to degree of renal dysfunction: mild (CLcr ≥60 and <90 mL/min), moderate ($CL_{CR}$≥30 and <60 mL/min), or severe ($CL_{CR}$≥15 and <30 mL/min)

The plasma and urine pharmacokinetics of migalastat have been studied in healthy volunteers and Fabry patients with normal to mildly impaired renal function. In the single-dose studies, migalastat had a moderate rate of absorption reaching maximum concentrations in approximately 3 hours (range, 1 to 6 hrs) after oral administration over the dose range studied. Mean $C_{max}$ and $AUC_{0-t}$ values increased in a dose-proportional manner following oral doses from 75 mg to 1250 mg migalastat. The mean elimination half-lives ($t_{1/2}$) ranged from 3.04 to 4.79 hours. Mean percent of the dose recovered in urine from doses evaluated in the single ascending dose (SAD) study were 32.2%, 43.0%, 49.3%, and 48.5% for the 25 mg, 75 mg, 225 mg, and 675 mg dose groups, respectively. In multiple ascending dose studies, only minimal accumulation of plasma migalastat was observed. In a TQT study, migalastat was negative for effect on cardiac repolarization at 150 mg and 1250 mg single doses (Johnson et al., Clin Pharmacol Drug Dev. 2013 April; 2(2):120-32).

In this single dose renal impairment study conducted in non-Fabry subjects, plasma concentrations of single-dose migalastat HCl 150 mg increased with increasing degree of renal failure compared to subjects with normal renal function. Following a single oral dose of migalastat HCl 150 mg, mean plasma migalastat $AUC_{0-\infty}$ increased in subjects with mild, moderate, or severe renal impairment by 1.2-fold, 1.8-fold, and 4.5-fold, respectively, compared to healthy control subjects. Increases in plasma migalastat $AUC_{0-\infty}$ values were statistically significant in subjects with moderate or severe renal impairment but not in subjects with mild renal impairment following single-dose administration compared to subjects with normal renal function. Migalastat $t_{max}$ was slightly delayed in the severe group; $C_{max}$ was not increased across any of the groups following a single oral dose of migalastat HCl 150 mg in subjects with varying degrees of renal impairment compared to healthy control subjects. Plasma migalastat $C_{48}$ levels were elevated in subjects with moderate (predominantly from subjects with $Cr_{CL}$<50 mL/min) and severe renal impairment compared with healthy control subjects. The $t_{1/2}$ of migalastat in plasma increased as the degree of renal impairment increased (arithmetic mean [min, max]: 6.4 [3.66, 9.47], 7.7 [3.81, 13.8], 22.2 [6.74, 48.3], and 32.3 [24.6, 48.0] h) in subjects with normal renal function and those with mild, moderate, or severe renal impairment, respectively. Mean CL/F decreased with increasing degree of renal failure and ranged from 12.1 to 2.7 L/hr from mild to severe renal impairment (Johnson, et al., American College of Clinical Pharmacology 4.4 (2015): 256-261).

Migalastat clearance decreased with increasing renal impairment, resulting in increases in migalastat HCl plasma $t_{1/2}$, $AUC_{0-\infty}$, and $C_{48}$ compared with subjects with normal renal function. Incidence of adverse events was comparable across all renal function groups.

Figure 1B:
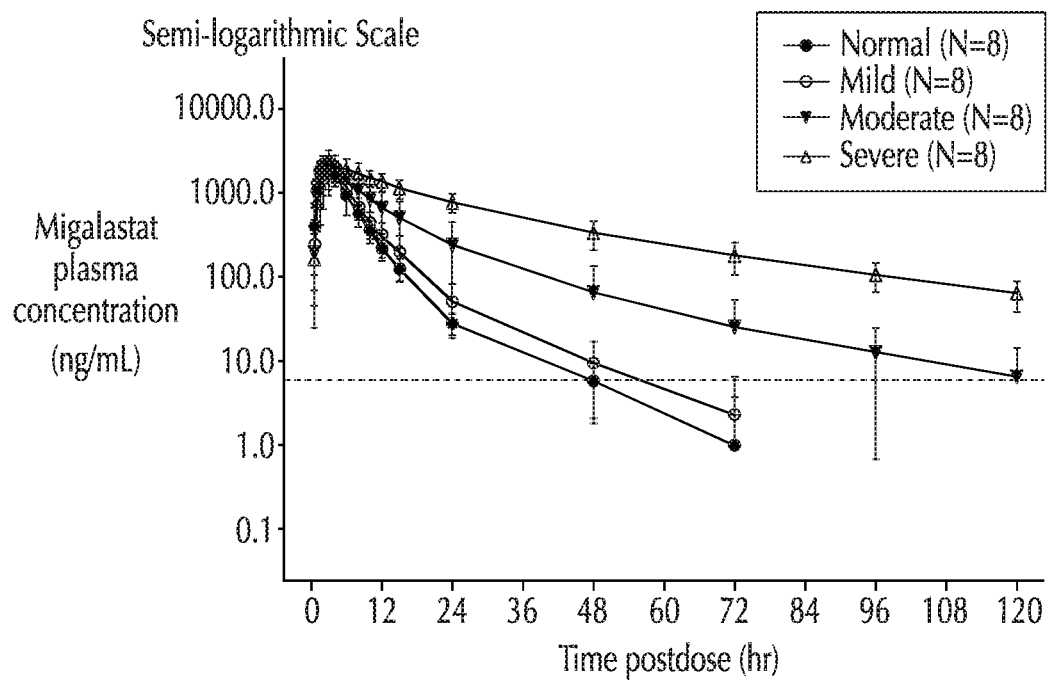
FIG. 1B shows the migalastat plasma concentrations for non-Fabry patients with varying degrees of renal impairment as a function of time post-dose.

Following a single oral dose of 150 mg migalastat HCl plasma exposure (expressed as $AUC_{0-t}$) increased as the degree of renal impairment increased. FIG. 1A shows an increase in migalastat $AUC_{0-t}$ values as $CL_{CR}$ values decrease. FIG. 1B shows the mean (SE) plasma migalastat concentration-time profiles for each renal function group. BLQ values were entered as zero and included in the calculation of means.

Figure 1C:
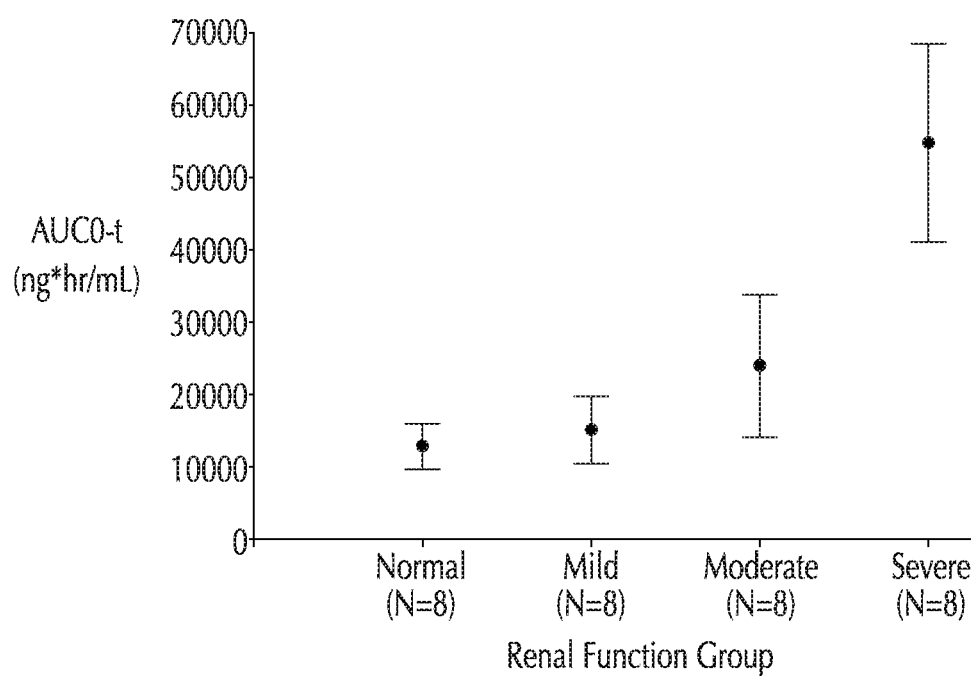
FIG. 1C shows the area under the curve (AUC) for non-Fabry patients with varying degrees of renal impairment.

As demonstrated in FIG. 1C, as renal impairment worsens, plasma migalastat $AUC_{0-t}$ values increase in a nonlinear manner. Results demonstrated that, as renal impairment worsened, the clearance of plasma migalastat decreased, resulting in prolonged $t_{1/2}$, higher $C_{48}$ values, and higher overall plasma exposure ($AUC_{0-\infty}$), in particular in subjects with severe renal impairment. Migalastat is primarily excreted unchanged in urine. Thus, an increase in plasma migalastat exposure is consistent with worsening renal impairment.

Conclusions: Plasma migalastat clearance decreased as degree of renal impairment increased.

A summary of the PK results are shown in Table 3 below.

Figure 2:
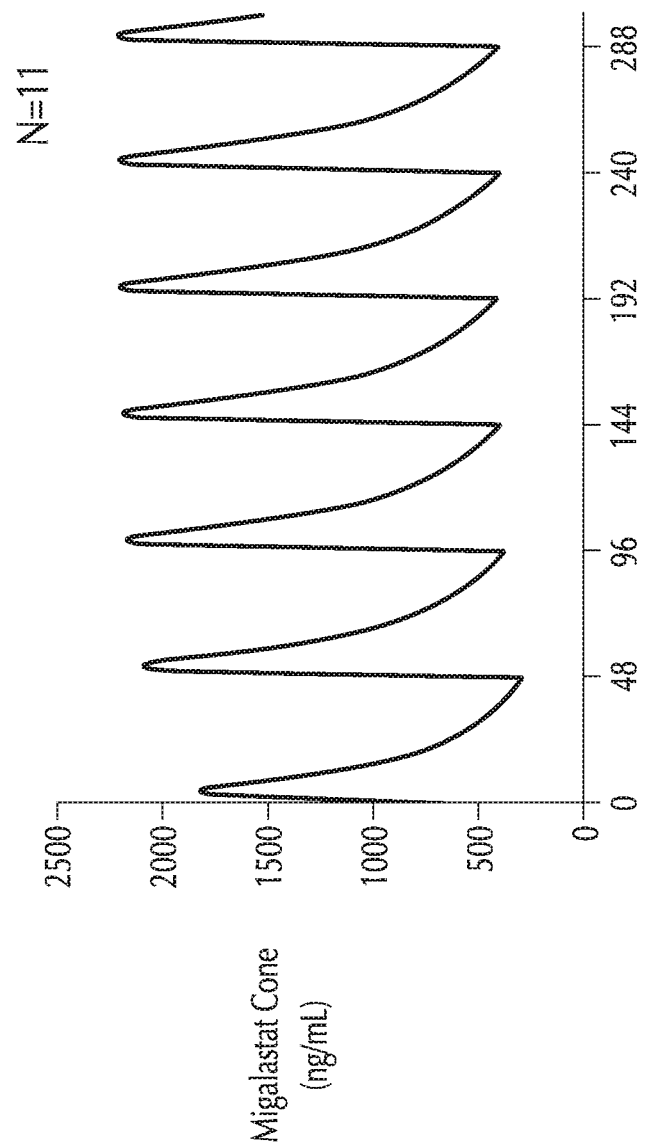
FIG. 2 shows migalastat concentration as a function of time for patients having moderate to severe renal impairment.

FIG. 2 shows the mean simulation plots for the dosing regimen of 150 mg migalastat HCl QOD. Table 4 below shows the exposures and accumulation ratios.

Figure 3:
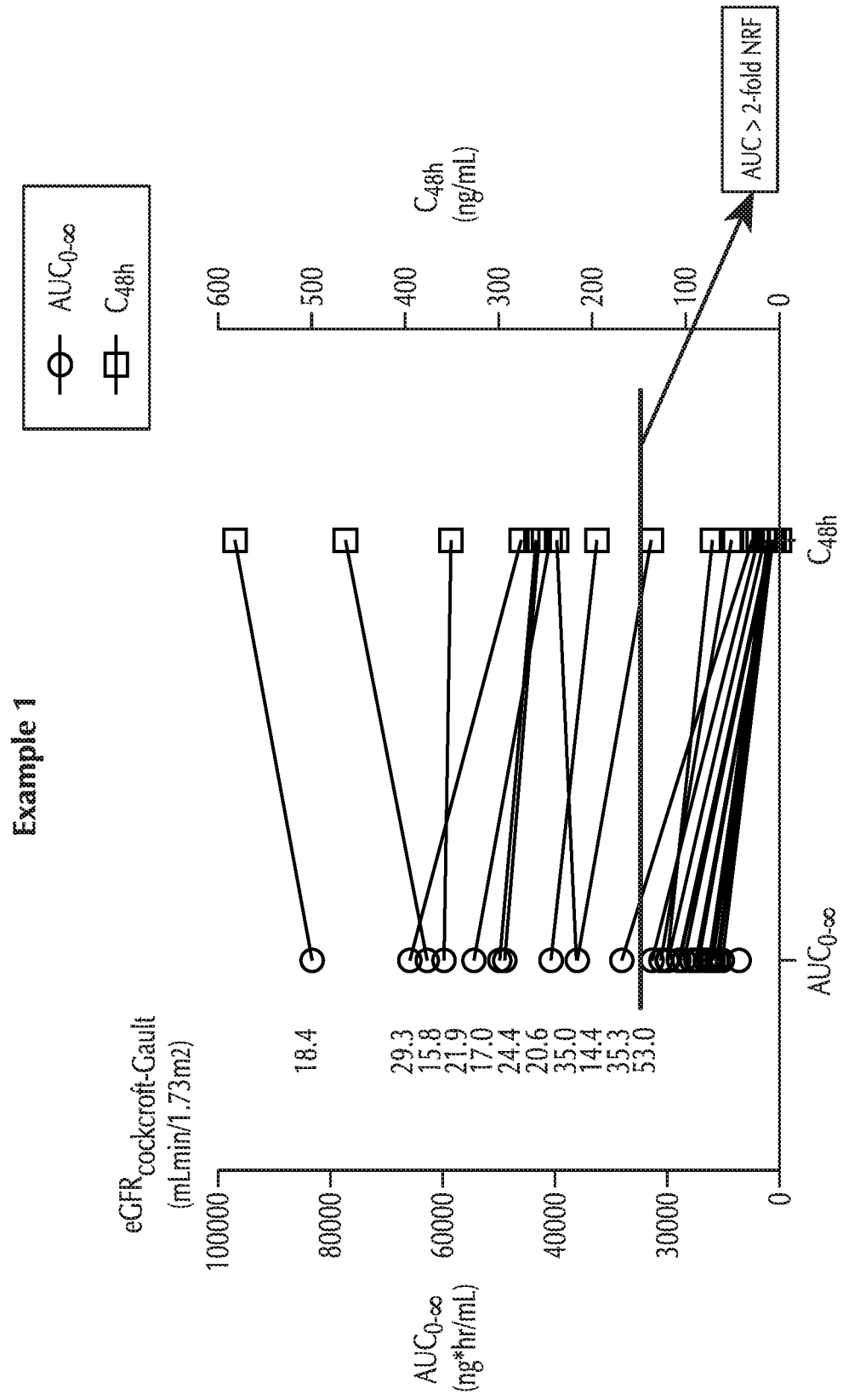
FIG. 3 shows the correlation between $AUC_{0-\infty}$ and migalastat concentration after 48 hours for non-Fabry patients with varying degrees of renal impairment.

FIG. 3 shows AUC versus $C_{48}$ from Example 1. This stick plot provides a visual correlation of AUC to $C_{48}$ concentration across all levels of renal function, and demonstrates the two values are well visually correlated.

TABLE 4

| Subject | Renal Function Group | BSA-Adj eGFR-Cockcroft-Gault (mL/min/1.73 m$^2$) | $AUC_{0-48\,h}$ | $R_{ac48\,h}$ |
|---|---|---|---|---|
| 1 | Moderate (≥30-≤35) | 35.3 | 31920 | 1.12 |
| 2 | Moderate (≥30-≤35) | 35.0 | 35320 | 1.17 |
| 3 | Moderate (≥30-≤35) | 32.2 | 17507 | 1.12 |
| 4 | Severe (<30) | 18.4 | 59178 | 1.42 |
| 5 | Severe (<30) | 17.0 | 44124 | 1.21 |
| 6 | Severe (<30) | 20.6 | 37409 | 1.28 |
| 7 | Severe (<30) | 15.8 | 41687 | 1.54 |

TABLE 3

| PK Parameter | Units | Renal Function Group | | | |
|---|---|---|---|---|---|
| | | Normal (N = 8) | Mild (N = 8) | Moderate (N = 8) | Severe (N = 8) |
| $AUC_{0-t}$ | (ng · hr/mL) | 12306 (27.9) | 14389 (31.1) | 22126 (42.8) | 53070 (27.0) |
| $AUC_{0-\infty}$ | (ng · hr/mL) | 12397 (27.7) | 14536 (30.7) | 22460 (42.2) | 56154 (24.9) |
| $C_{max}$ | (ng/mL) | 2100 (26.0) | 2191 (28.8) | 1868 (32.1) | 2078 (45.5) |
| $t_{max}$ | (hr) | 2.50 (1.50, 3.00) | 2.50 (1.50, 4.00) | 3.00 (1.50, 4.00) | 4.27 (3.00, 8.00) |
| $t_{1/2}$ | (hr) | 6.42 (1.93) | 7.66 (3.02) | 22.2 (14.2) | 32.3 (7.35) |
| CL/F | (L/hr) | 12.1 (27.7) | 10.3 (30.7) | 6.68 (42.2) | 2.67 (24.9) |
| $C_{48}$ | (ng/mL) | 5.70 (3.63) | 9.34 (7.57) | 64.5 (68.1) | 334 (126) |

Example 2: Multiple Dose Simulations on Renal Impairment Subjects

In the renal impairment study of Example 1, consistent increases in area under the curve (AUC) and trough concentration of migalastat at 48 hours post-dose following QOD dosing ($C_{48}$) of 2- to 4-fold were observed at eGFR values ≤35 mL/min relative to subjects with normal renal function.

A population PK model was developed to predict exposures and time above $IC_{50}$ in Fabry patients with varying degrees of renal impairment. This example provides computer simulations of dosing the renal impairment subjects of Example 1. The key assumption was exposure characterized in non-Fabry subjects with renal impairment is the same as in Fabry patients with renal impairment. The software program was WinNonlin version 5.2 or higher. The conditions of the model are described below. 11 subjects who had BSA-adjusted eGFR$_{Cockcroft-Gault}$ ≤35 mL/min/1.73 m$^2$ were included in the modeling exercise; 3 had moderate renal impairment, but were ≥30 mL/min/1.73 m$^2$ and ≤35 mL/min/1.73 m$^2$, and 8 were ≥14 mL/min/1.73 m$^2$ and <30 mL/min/1.73 m$^2$. Steady state was assumed by 7$^{th}$ dose.

A 2-compartment model was used to estimate Vd and elimination rate constants from single dose data. These estimates were inputted into each molecular dose simulation regimen.

TABLE 4-continued

| Subject | Renal Function Group | BSA-Adj eGFR-Cockcroft-Gault (mL/min/1.73 m$^2$) | $AUC_{0-48\,h}$ | $R_{ac48\,h}$ |
|---|---|---|---|---|
| 8 | Severe (<30) | 21.9 | 45790 | 1.29 |
| 9 | Severe (<30) | 29.3 | 56331 | 1.17 |
| 10 | Severe (<30) | 14.4 | 23732 | 1.45 |
| 11 | Severe (<30) | 24.4 | 39012 | 1.26 |
| Geometric Mean | | 22.9 | 37256 | 1.27 |
| CV % | | 33.8 | 33.4 | 11.1 |

Example 3: Pharmacokinetics of Migalastat in Fabry Patients with Renal Impairment The computer modeling above provides scenarios for plasma migalastat exposure, but it does not account for renal impairment in Fabry patients. That is, the data does not include the pharmacodynamic component (plasma lyso-GB$_3$). Thus, two Fabry patients with renal impairment were evaluated. One patient (P1) had moderate renal impairment, while the other patient (P2) had severe renal impairment. Table 5 below shows plasma migalastat concentration for P1 compared with a study of ERT-naïve Fabry patients and moderately impaired subjects from the renal impairment study of Example 1. There are two sets of migalastat concentration measurements taken 6 months apart, and the patient had been previously treated with migalastat. Table 6 shows similar information for P2, except compared with severely impaired patients from the renal impairment study of Example 1. The ERT-naïve study was carried out in Fabry patients with amenable mutations where population PK was performed from sparse blood sampling. The comparison with the results from the ERT-naïve study allows for comparison of PK in the Fabry population with mostly normal, but some mild and a few moderately impaired Fabry patients. None of the patients in the ERT-naïve study had severe renal impairment because these patients were excluded from the study.

TABLE 5

| Hour Nominal | Time (hr) | Migalastat Conc (ng/mL) | Migalastat Conc 6 months later (ng/mL) | Comparison to ERT-Naïve Study PK | Comparison to Example 1 Moderate Impairment |
|---|---|---|---|---|---|
| 0 | Pre-dose | 19.9 | 36.4 | 8.70 | 64.5 (105.6%) |
| 3 | 3 Hrs Post | 1620 | 2160 | 1180 (31.0%) | 1868 (29.7%) |
| 24 | 24 Hrs Post | 168 | 211 | — | 239 (85.1%) |
| 48 | 48 Hrs Post | 41.8 | 62.4 | 8.70 | 64.5 (105.6%) |

TABLE 6

| Hour Nominal | Time Text | Occasion | Migalastat Concentration (ng/mL) | Comparison to ERT-Naïve Study PPK | Comparison to Example 1 Severe Impairment |
|---|---|---|---|---|---|
| 2 | 2 h | 1 | 564 | — | 1549 (59.3%) |
| 48 | 48 h | 1 | 322 | 8.70 | 334 (38.2%) |
| 24 | 24 h | 2 | 569 | — | 770 (26.5%) |
| 48 | 48 h | 2 | 260 | 8.70 | 334 (38.2%) |

As seen from Table 5, $C_{48}$ concentration, although increased by 49%, remains similar to Example 1 non-Fabry subjects with moderate renal impairment. $C_{max}$ has increased by 33%, but remains similar to Example 1. $C_{24}$ is similar to Example 1 for moderate renal impairment. $eGFR_{MDRD}$ remains within range for moderate impairment as well (32 mL/min).

The percentages in parentheses are coefficients of variation, which are relatively high, corresponding to variability in the time 0 h or time 48 h concentrations. This result is likely due to the fact that half of the subjects from Example 1 with moderate renal impairment had low concentrations and half of them high concentrations.

The concentrations at 48 hours are higher than at 0 hours for P1 (third and fourth columns), but for a person with moderate impairment from Example 1, the concentration at 48 hours is the same as at 0 hours. This is because separate blood samples were taken at times 0 and 48 in P1. However, repeat dose modeling simulation outputs from single dose data were used in Example 1, therefore the values are one in the same.

Similar trends can be seen from Table 6. Accordingly, Tables 5 and 6 confirm similar pharmacokinetics of migalastat in Fabry and non-Fabry patients having similar renal impairment.

Figure 4:
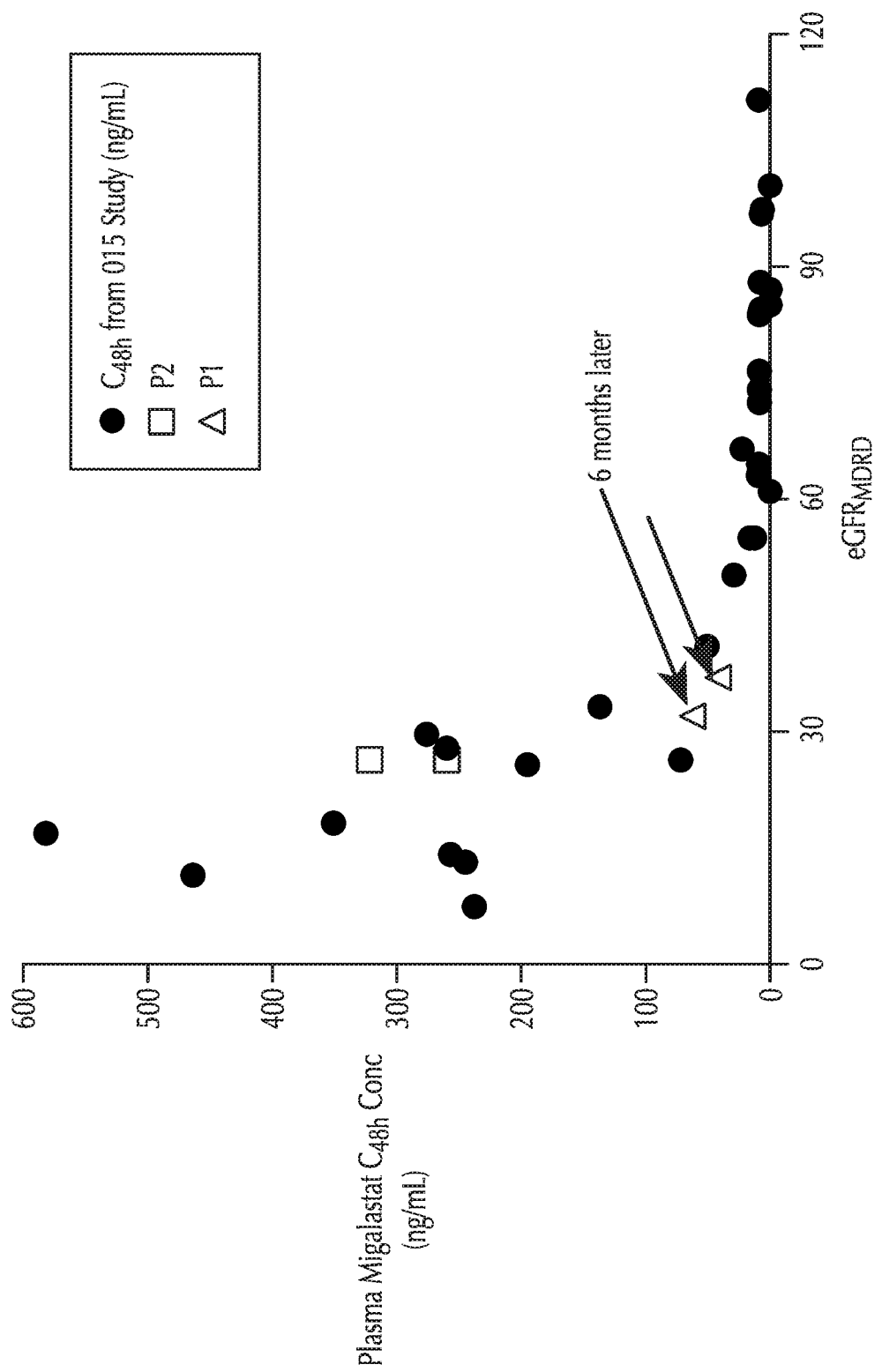
FIG. 4 shows plasma migalastat concentration after 48 hours as a function of $eGFR_{MDRD}$ for non-Fabry patients with varying degrees of renal impairment and two Fabry patients with renal impairment.
Figure 5:
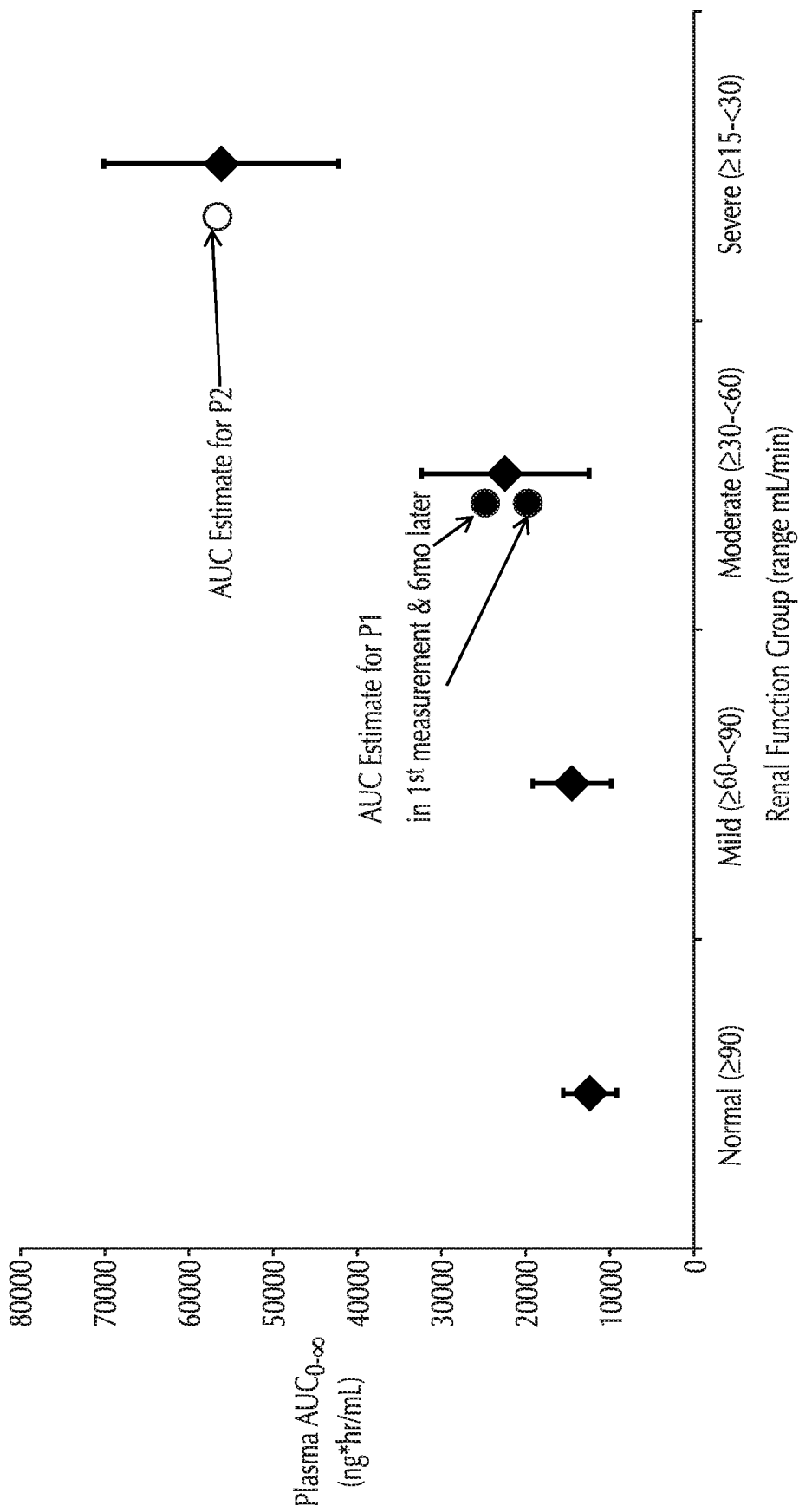
FIG. 5 shows plasma $AUC_{0-\infty}$ for non-Fabry patients with varying degrees of renal impairment and two Fabry patients with renal impairment.
Figure 6A:
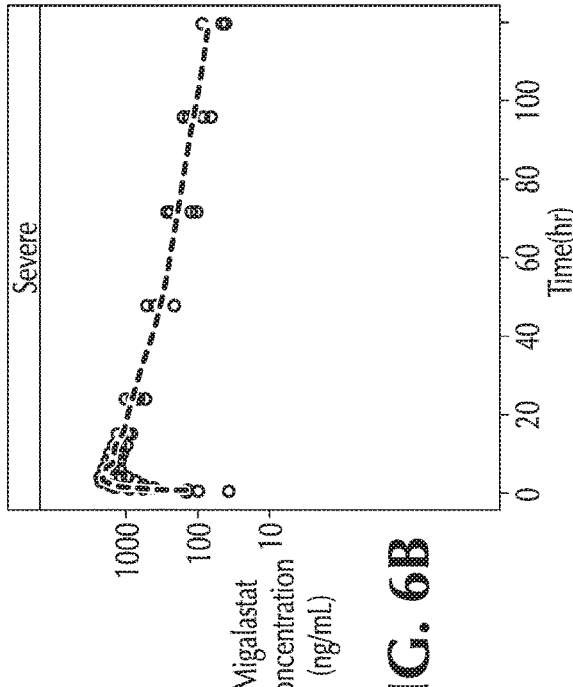
FIGS. 6A-D show simulated median and observed migalastat concentration versus time for normal, severe, mild and moderate renal impairment subjects, respectively.
Figure 6B:
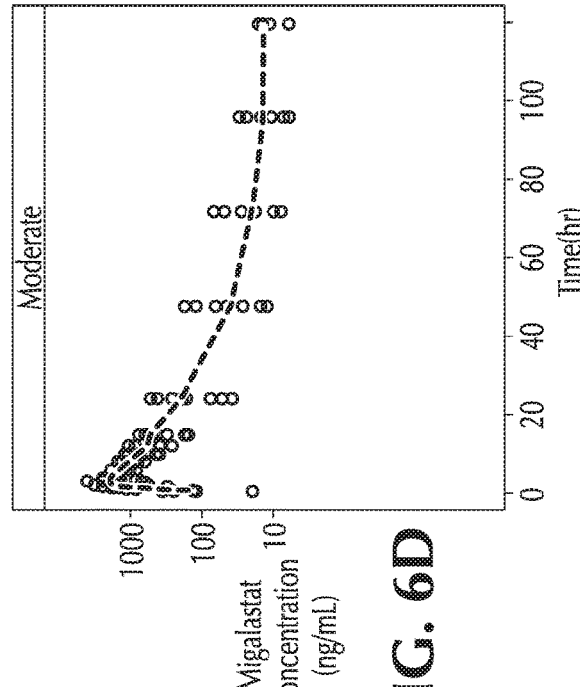
Figure 6C:
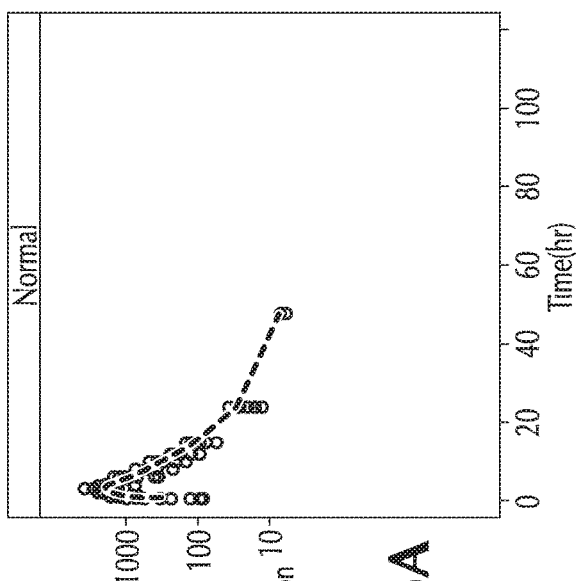
Figure 6D:
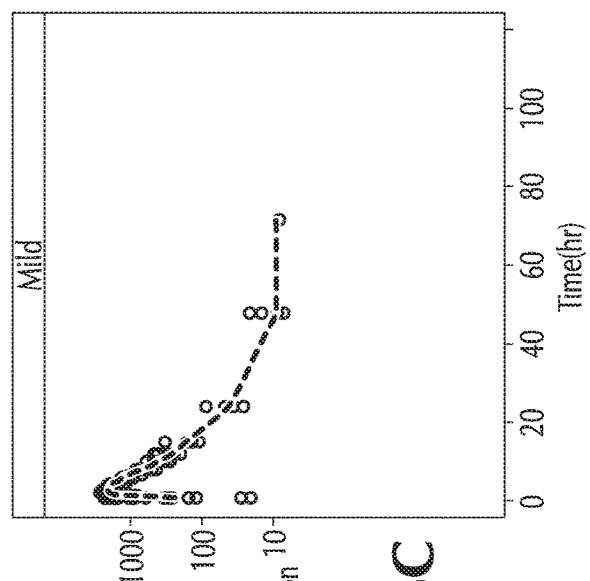
Figure 7A:
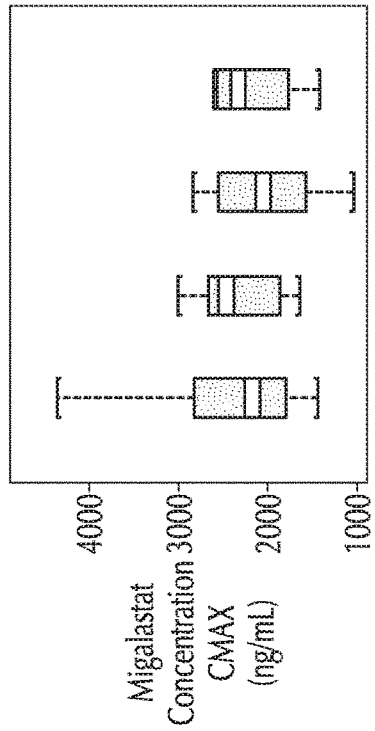
FIGS. 7A-D show simulated $C_{max}$, AUC, $C_{min}$ and $C_{48}$, respectively, for normal, mild, moderate and severe renal impairment subjects.
Figure 7B:
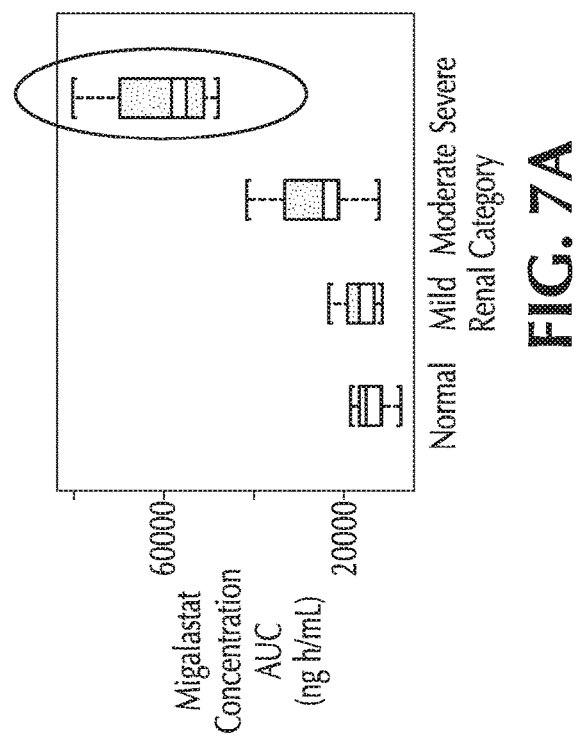
Figure 7C:
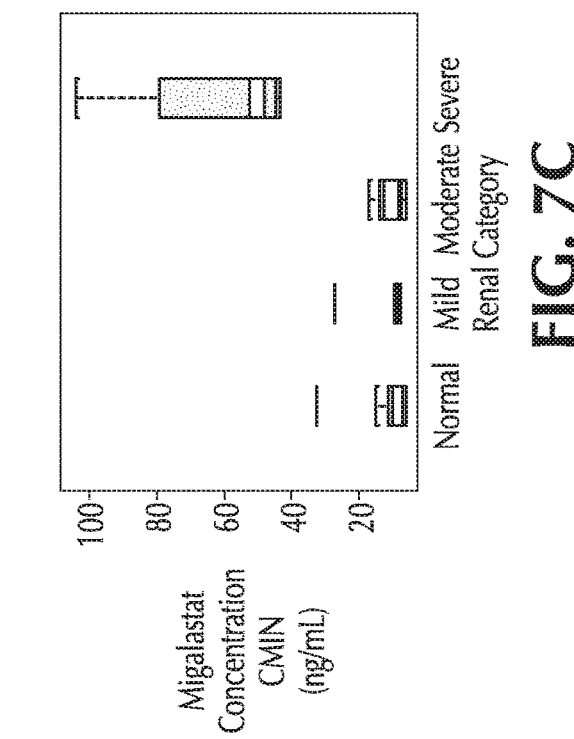
Figure 7D:
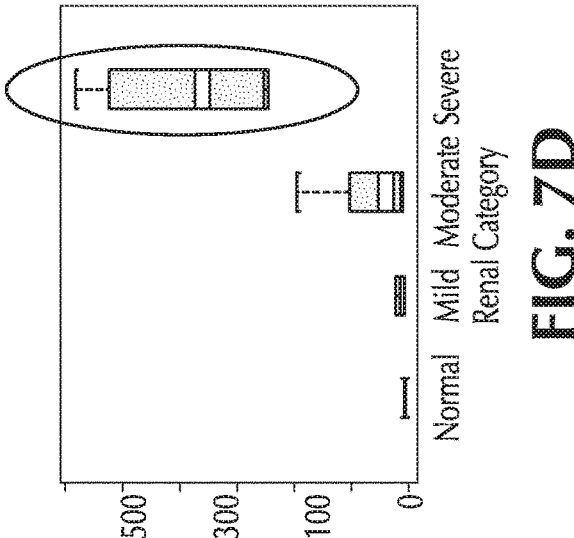
Figure 8A:
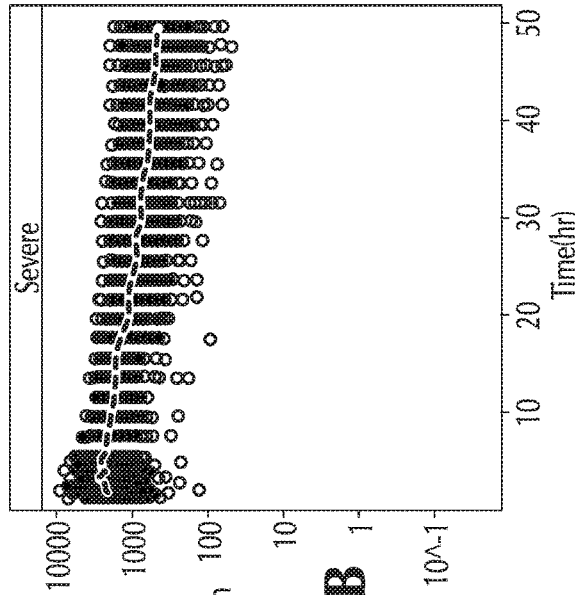
FIGS. 8A-D show the steady state prediction for QOD for normal, severe, mild and moderate renal impairment subjects, respectively.
Figure 8B:
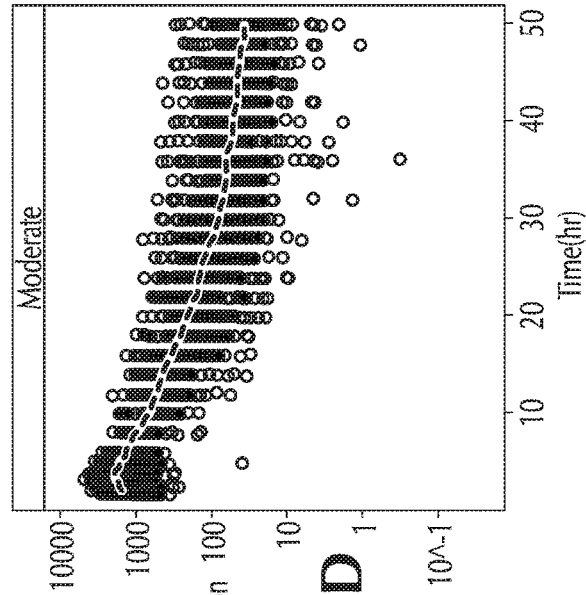
Figure 8C:
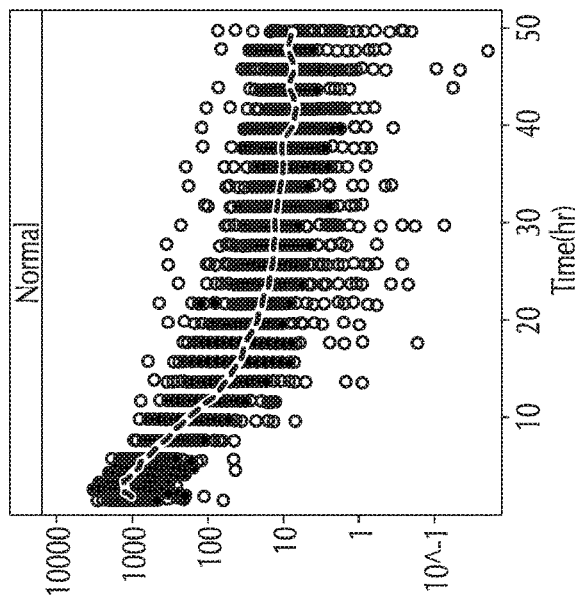
Figure 8D:
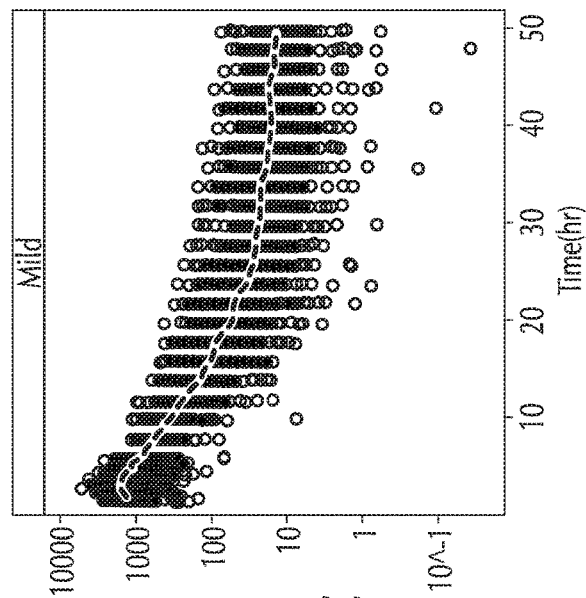

FIG. 4 shows the Fabry patients' plasma migalastat trough concentrations ($C_{48}$) versus the renal impairment study of Example 1. FIG. 5 shows the mean (SD) renal impairment study exposures versus Fabry patient estimated AUCs. As seen from the figure, P1 and P2 followed the general trend of the renal impairment study results in non-Fabry patients.

Table 7 below shows the Lyso-GB$_3$/eGFR for P1.

TABLE 7

| Visits | Lyso-Gb$_3$ (nM/L) | eGFR (MDRD), IDMS Traceable |
|---|---|---|
| 18 Month Visit | 11.1 | 42 |
| 24 Month Visit | 13.1 | 37 |

TABLE 7-continued

| Visits | Lyso-Gb$_3$ (nM/L) | eGFR (MDRD), IDMS Traceable |
|---|---|---|
| 30 Month Visit | 10.8 | Unavailable |
| 34-Month Visit | 9.3 | 32 |

Despite continued decline in renal function to eGFR of 32 mL/min/1.73 m2, plasma lyso-GB$_3$ has not shown clinically relevant changes from previous visits, and plasma migalastat concentrations remain similar to those observed in non-Fabry patients with moderate renal impairment.

This study demonstrates that the renal impairment and pharmacokinetic trends in Fabry patients correlates with the trends of non-Fabry patients.

Example 4: Additional Simulations on Renal Impairment Subjects

This example provides additional computer simulations of migalastat dosing of the renal impairment subjects of Example 1.

FIGS. 6A-D show simulated median and observed migalastat concentration versus time in normal, severe, mild and moderate renal impairment subjects, respectively. Table 8 below shows the data:

TABLE 8

| Renal Function Group (CL$_{CR}$ range mL/min), N | C$_{max}$ [a] (ng/ml) | AUC$_{0-\infty}$ [a] (hr*ng/ml) | AUC Ratio | t$_{1/2}$ [c] (hr) |
|---|---|---|---|---|
| Normal (>=90), 8 | 2270 (37.6) | 12808 (31.3) | — | 6.2 (1.6) |
| Mild (>=60-<90), 8 | 2278 (22.5) | 15359 (25.2) | 1.2 | 8.0 (2.8) |
| Moderate (>=30-<60), 8 | 2058 (47.1) | 23897 (38.9) | 1.9 | 23.0 (13.3) |
| Severe (<30), 4 | 2122 (29.1) | 61208 (23.1) | 4.8 | 32.5 (2.4) |

[a] Geometric mean (CV %)
[c] Mean (SD)

FIGS. 7A-D show simulated C$_{max}$, AUC, C$_{min}$ and C$_{48}$, respectively, for normal, mild, moderate and severe renal impairment subjects.

FIGS. 8A-D show the steady state prediction for QOD. The dashed line is the mean value from the QT study. FIGS. 9A-D show C$_{max}$, AUC, C$_{min}$ and C$_{48}$, respectively for the same simulation.

Figure 10A:
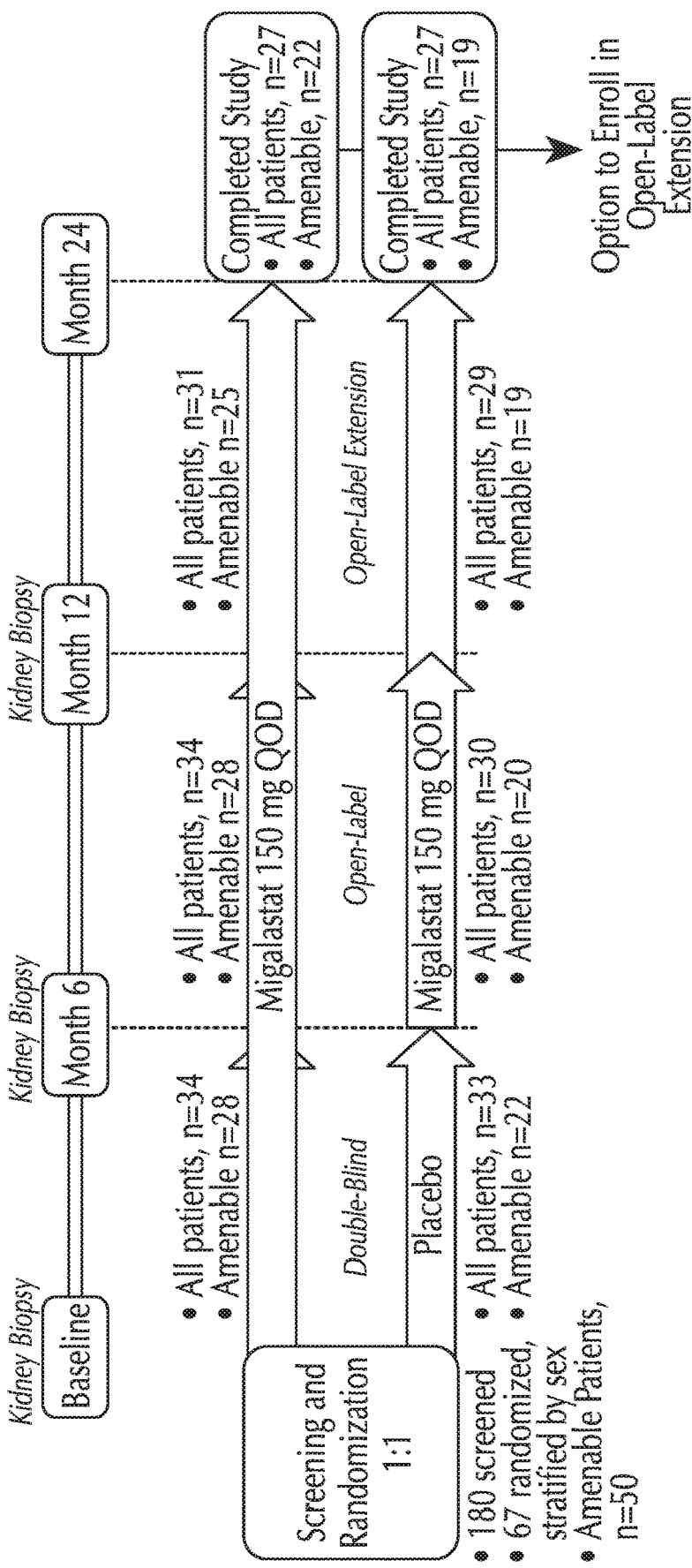
FIGS. 10A-B show the study designs for two studies investigating the use of migalastat in Fabry patients.
Figure 10B:
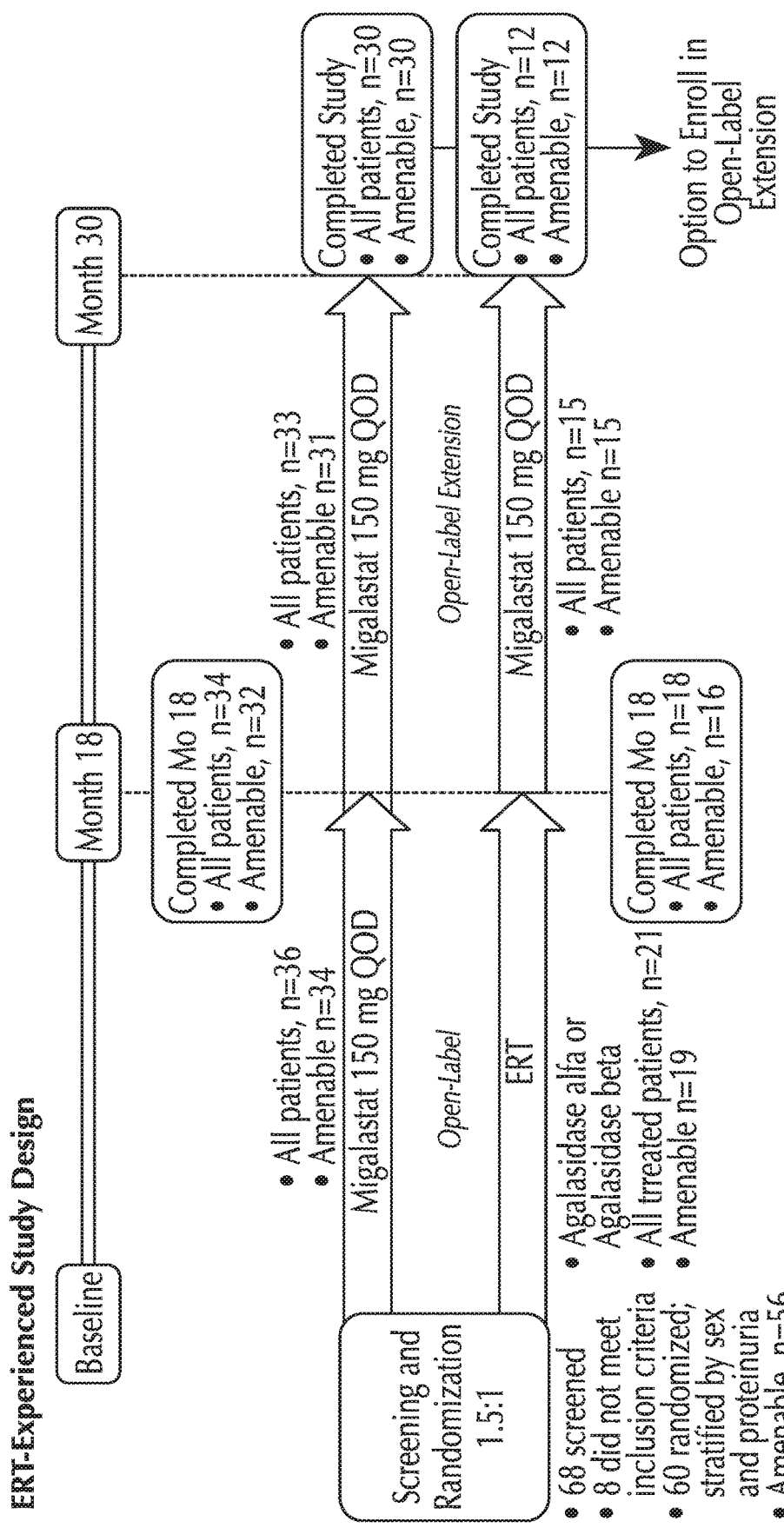

Example 5: Clinical Results of Migalastat Therapy in Fabry Patients with Renal Impairment and/or Elevated Proteinuria As described above, several studies were conducted using 150 mg of migalastat hydrochloride every other day (QOD) in Fabry patients. One study was a 24-month trial, including a 6-month double-blind, placebo-controlled period, in 67 ERT-naïve patients. The other study was an active-controlled, 18-month trial in 57 ERT-experienced patients with a 12-month open-label extension (OLE). Both the ERT-naïve and ERT-experienced studies included Fabry patients having an eGFR of ≥30 mL/min/1.73 m². The study designs for these studies are shown in FIGS. 10A-B.

In the ERT-experienced study, the primary efficacy parameters were the annualized changes (mL/min/1.73 m²/yr) from baseline through month 18 in measured GFR using iohexol clearance (mGFR$_{iohexol}$) and eGFR using the Chronic Kidney Disease Epidemiology Collaboration (CKD-EPI) formula (eGFR$_{CKD-EPI}$). Annualized change in eGFR using the Modification of Diet in Renal Disease (eGFR$_{MDRD}$) was also calculated.

In the ERT-naïve study, the primary efficacy parameter was GL-3 inclusions per kidney interstitial capillary. Renal function was also evaluated by mGFR$_{iohexol}$, eGFR$_{CKD-EPI}$ and eGFR$_{MDRD}$.

Figure 11:
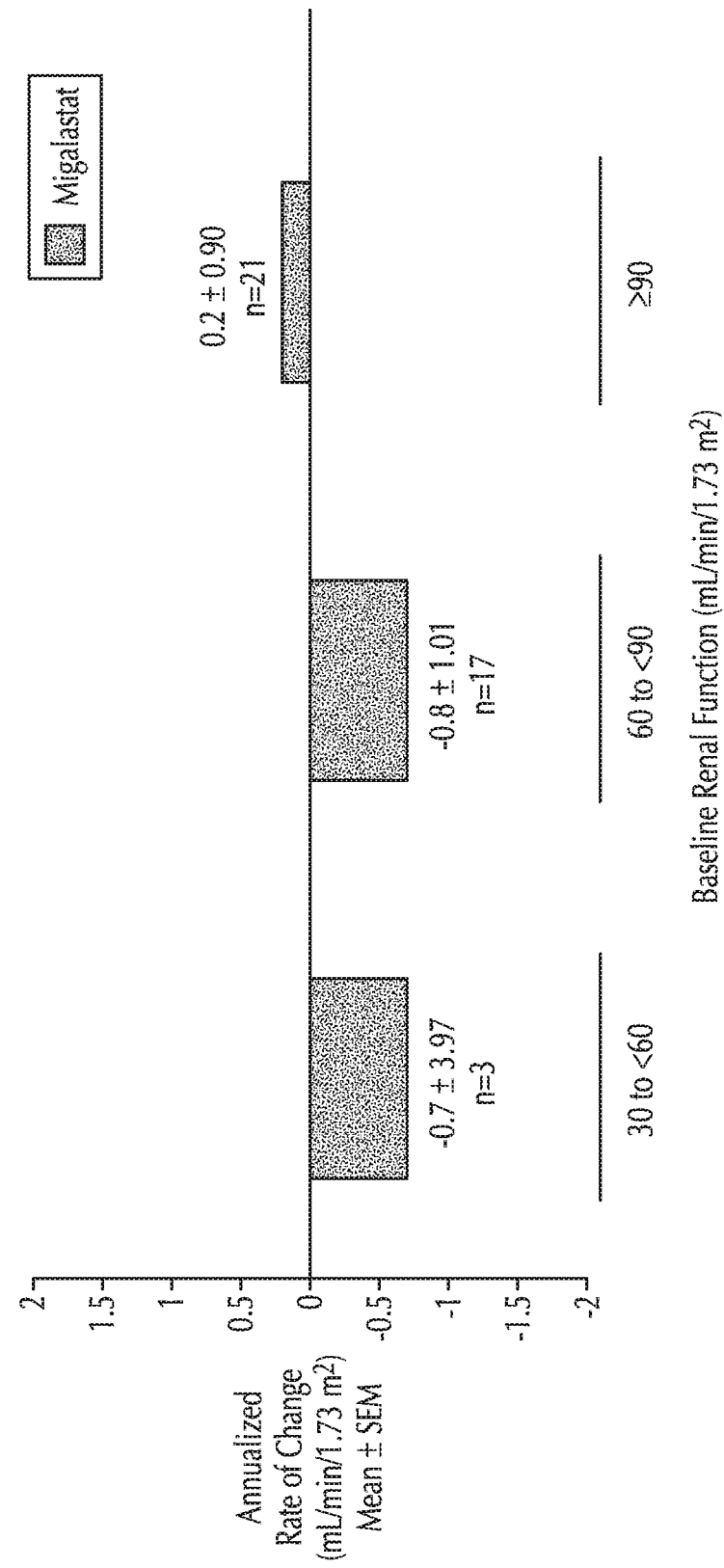
FIG. 11 shows annualized rate of change of $eGFR_{CKD-EPI}$ for Fabry patients on migalastat therapy having normal renal function and mild and moderate renal impairment.

A post-hoc analysis of data from the ERT-naïve study examined eGFR$_{CKD-EPI}$ annualized rate of change in subgroups based on eGFR at baseline for amenable patients with moderate renal impairment (30 to <60 mL/min/1.73 m²), mild renal impairment (60 to <90 mL/min/1.73 m²), and normal renal function (≥90 mL/min/1.73 m²). The annualized rate of change of eGFR$_{CKD-EPI}$ from baseline to 18/24 months is shown in FIG. 11. As can be seen from FIG. 11, patients with moderate renal impairment had a mean±SEM annualized rate of change of eGFR$_{CKD-EPI}$ of −0.7±3.97 mL/min/1.73 m²/year, patients with mild renal impairment had a mean annualized rate of change of eGFR$_{CKD-EPI}$ of −0.8±1.01 mL/min/1.73 m²/year, and patients with normal renal function had a mean annualized rate of change of eGFR$_{CKD-EPI}$ of 0.2±0.90 mL/min/1.73 m²/year. This data shows a stabilization of renal function with migalastat treatment was observed regardless of baseline eGFR.

Figure 12:
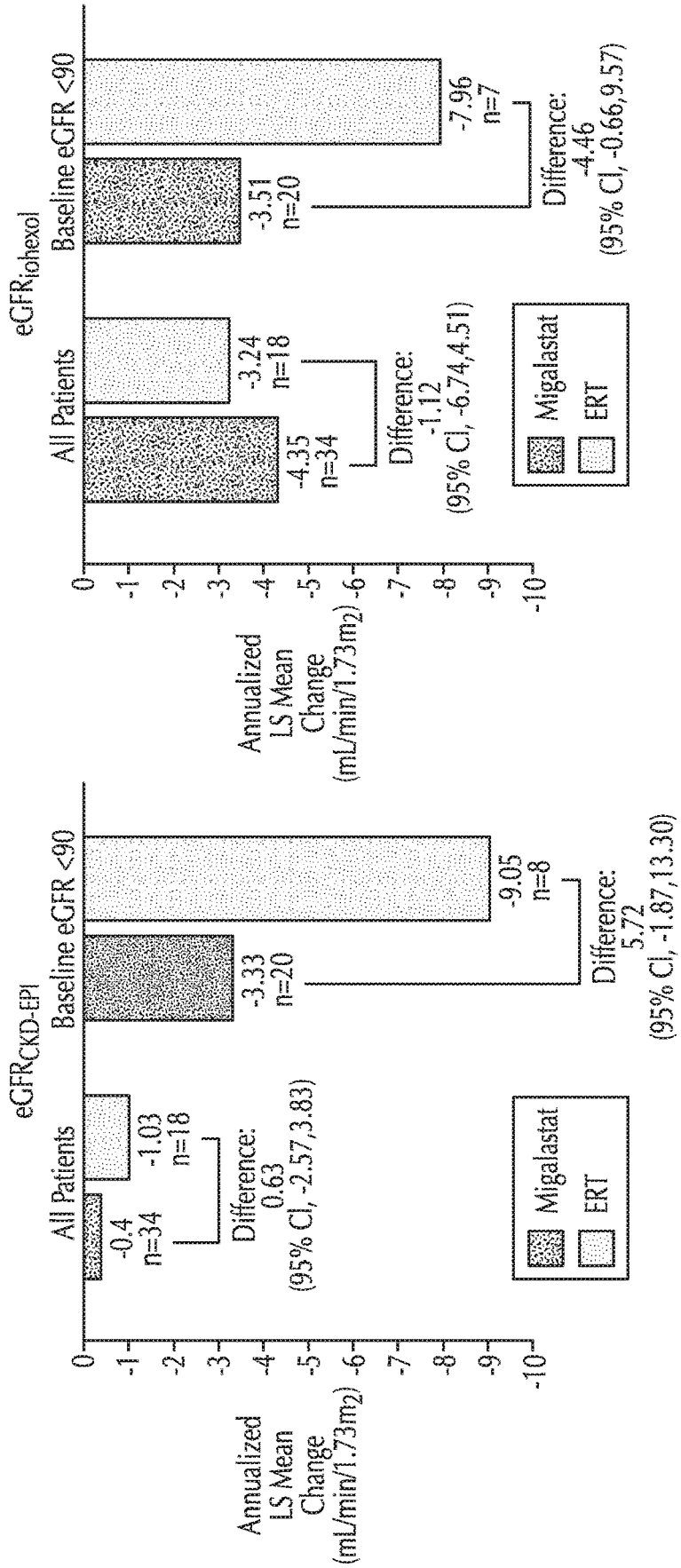
FIGS. 12A-B show annualized rate of change of $eGFR_{CKD-EPI}$ and $mGFR_{iohexol}$, respectively, for Fabry patients on migalastat therapy and ERT having normal renal function and renal impairment.

A post-hoc analysis of data from the ERT-experienced study examined eGFR$_{CKD-EPI}$ and mGFR$_{iohexol}$ annualized rate of change in subgroups based on eGFR at baseline for patients with mild/moderate renal impairment (30 to <90 mL/min/1.73 m²) and normal renal function (≥90 mL/min/1.73 m²). The annualized rates of change from baseline to 18 months for patients on migalastat therapy (patients with amenable mutations) and ERT is shown in FIGS. 12A-B for eGFR$_{CKD-EPI}$ and mGFR$_{iohexol}$, respectively. As can be seen from FIG. 12A, patients with normal renal function had a mean annualized rate of change of eGFR$_{CKD-EPI}$ of −0.4 mL/min/1.73 m²/year on migalastat therapy and −1.03 mL/min/1.73 m²/year on ERT. Patients with mild or moderate renal impairment had a mean annualized rate of change of eGFR$_{CKD-EPI}$ of −3.33 mL/min/1.73 m²/year on migalastat therapy and −9.05 mL/min/1.73 m²/year on ERT. As can be seen from FIG. 12B, patients with normal renal function had a mean annualized rate of change mGFR$_{iohexol}$ of −4.35 mL/min/1.73 m²/year on migalastat therapy and −3.24 mL/min/1.73 m²/year on ERT. Patients with mild or moderate renal impairment had a mean annualized rate of change mGFR$_{iohexol}$ of −3.51 mL/min/1.73 m²/year on migalastat therapy and −7.96 mL/min/1.73 m²/year on ERT. This data shows that migalastat therapy and ERT had comparable favorable effects on renal function using both GFR methods.

Figure 13:
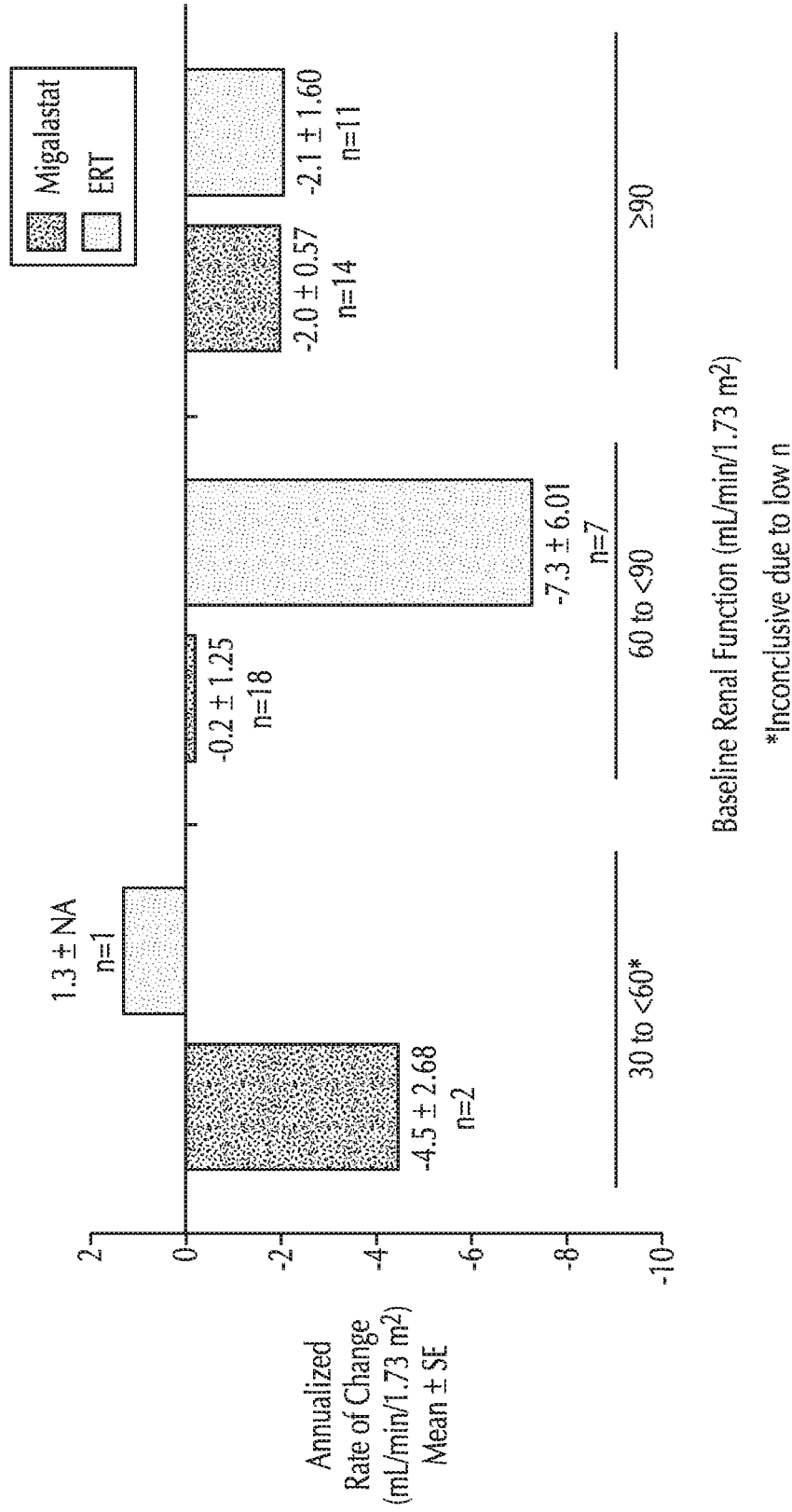
FIG. 13 shows annualized rate of change of $eGFR_{CKD-EPI}$ for Fabry patients on migalastat therapy and ERT having normal renal function and mild and moderate renal impairment.

Another post-hoc analysis of data from the ERT-experienced study examined eGFR$_{CKD-EPI}$ annualized rate of change in subgroups based on eGFR at baseline for patients with moderate renal impairment (30 to <60 mL/min/1.73 m²), mild renal impairment (60 to <90 mL/min/1.73 m²), and normal renal function (≥90 mL/min/1.73 m²). The annualized rates of change from baseline to 18 months for patients on migalastat therapy (patients with amenable mutations) and ERT is shown in FIG. 13. As can be seen from FIG. 13, patients with normal renal function had a mean±SE annualized rate of change of eGFR$_{CKD-EPI}$ of −2.0±0.57 mL/min/1.73 m²/year on migalastat therapy and −2.1±1.60 mL/min/1.73 m²/year on ERT. Patients with mild renal impairment had a mean±SE annualized rate of change of eGFR$_{CKD-EPI}$ of −0.2±1.25 mL/min/1.73 m²/year on migalastat therapy and −7.3±6.01 mL/min/1.73 m²/year on ERT. Patients with moderate renal impairment had a mean±SE annualized rate of change of eGFR$_{CKD-EPI}$ of −4.5±2.68 mL/min/1.73 m²/year on migalastat therapy and 1.3 mL/min/1.73 m²/year on ERT. This data shows that migalastat stabilized renal function regardless of whether the patient had normal renal function or mild renal impairment. Although the number of patients with moderate renal impairment included in this analysis is two (compared to three for the ERT-naïve study), the data supports the efficacy of migalastat when administered to patients with some form of renal impairment.

A further analysis of data from these studies examined annualized change in eGFR$_{CKD-EPI}$, LVMi, WBC α-Gal A activity and plasma lyso-Gb$_3$ levels based on renal function at baseline. The results for each renal subgroup are shown in Table 9 below, with the ERT-naïve study subgroups based on eGFR$_{MDRD}$ and the ERT-experienced study subgroups based on mGFR$_{iohexol}$.

TABLE 9

| Treatment | Renal Subgroup | Annualized Change in eGFR$_{CKD-EPI}$ mL/min/1.73 m$^2$ | LVMi, g/m$^2$ | WBC α-Gal A Activity, 4 MU/hr/mg (males only) | Plasma lyso-Gb$_3$, nmol/L (SD instead of SE) |
|---|---|---|---|---|---|
| | | Change from Baseline, mean ± SE [n] | | | |
| ERT-Naïve | | | | | |
| Migalastat→Migalastat 0-24 months | 30 to <60 | +3.2 ± 1.1 [2] | −5.5 ± 10.0 [2] | +1.4 [1] | −29.0 (41.5) [2] |
| | ≥60 | −0.7 ± 0.6 [20] | −9.2 ± 5.8 [14] | +1.6 ± 1.5 [3] | −7.7 (24.5) [14] |
| Placebo→Migalastat 6-24 months | 30 to <60 | −2.8 ± 2.8 [2] | −21.0 ± 14.1 [2] | +4.0 ± 3.0 [2] | — |
| | ≥60 | +0.1 ± 0.7 [17] | −3.2 ± 5.6 [10] | +5.2 1.4 [5] | −20.0 (28.7) [13] |
| ERT-Experienced | | | | | |
| Migalastat 0-18 months | 30 to <60 | −4.2 ± 2.7 [2] | −10.2 ± 2.4 [2] | +4.6 ± 2.3 [2] | +0.5 (0.6) [3] |
| | ≥60 | −0.4 ± 0.8 [32] | −4.8 ± 2.3 [24] | +5.5 ± 1.4 [12] | 1.9 (5.8) [28] |

As can be seen from Table 9, in the ERT-naïve study, plasma lyso-Gb$_3$ and LVMi decreased and WBC α-Gal A activity increased with migalastat at month 24 in both renal subgroups. Moreover, regardless of renal function, in the ERT-naïve study, there was a reduction in kidney interstitial capillary GL-3 inclusions from baseline to month 6 with migalastat (eGFR <60 mL/min/1.73 m$^2$, −0.39, n=3; eGFR ≥60 mL/min/1.73 m$^2$, −0.30, n=22) but not placebo (<60, 0.04, n=2; ≥60, 0.07, n=18). Table 9 also shows that in the ERT-experienced study, LVMi decreased, WBC α-Gal A activity increased, and lyso-Gb$_3$ remained low and stable during 18 months of treatment with migalastat in both subgroups. Table 9 also shows that renal function was stabilized in patients with a baseline eGFR ≥60 mL/min/1.73 m$^2$ in both the ERT-naïve and the ERT experienced study. This data further supports the efficacy of migalastat when administered to patients with some form of renal impairment.

In addition to the studies described above, other patients also received migalastat therapy in other studies such as dose-finding studies and/or long-term extension studies. Patients that completed the some studies were eligible to continue open-label migalastat HCl 150 mg every other day in a separate extension study.

12 patients that completed multiple studies were further analyzed. Linear regression was used to calculate the annualized rate of change in eGFR$_{CKD-EPI}$ from baseline. At the time of this analysis, mean time on migalastat for these 12 patients was 8.2 (standard deviation [SD], 0.83) years, the median time on treatment was 8.4 (range, 6.3-9.3) years, and 11 patients received migalastat HCl 150 mg QOD for ≥17 months. The baseline demographics for these 12 patients is shown in Table 10 below:

TABLE 10

| Patient | Age (years) | Sex | eGFR (mL/min/1.73 m$^2$) |
|---|---|---|---|
| 1 | 37 | M | 100.9 |
| 2 | 39 | M | 114.4 |
| 3 | 42 | M | 87.1 |
| 4 | 49 | M | 84.4 |
| 5 | 24 | M | 126.2 |
| 6 | 39 | M | 121.7 |
| 7 | 55 | M | 92.0 |
| 8 | 47 | M | 135.7 |
| 9 | 62 | F | 90.1 |
| 10 | 59 | F | 76.4 |
| 11 | 36 | F | 100.6 |
| 12 | 43 | F | 116.0 |
| Mean (SD) | 44.3 (10.7) | — | 103.8 (18.7) |
| Median (min, max) | 42.5 (24, 62) | — | 100.8 (76, 136) |

The annualized change in eGFR$_{CKD-EPI}$ for these patients is shown in Table 11 below:

TABLE 11

| Patient | Annualized Rate of Change in eGFR$_{CKD-EPI}$, mL/min/1.72 m$^2$ [a] |
|---|---|
| 1 | −0.853 |
| 2 | 0.584 |
| 3 | −2.838 |
| 4 | 0.488 |
| 5 | 0.001 |
| 6 | −2.179 |
| 7 | −0.704 |
| 8 | −1.09 |
| 9 | −0.443 |
| 10 | 0.219 |
| 11 | −0.342 |
| 12 | −0.871 |
| Mean (95% CI) | −0.67 (−1.32, −0.02) |

[a] Includes the entire duration of migalastat treatment, including periods when patients received various dosing regimens of migalastat and periods when patients received migalastat HCl 150 mg every other day As can be seen from Table 11, among these 12 patients, renal function remained stable (annualized mean change in eGFR$_{CKD-EPI}$, −0.67 mL/min/1.72 m$^2$ [95% CI −1.32, −0.02]) during the entire migalastat treatment period (mean exposure, 8.2 years). Renal function also remained stable (annualized mean change in eGFR$_{CKD-EPI}$, 0.24 mL/min/1.72 m$^2$ [95% CI −1.7, 2.2]) in an analysis of the 11 patients who received migalastat HCl 150 mg QOD for ≥17 months (mean exposure, 4-5 years). The renal outcomes for these 11 patients based on sex and baseline proteinuria levels are shown in Table 12 below:

TABLE 12

| Sex | Baseline 24-hour Urine Protein (mg/24 h) Category$^a$ | n | Annualized Rate of Change in eGFR$_{CKD-EPI}$, mL/min/1.73 m$^2$, Mean (95% CI) |
|---|---|---|---|
| All | All | 11 | +0.3 [−1.7, 2.2] |
| Males | <100 | 3 | +0.4 [−4.1, 4.9] |
| Males | 100-1000 | 4 | +2.4 [−4.0, 8.8] |
| Females | <100 | 2 | −1.6 [−2.4, −0.9] |
| Females | 100-1000 | 2 | −1.7 [−2.0, −1.3] |

These results show stabilization of renal function was demonstrated in male and female patients with Fabry disease and amenable mutations treated with migalastat for up to 9 years. The effects were observed over a wide baseline proteinuria range.

Another analysis was performed on patients who participated in multiple studies for the use of migalastat. Annualized change rate in eGFR$_{CKD-EPI}$ and eGFR$_{MDRD}$ were calculated for patients based on proteinuria at baseline (<100, 100-1000, >1000 mg/24 h). A total of 52 ERT-naïve patients with amenable mutations received migalastat HCl 150 mg QOD for ≥17 months were analyzed. Table 13 below shows the baseline proteinuria and duration of migalastat treatment for these patients.

TABLE 13

| Baseline 24 h urine protein, mg/24 h | Males | | Females | |
|---|---|---|---|---|
| | n | Duration, years, Median (min, max) | n | Duration, years, Median (min, max) |
| <100 | 3 | 4.8 (4.8, 4.8) | 9 | 4.2 (2.0, 5.3) |
| 100-1000 | 16 | 4.3 (1.5, 4.9) | 19 | 3.5 (1.5, 5.0) |
| >1000 | 2 | 3.6 (3.0, 4.3) | 3 | 3.7 (1.5, 4.1) |

As can be seen from Table 13, most patients (67%) had proteinuria levels between 100-1000 mg/24 h at baseline; 23% of patients had baseline proteinuria levels <100 mg/24 h, and 10% had levels >1000 mg/24 h. Median treatment duration ranged from 3.5 to 4.8 years (maximum, 5.3 years) across baseline proteinuria subgroups.

The annualized mean change in eGFR$_{CKD-EPI}$ with migalastat treatment by baseline proteinuria for these patients is shown in Table 14 below.

TABLE 14

| Baseline 24 h urine protein, mg/24 h | Males | | Females | |
|---|---|---|---|---|
| | n | Annualized eGFR$_{CKD-EPI}$ Change Rate, mL/min/1.73 m$^2$, Mean (SE) | n | Annualized eGFR$_{CKD-EPI}$ Change Rate, mL/min/1.73 m$^2$, Mean (SE) |
| <100 | 3 | 0.4 (1.0) | 9 | −0.9 (0.4) |
| 100-1000 | 16 | 0.2 (0.8) | 19 | −0.3 (1.0) |
| >1000 | 2 | −5.1 (0.1) | 3 | −2.2 (1.3) |

As can be seen from Table 14, eGFR$_{CKD-EPI}$ remained stable in most patients with baseline proteinuria ≤1000 mg/24 h during migalastat treatment. Declines in eGFR$_{CKD-EPI}$ were observed in patients with proteinuria levels >1000 mg/24 h at baseline.

Results for eGFR$_{MDRD}$ were compared with changes in eGFR$_{MDRD}$ reported in the literature for untreated patients with Fabry disease (natural history cohort; Schiffmann R et al. Nephrol Dial Transplant. 2009; 24:2102-11) and are shown in Table 15 below:

TABLE 15

| Baseline 24 h urine protein, mg/24 h | Males | | Females | |
|---|---|---|---|---|
| | n | Annualized eGFR Rate of Change, mL/min/m$^2$, Mean (SEM) | n | Annualized eGFR Rate of Change, mL/min/m$^2$, Mean (SEM) |
| Migalastat cohort | | | | |
| <100 | 3 | 1.2 (1.2) | 9 | −0.9 (0.5) |
| 100-1000 | 16 | 0.9 (1.0) | 19 | 1.3 (1.5) |
| >1000 | 2 | −4.3 (0.1) | 3 | −1.7 (1.1) |
| Natural history cohort (Schiffmann et al. 2009) | | | | |
| <100 | 18 | −1.6 (1.5) | 7 | −0.6 (2.6) |
| 100-1000 | 21 | −3.3 (1.8) | 17 | −2.2 (2.2) |
| >1000 | 22 | −6.9 (1.5) | 5 | −4.6 (2.3) |

As shown in Table 15, mean annualized change in eGFR was smaller overall in patients treated with migalastat versus that observed in the natural history cohort across proteinuria categories. While mean eGFR declined in all untreated subgroups, increases were seen with migalastat in patients with baseline proteinuria <100 mg/24 h (males) and 100-1000 mg/24 h (males and females). Regardless of treatment, eGFR decreased in patients with baseline proteinuria >1000 mg/24 h; however, patients treated with migalastat had smaller decreases compared to the natural history cohort. Thus, long-term migalastat treatment was generally associated with stable renal function in patients with Fabry disease and amenable mutations, regardless of baseline proteinuria levels.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating Fabry disease, the method comprising administering migalastat to a patient in need thereof, wherein the patient has an α-galactosidase A protein comprising a HEK assay amenable mutation selected from the group consisting of: R4M/Y207S, A15T, A15G, F18C, W24G, N34D, G35V, M42I, E48Q, N53D, P60S, F69L, M72I, G85S, G85N, G104V, L106F, A108T, D109G, R112G, G144D, L167V, L180W, G195V, R196G, V199A, E203D, P210S, P210L, P214S, R220P, Q221P, F229L, I242T, W245G, Q250H, p.V254del, G260E, G261S, G271S/D313Y, W277C, D299E, S304T, D313Y/G411D, I319F, F337S, P343L, G361A, P362T, K391T, G395E and p.T400_S401dup.

2. The method of claim 1, wherein the mutation is selected from the group consisting of: A15T, F18C, W24G, G35V, M42I, N53D, P60S, F69L, M72I, G104V, L106F, A108T, G144D, L167V, L180W, G195V, R196G, V199A, P210S, P210L, P214S, R220P, Q221P, F229L, I242T, W245G, Q250H, p.V254del, G260E, G261S, W277C, D299E, S304T, I319F, F337S, P343L, G361A, P362T and K391T.

3. The method of claim 1, wherein the mutation is selected from the group consisting of: N53D, P60S, L180W, R196G, P210S, P210L, P214S, R220P, Q221P, I242T, Q250H, p.V254del, G260E, G261S, D299E, S304T and P362T.

4. The method of claim 1, wherein the mutation is selected from the group consisting of: R4M/Y207S, A15T, A15G, W24G, G35V, M42I, E48Q, N53D, P60S, F69L, M72I, G85S, G85N, G104V, L106F, A108T, D109G, G144D, L167V, L180W, G195V, R196G, V199A, E203D, P210S, P210L, P214S, R220P, Q221P, F229L, I242T, W245G, Q250H, p.V254del, G260E, G261S, W277C, D299E, S304T, I319F, F337S, P343L, G361A, P362T, K391T, G395E and p.T400_S401dup.

5. The method of claim 1, wherein the mutation is selected from the group consisting of: R4M/Y207S, W24G, G35V, M42I, E48Q, N53D, P60S, F69L, G85S, G85N, G104V, L106F, D109G, G144D, L180W, G195V, R196G, E203D, P210S, P210L, P214S, R220P, Q221P, F229L, I242T, Q250H, p.V254del, G260E, G261S, W277C, D299E, S304T, I319F, F337S, G361A, P362T, K391T, G395E and p.T400_S401dup.

6. The method of claim 1, wherein the mutation is selected from the group consisting of: G35V, M42I, F69L and L180W.

7. The method of claim 1, wherein the mutation is selected from the group consisting of: A15T, W24G, G35V, M42I, N53D, P60S, F69L, M72I, G104V, L106F, A108T, G144D, L167V, L180W, G195V, R196G, V199A, P210S, P210L, P214S, R220P Q221P, F229L, I242T, W245G, Q250H, p.V254del, G260E, G261S, W277C, D299E, S304T, I319F, F337S, P343L, G361A, P362T and K391T.

8. The method of claim 1, wherein the mutation is selected from the group consisting of: W24G, G35V, M42I, N53D, P60S, F69L, G104V, L106F, G144D, L180W, G195V, R196G, P210S, P210L, P214S, R220P, Q221P, F229L, I242T, Q250H, p.V254del, G260E, G261S, W277C, D299E, S304T, I319F, F337S, G361A, P362T and K391T.

9. The method of claim 1, wherein the mutation is selected from the group consisting of: R4M/Y207S, A15T, A15G, F18C, W24G, N34D, G35V, M42I, E48Q, N53D, P60S, F69L, M72I, G85S, G85N, G104V, L106F, A108T, D109G, R112G, G144D, L167V, L180W, G195V, R196G, V199A, E203D, P210S, P210L, P214S, R220P, Q221P, F229L, I242T, W245G, Q250H, G260E, G261S, G271S/D313Y, W277C, D299E, S304T, D313Y/G411D, I319F, F337S, P343L, G361A, P362T, K391T and G395E.

10. The method of claim 1, wherein the mutation is selected from the group consisting of: R4M/Y207S, W24G, G35V, M42I, E48Q, N53D, P60S, F69L, G85S, G85N, G104V, L106F, D109G, G144D, L180W, G195V, R196G, E203D, P210S, P210L, P2145, R220P, Q221P, F229L, I242T, Q250H, G260E, G261S, W277C, D299E, S304T, I319F, F337S, G361A, P362T, K391T and G395E.

11. The method of claim 1, wherein the mutation is selected from the group consisting of: A15T, F18C, W24G, G35V, M42I, N53D, P60S, F69L, M72I, G104V, L106F, A108T, G144D, L167V, L180W, G195V, R196G, V199A, P210S, P210L, P214S, R220P, Q221P, F229L, I242T, W245G, Q250H, G260E, G261S, W277C, D299E, S304T, I319F, F337S, P343L, G361A, P362T and K391T.

12. The method of claim 1, wherein the mutation is selected from the group consisting of: N53D, P60S, L180W, R196G, P210S, P210L, P214S, R220P, Q221P, I242T, Q250H, G260E, G261S, D299E, S304T and P362T.

13. The method of claim 1, wherein the mutation is selected from the group consisting of: W24G, G35V, M42I, N53D, P60S, F69L, G104V, L106F, G144D, L180W, G195V, R196G, P210S, P210L, P214S, R220P, Q221P, F229L, I242T, Q250H, G260E, G261S, W277C, D299E, S304T, I319F, F337S, G361A, P362T and K391T.

14. The method of claim 1, wherein the patient has a Fabry disease-causing mutation.

15. The method of claim 1, wherein the migalastat or salt thereof is administered to the patient every other day.

16. The method of claim 1, wherein the patient is administered about 123 to about 300 mg of the migalastat or salt thereof every other day.

17. The method of claim 1, wherein the patient is administered about 150 mg of the migalastat or salt thereof every other day.

18. The method of claim 1, wherein the patient is administered about 150 mg of migalastat hydrochloride every other day.

19. The method of claim 1, wherein the patient is male.

20. The method of claim 1, wherein the patient is female.

21. The method of claim 1, wherein the patient has renal impairment.

22. The method of claim 21, wherein the patient has mild or moderate renal impairment.

23. The method of claim 1, wherein the patient is an enzyme replacement therapy (ERT)-experienced patient.

24. The method of claim 1, wherein the patient is an enzyme replacement therapy (ERT)-experienced patient with renal impairment.

25. The method of claim 1, wherein the patient is an enzyme replacement therapy (ERT)-naïve patient.

26. The method of claim 1, wherein the patient has a proteinuria level of less than 100 mg/24 hr prior to initiating the administration of the migalastat or salt thereof.

27. The method of claim 1, wherein the patient has a proteinuria level of 100 to 1,000 mg/24 hr prior to initiating the administration of the migalastat or salt thereof.

28. The method of claim 1, wherein the patient has a proteinuria level of greater than 1,000 mg/24 hr prior to initiating the administration of the migalastat or salt thereof.

29. The method of claim 1, wherein the migalastat or salt thereof is administered orally.

30. The method of claim 29, wherein the migalastat or salt thereof is in a solid dosage form.

31. The method of claim 30, wherein the solid dosage form comprises a capsule.

32. The method of claim 1, wherein the migalastat is administered as a pharmaceutically acceptable salt.

33. The method of claim 1, wherein the patient is orally administered a capsule comprising about 150 mg of migalastat hydrochloride every other day.

34. The method of claim 8, wherein the patient has a Fabry disease-causing mutation.

35. The method of claim 8, wherein the migalastat or salt thereof is administered to the patient every other day.

36. The method of claim 8, wherein the patient is administered about 123 to about 300 mg of the migalastat or salt thereof every other day.

37. The method of claim 8, wherein the patient is administered about 150 mg of the migalastat or salt thereof every other day.

38. The method of claim 8, wherein the patient is administered about 150 mg of migalastat hydrochloride every other day.

39. The method of claim 8, wherein the patient is male.

40. The method of claim 8, wherein the patient is female.

41. The method of claim 8, wherein the patient has renal impairment.

42. The method of claim 41, wherein the patient has mild or moderate renal impairment.

43. The method of claim 8, wherein the patient is an enzyme replacement therapy (ERT)-experienced patient.

44. The method of claim 8, wherein the patient is an enzyme replacement therapy (ERT)-experienced patient with renal impairment.

45. The method of claim 8, wherein the patient is an enzyme replacement therapy (ERT)-naïve patient.

46. The method of claim 8, wherein the patient has a proteinuria level of less than 100 mg/24 hr prior to initiating the administration of the migalastat or salt thereof.

47. The method of claim 8, wherein the patient has a proteinuria level of 100 to 1,000 mg/24 hr prior to initiating the administration of the migalastat or salt thereof.

48. The method of claim 8, wherein the patient has a proteinuria level of greater than 1,000 mg/24 hr prior to initiating the administration of the migalastat or salt thereof.

49. The method of claim 8, wherein the migalastat or salt thereof is administered orally.

50. The method of claim 49, wherein the migalastat or salt thereof is in a solid dosage form.

51. The method of claim 50, wherein the solid dosage form comprises a capsule.

52. The method of claim 8, wherein the migalastat is administered as a pharmaceutically acceptable salt.

53. The method of claim 8, wherein the patient is orally administered a capsule comprising about 150 mg of migalastat hydrochloride every other day.

54. The method of claim 1, wherein the administration is effective to reduce globotriaosylceramide (GL-3) accumulated in an organ of the patient.

55. The method of claim 1, wherein the administration is effective to reduce plasma globotriaosylsphingosine (lyso-Gb3) in the patient.

56. The method of claim 1, wherein the administration is effective to increase white blood cell (WBC) α-galactosidase A activity in the patient.

57. The method of claim 1, wherein the administration is effective to reduce left ventricular mass index (LVMi) in the patient.

58. The method of claim 1, wherein the administration is effective to stabilize renal function in the patient.

59. The method of claim 1, wherein the administration is effective to (i) reduce globotriaosylceramide (GL-3) accumulated in an organ of the patient, (ii) reduce plasma globotriaosylsphingosine (lyso-Gb3) in the patient, (iii) increase white blood cell (WBC) α-galactosidase A activity in the patient, (iv) reduce left ventricular mass index (LVMi) in the patient, or (v) stabilize renal function in the patient.

60. A molecule comprising migalastat bound to an a-galactosidase A protein comprising a HEK assay amenable mutation selected from the group consisting of: R4M/ Y207S, A15T, A15G, F18C, W24G, N34D, G35V, M42I, E48Q, N53D, P60S, F69L, M72I, G85S, G85N, G104V, L106F, A108T, D109G, R112G, G144D, L167V, L180W, G195V, R196G, V199A, E203D, P210S, P210L, P214S, R220P, Q221P, F229L, I242T, W245G, Q250H, p.V254del, G260E, G261S, G271S/D313Y, W277C, D299E, S304T, D313Y/G411D, I319F, F337S, P343L, G361A, P362T, K391T, G395E and p.T400_S401dup.

61. The molecule of claim 60, wherein the mutation is selected from the group consisting of: A15T, F18C, W24G, G35V, M42I, N53D, P60S, F69L, M72I, G104V, L106F, A108T, G144D, L167V, L180W, G195V, R196G, V199A, P210S, P210L, P214S, R220P, Q221P, F229L, I242T, W245G, Q250H, p.V254del, G260E, G261S, W277C, D299E, S304T, I319F, F337S, P343L, G361A, P362T and K391T.

62. The molecule of claim 60, wherein the mutation is selected from the group consisting of: N53D, P60S, L180W, R196G, P210S, P210L, P214S, R220P, Q221P, I242T, Q250H, p.V254del, G260E, G261S, D299E, S304T and P362T.

63. The molecule of claim 60, wherein the mutation is selected from the group consisting of: R4M/Y207S, A15T, A15G, W24G, G35V, M42I, E48Q, N53D, P60S, F69L, M72I, G85S, G85N, G104V, L106F, A108T, D109G, G144D, L167V, L180W, G195V, R196G, V199A, E203D, P210S, P210L, P214S, R220P, Q221P, F229L, I242T, W245G, Q250H, p.V254del, G260E, G261S, W277C, D299E, S304T, I319F, F337S, P343L, G361A, P362T, K391T, G395E and p.T400_S401dup.

64. The molecule of claim 60, wherein the mutation is selected from the group consisting of: R4M/Y207S, W24G, G35V, M42I, E48Q, N53D, P60S, F69L, G85S, G85N, G104V, L106F, D109G, G144D, L180W, G195V, R196G, E203D, P210S, P210L, P214S, R220P, Q221P, F229L, I242T, Q250H, p.V254del, G260E, G261S, W277C, D299E, S304T, I319F, F337S, G361A, P362T, K391T, G395E and p.T400_S401dup.

65. The molecule of claim 60, wherein the mutation is selected from the group consisting of: G35V, M42I, F69L and L180W.

66. The molecule of claim 60, wherein the mutation is selected from the group consisting of: A15T, W24G, G35V, M42I, N53D, P60S, F69L, M72I, G104V, L106F, A108T, G144D, L167V, L180W, G195V, R196G, V199A, P210S, P210L, P214S, R220P, Q221P, F229L, I242T, W245G, Q250H, p.V254del, G260E, G261S, W277C, D299E, S304T, I319F, F337S, P343L, G361A, P362T and K391T.

67. The molecule of claim 60, wherein the mutation is selected from the group consisting of: W24G, G35V, M42I, N53D, P60S, F69L, G104V, L106F, G144D, L180W, G195V, R196G, P210S, P210L, P214S, R220P, Q221P, F229L, I242T, Q250H, p.V254del, G260E, G261S, W277C, D299E, S304T, I319F, F337S, G361A, P362T and K391T.

68. The molecule of claim 60, wherein the mutation is selected from the group consisting of: R4M/Y207S, A15T, A15G, F18C, W24G, N34D, G35V, M42I, E48Q, N53D, P60S, F69L, M72I, G85S, G85N, G104V, L106F, A108T, D109G, R112G, G144D, L167V, L180W, G195V, R196G, V199A, E203D, P210S, P210L, P214S, R220P, Q221P, F229L, I242T, W245G, Q250H, G260E, G261S, G271S/ D313Y, W277C, D299E, S304T, D313Y/G411D, I319F, F337S, P343L, G361A, P362T, K391T and G395E.

69. The molecule of claim 60, wherein the mutation is selected from the group consisting of: R4M/Y207S, W24G, G35V, M42I, E48Q, N53D, P60S, F69L, G85S, G85N, G104V, L106F, D109G, G144D, L180W, G195V, R196G, E203D, P210S, P210L, P214S, R220P, Q221P, F229L, I242T, Q250H, G260E, G261S, W277C, D299E, S304T, I319F, F337S, G361A, P362T, K391T and G395E.

70. The molecule of claim 60, wherein the mutation is selected from the group consisting of: A15T, F18C, W24G, G35V, M42I, N53D, P60S, F69L, M72I, G104V, L106F, A108T, G144D, L167V, L180W, G195V, R196G, V199A, P210S, P210L, P214S, R220P, Q221P, F229L, I242T, W245G, Q250H, G260E, G261S, W277C, D299E, S304T, I319F, F337S, P343L, G361A, P362T and K391T.

71. The molecule of claim 60, wherein the mutation is selected from the group consisting of: N53D, P60S, L180W, R196G, P210S, P210L, P214S, R220P, Q221P, I242T, Q250H, G260E, G261S, D299E, S304T and P362T.

72. The molecule of claim 60, wherein the mutation is selected from the group consisting of: W24G, G35V, M42I, N53D, P60S, F69L, G104V, L106F, G144D, L180W, G195V, R196G, P210S, P210L, P214S, R220P, Q221P, F229L, I242T, Q250H, G260E, G261S, W277C, D299E, S304T, I319F, F337S, G361A, P362T and K391T.

73. An α-galactosidase A protein having a HEK amenable mutation selected from the group consisting of: R4M/ Y207S, A15T, A15G, F18C, W24G, N34D, G35V, M42I, E48Q, N53D, P60S, F69L, M72I, G85S, G85N, G104V, L106F, A108T, D109G, R112G, G144D, L167V, L180W, G195V, R196G, V199A, E203D, P210S, P210L, P214S, R220P Q221P, F229L, I242T, W245G, Q250H, p.V254del, G260E, G261S, G271S/D313Y, W277C, D299E, S304T, D313Y/G411D, I319F, F337S, P343L, G361A, P362T, K391T, G395E and p.T400_S401dup, wherein the protein is bound to migalastat and the protein has increased stability as compared to a naturally-occurring a-galactosidase A protein having the same mutation.

74. The α-galactosidase A protein of claim 73, wherein the mutation is selected from the group consisting of: A15T, F18C, W24G, G35V, M42I, N53D, P60S, F69L, M72I, G104V, L106F, A108T, G144D, L167V, L180W, G195V, R196G, V199A, P210S, P210L, P214S, R220P, Q221P, F229L, I242T, W245G, Q250H, p.V254del, G260E, G261S, W277C, D299E, S304T, I319F, F337S, P343L, G361A, P362T and K391T.

75. The α-galactosidase A protein of claim 73, wherein the mutation is selected from the group consisting of: N53D, P60S, L180W, R196G, P210S, P210L, P214S, R220P, Q221P, I242T, Q250H, p.V254del, G260E, G261S, D299E, S304T and P362T.

76. The α-galactosidase A protein of claim 73, wherein the mutation is selected from the group consisting of: R4M/Y207S, A15T, A15G, W24G, G35V, M42I, E48Q, N53D, P60S, F69L, M72I, G85S, G85N, G104V, L106F, A108T, D109G, G144D, L167V, L180W, G195V, R196G, V199A, E203D, P210S, P210L, P214S, R220P, Q221P, F229L, I242T, W245G, Q250H, p.V254del, G260E, G261S, W277C, D299E, S304T, I319F, F337S, P343L, G361A, P362T, K391T, G395E and p.T400_S401dup.

77. The α-galactosidase A protein of claim 73, wherein the mutation is selected from the group consisting of: R4M/Y207S, W24G, G35V, M42I, E48Q, N53D, P60S, F69L, G85S, G85N, G104V, L106F, D109G, G144D, L180W, G195V, R196G, E203D, P210S, P210L, P214S, R220P, Q221P, F229L, I242T, Q250H, p.V254del, G260E, G261S, W277C, D299E, S304T, I319F, F337S, P343L, G361A, P362T, K391T, G395E and p.T400_S401dup.

78. The α-galactosidase A protein of claim 73, wherein the mutation is selected from the group consisting of: G35V, M42I, F69L and L180W.

79. The α-galactosidase A protein of claim 73, wherein the mutation is selected from the group consisting of: A15T, W24G, G35V, M42I, N53D, P60S, F69L, M72I, G104V, L106F, A108T, G144D, L167V, L180W, G195V, R196G, V199A, P210S, P210L, P214S, R220P, Q221P, F229L, I242T, W245G, Q250H, p.V254del, G260E, G261S, W277C, D299E, S304T, I319F, F337S, P343L, G361A, P362T and K391T.

80. The α-galactosidase A protein of claim 73, wherein the mutation is selected from the group consisting of: W24G, G35V, M42I, N53D, P60S, F69L, G104V, L106F, G144D, L180W, G195V, R196G, P210S, P210L, P214S, R220P, Q221P, F229L, I242T, Q250H, p.V254del, G260E, G261S, W277C, D299E, S304T, I319F, F337S, P343L, G361A, P362T and K391T.

81. The α-galactosidase A protein of claim 73, wherein the mutation is selected from the group consisting of: R4M/Y207S, A15T, A15G, F18C, W24G, N34D, G35V, M42I, E48Q, N53D, P60S, F69L, M72I, G85S, G85N, G104V, L106F, A108T, D109G, R112G, G144D, L167V, L180W, G195V, R196G, V199A, E203D, P210S, P210L, P214S, R220P Q221P, F229L, I242T, W245G, Q250H, G260E, G261S, G271S/D313Y, W277C, D299E, S304T, D313Y/G411D, I319F, F337S, P343L, G361A, P362T, K391T and G395E.

82. The α-galactosidase A protein of claim 73, wherein the mutation is selected from the group consisting of: R4M/Y207S, W24G, G35V, M42I, E48Q, N53D, P60S, F69L, G85S, G85N, G104V, L106F, D109G, G144D, L180W, G195V, R196G, E203D, P210S, P210L, P214S, R220P, Q221P, F229L, I242T, Q250H, G260E, G261S, W277C, D299E, S304T, I319F, F337S, P343L, G361A, P362T, K391T and G395E.

83. The α-galactosidase A protein of claim 73, wherein the mutation is selected from the group consisting of: A15T, F18C, W24G, G35V, M42I, N53D, P60S, F69L, M72I, G104V, L106F, A108T, G144D, L167V, L180W, G195V, R196G, V199A, P210S, P210L, P214S, R220P, Q221P, F229L, I242T, W245G, Q250H, G260E, G261S, W277C, D299E, S304T, I319F, F337S, P343L, G361A, P362T and K391T.

84. The α-galactosidase A protein of claim 73, wherein the mutation is selected from the group consisting of: N53D, P60S, L180W, R196G, P210S, P210L, P214S, R220P, Q221P, I242T, Q250H, G260E, G261S, D299E, S304T and P362T.

85. The α-galactosidase A protein of claim 73, wherein the mutation is selected from the group consisting of: W24G, G35V, M42I, N53D, P60S, F69L, G104V, L106F, G144D, L180W, G195V, R196G, P210S, P210L, P214S, R220P, Q221P, F229L, I242T, Q250H, G260E, G261S, W277C, D299E, S304T, I319F, F337S, P343L, G361A, P362T and K391T.

86. The method of claim 1, wherein the mutation is selected from the group consisting of: A15T, A15G, F18C, E48Q, F69L, G104V, L106F, A108T, D109G, L167V, G195V, R196G, P210S, P210L, Q221P, F229L, W245G, D299E, F337S, P343L and K391T.

87. The molecule of claim 60, wherein the mutation is selected from the group consisting of: A15T, A15G, F18C, E48Q, F69L, G104V, L106F, A108T, D109G, L167V, G195V, R196G, P210S, P210L, Q221P, F229L, W245G, D299E, F337S, P343L and K391T.

88. The α-galactosidase A protein of claim 73, wherein the mutation is selected from the group consisting of: A15T, A15G, F18C, E48Q, F69L, G104V, L106F, A108T, D109G, L167V, G195V, R196G, P210S, P210L, Q221P, F229L, W245G, D299E, F337S, P343L and K391T.

89. The method of claim 1, wherein the mutation is selected from the group consisting of: N34D, M42I, R196G, V199A, E203D, p. V254del and G260E.

90. The method of claim 1, wherein the mutation is N34D.

91. The method of claim 1 wherein the mutation is M42I.

92. The method of claim 1 wherein the mutation is R196G.

93. The method of claim 1 wherein the mutation is V199A.

94. The method of claim 1 wherein the mutation is E203D.

95. The method of claim 1 wherein the mutation is V254del.

96. The method of claim 1 wherein the mutation is G260E.

97. The method of claim 1, wherein the mutation is selected from the group consisting of: R196G, p. V254del and G260E.

* * * * *

SEQUENCE LISTING

<160> NUMBER OF SEQ ID NOS: 2

<210> SEQ ID NO 1
<211> LENGTH: 12436
<212> TYPE: DNA
<213> ORGANISM: Homo sapiens

<400> SEQUENCE: 1

| | | | | | | |
|---|---|---|---|---|---|---|
| cccttctgta | ggggcagaga | ggttctactt | cattactgcg | tctcctggga | aggccatcag | 60 |
| gactgctggc | taaagtggga | accaggactc | tttgtgagtt | aagaatttgt | gtatttatat | 120 |
| gtgtgttata | cacattttt | aaaaaactgt | aacgacatca | ggttgagcag | tcgtctccgg | 180 |
| gtggtgaatt | atgtgtattt | ttaaattta | tactatattg | ttattttca | aatgttcgaa | 240 |
| attgaatatg | tagattgttg | ttatcagcag | aaaaataaac | attattcaaa | tactctattc | 300 |
| agtaaagtaa | tttattgggc | gcctttgtca | agcacgcatt | tgcctagatg | tgactctaca | 360 |
| gataaaattc | acttggggcc | tccccttaca | gacaatcagg | cagtggagac | tgagtgcctg | 420 |
| aatggataga | ccagcactca | gaccactatt | ttcagtatct | gtttttctta | actcagggcc | 480 |
| gtggttttca | aacgttttc | gccttacggt | cacccttagg | gtcccccgag | accggcccag | 540 |
| acagacagat | atacaaaaac | acatacacag | tcatgagcgt | ccaccatttc | cccaccaggc | 600 |
| gcagcacagg | cggcttcccg | gcactgagat | gggggggagg | agggagagag | cgcgaggggg | 660 |
| gaggggaaag | cagagaacga | agaggcggca | gcggccccc | gaaccccgct | ctggtcttca | 720 |
| tcatcaccac | ccctgggtcc | ccagttccca | cccacacacc | aacctctaac | gataccgggt | 780 |
| aatttcctc | cttcttccct | caaacggcta | tagcgagacg | tagacgacg | accagaacta | 840 |
| cttctgctca | cgtaagcgag | taatcacgtg | agcgcctacg | tcatgtgaga | tctcggtcac | 900 |
| gtgagcaact | ctcggcttaa | actcgggatc | actaaggtgc | cgcacttcct | tctggtatgg | 960 |
| aaatagggcg | ggtcaatatc | aagaaaggaa | gagggtgatt | ggttagcgga | acgtcttacg | 1020 |
| tgactgatta | ttggtctacc | tctggggata | accgtcccag | ttgccagaga | aacaataacg | 1080 |
| tcattattta | ataagtcatc | ggtgattggt | ccgcccctga | ggttaatctt | aaaagcccag | 1140 |
| gttacccgcg | gaaatttatg | ctgtccggtc | accgtgacaa | tgcagctgag | gaacccagaa | 1200 |
| ctacatctgg | gctgcgcgct | tgcgcttcgc | ttcctggccc | tcgtttcctg | ggacatccct | 1260 |
| ggggctagag | cactggacaa | tggattggca | aggacgccta | ccatgggctg | gctgcactgg | 1320 |
| gagcgcttca | tgtgcaacct | tgactgccag | gaagagccag | attcctgcat | caggtatcag | 1380 |
| atattgggta | ctcccttccc | tttgcttttc | catgtgtttg | ggtgtgtttg | gggaactgga | 1440 |
| gagtctcaac | gggaacagtt | gagcccgagg | gagagctccc | ccacccgact | ctgctgctgc | 1500 |
| ttttttatcc | ccagcaaact | gtcccgaatc | aggactagcc | ctaaactttc | tctgtgtgac | 1560 |
| ctttcctggg | atgggagtcc | ggccagcggc | ccctgtttct | ttctctctct | ctctctctct | 1620 |
| cgttctcctt | ctctttctct | ttctcttctt | tcctctctct | ttctctctct | ccctgcccgg | 1680 |
| ttctctttt | tcactgctcc | ttgcagagca | gggccacccc | ataggcagtg | tgcccaaagt | 1740 |
| agccctgccc | ggttctattc | agaccttct | tgtgaacttc | tgctcttcct | ctgccgggtg | 1800 |
| ctaaccgtta | gaacatctag | ggtgggtagg | aggaatgggg | aactaagatt | cgtgccattt | 1860 |
| tttctccttt | tggggtcgtg | gatttctcgg | cagtatctcg | agggagttag | agagaccata | 1920 |
| aggtcgctga | gatctctccc | acctcgccca | tgagcgtggc | atcaggctgg | aaggttgaca | 1980 |
| tggaggaact | ttatacattt | acacctttgc | gtgagggttg | aggctggatt | agataggtat | 2040 |
| tgaacatatc | tgaccctcac | aatccttatc | tgtaaattgg | gattacaacc | ttttaatttc | 2100 |

```
agggagctga caaaaaaaat ctgaaaaata gttcttatct cacacaggtg agttttcaag      2160
gagataacct atttaaagta catagcacag cgcttgacca ttcaactgcg cttacagagc      2220
aaatgttcaa tgggaaaatg aatgtaaatc tacaaatctg aatgaatatg tgtattttc      2280 tggagagagg atatttacct ttcttcaaat tctcaagggg ctctgtgatt taaaaaaggt      2340
taggaatcac tgatagatgt tggtaaaagg tggcagtcac agtacatttc tgtgtccata      2400
agttattcct atgaatatct ttatagataa agtcaggatg ttggtcagac atcacagaag      2460
aaattggcct tgtaagtttc atgtgaccct gtggtacagt atgtgtggca attttgccca      2520
tcacggattt ttttttattg gtatttgcat ctgattataa aactaatgca tgatcattgc      2580
aaaaaatgta gataaagaag agcaaaatga aaataaagat ttccccccac cgttccacca      2640
cccagaaata atcatggttt aaatgttaat atacaacctt acaattgttt tctatataaa      2700
tgaaaacata gatttcttta tttcattatt ttccataaaa aatggatcat gtttatgtca      2760
tgtttggcta atggcaagac cctggcaccc agtctgggct caaattctgc ctcattgtta      2820
cttagccctg tgacattggg taaattacac tttttttttt tttttttttt tgagacgggg      2880
tctcgctctg tcgcccaggc tggagtgcag tggcacgatc tcggctcact gcaagtccgc      2940
ctcctgggtt cacgccattc ttctgcctca gcctcccgag tagctgggac tacaggcgcc      3000
tgccaccacg cctggctctt tttttttttt tttttttttt tagtacagac ggggtttcac      3060
catgttagcc agggtggtct caatctcctg acctcgtgat tcgcccgcct cagcctccca      3120
aagtgctggt gtgagccacc gtgcccagcc ttactttttt ttttgagagg gggtctcact      3180
ctgtcaccca ggttggagtg cagtggcgcg atctctgctc agtgcaaact ccacctcccg      3240
ggtttaagca gttctcctgt cgtagtctcc tgagtagctg ggattacagg cacaccacca      3300
cggccagcta atttttgtat tttcagtaga gacgggtttc accatgttgc ccaagctggt      3360
ctcgaactcc tggcctcaag tgatctgccc gccttggcct cccagagtgc tgggattaca      3420
ggtgtgagcc accgcacccg gcctcttttt tcttttttag tctatcatac cttgcaaata      3480
cagtggttct tcctatgtgt tggttttgat atttatgtaa tcaaacacat cagttttcc      3540 tttctgattt ctgactttgg ggtcatgctg agaaagtcct ttcctacctg aagataatac      3600
agtatatacg tttcttacta gtattttgt ggatttttaa aatatttaaa tctttagtcc      3660
atctgaactt gttcttctat cagaaatgcc acatttaata aataataagt cccatgtgtat      3720 cagatggctg gaaggacctc tttcgaaact ttgtttaatt ccattaatct gtgtattctt      3780
attctaatgc taatagttcc acactagctt cctttatctt tttttttctt tttttttt      3840 ttttgagctg gagtttcgct cttgttgccc aggctggagt acaatgtcac gatctcggtt      3900
caccgcaacc tccgcctccc aggttcaagc aattctcctg cctcatcctc gcgagtagct      3960
ggaattacag gcatgcgcca ccacgcctag ctattttgta ttttagtag agatgggtt      4020 tctccatgtt ggtcaggctg gtctcaaact cccagcctca ggtgatctgc ctgcctcggc      4080
ctcccaaaat gctgttatta caggcgtgag ccaccacgcc cagccttcat cttttaatga      4140
atgtacatgt atgtaatctt ttaggtgaac ttttttgtaat gttgtgccaa gttccttaaa      4200 aagcccttttt ggaagctggg caggtggcca cgcctgtaat cccagcattt tgggagtctg      4260
aggcaggtgg atcacttgag gccaggagtt caagactagc ctagccaaaa tgcaaaaccc      4320
tgtctctact aaagatacaa aaattagccg gatgcgatgg cacatgcctg taatctcagc      4380
tactcgggag gctgaggtag aagaatcgct tgaaccgggg aggcagaggt tgcagtgagc      4440
```

```
aagatggcgc cactgcactc cagcctgggt gacagaggga gactccatct caaaaaaaaa    4500
aaaaaaaaaa aagataaaaa ggaaacctaa gtactcttgg gctttgttaa ggattttgtt    4560
aaatatacaa aggattgcag ggaaaattaa cttattttta atattgagta tgcttatcca    4620
agagcaaaat aatatttctc catttattca aatcatttag gagcatcata gttttaacat    4680
atgggccttg cacgtatctt aaatttatct ctaggcattt taggttgttc agttgttctt    4740
gtgaatggga tcttttttctc caaataggat tattgttgat atctgttgat tatgttaact    4800
ttgtagtttc tgactttact gaactgtctt cttagatcta atactctttt caatttcatc    4860
atatatttct cattcctatt tgtttgggg ttttagggc gggaatatta acgggataag    4920
agagacaaaa gaaaatctgg aaaaacaatt cattttacct tacattgctt gtgattacta    4980
ccacactatt actgggttgg aaaaaattgt gaaatcccaa ggtgcctaat aaatgggagg    5040
tacctaagtg ttcatttaat gaattgtaat gattattgga atttctcttt cagtgagaag    5100
ctcttcatgg agatggcaga gctcatggtc tcagaaggct ggaaggatgc aggttatgag    5160
tacctctgca ttgatgactg ttggatggct ccccaaagag attcagaagg cagacttcag    5220
gcagaccctc agcgctttcc tcatgggatt cgccagctag ctaattatgt gagtttatag    5280
ataatgttct tgttcattca gaggactgta agcacttctg tacagaagct tgtttagaaa    5340
cagccctcat ggccgggcgt ggtggctcac gctgtaatcc caacactttg ggaggccgag    5400
gcgggtggat cacctgaggt caagagttca agaccagcct ggccaacatg gtgaaacccc    5460
aactctatta aaagtacaaa aaattagctg gcatggtgg tgaacgcctg taaccccagc    5520
tacttgggag gctgaggcag gagaatcgct tgaacccagg aggtggaagt ttcagtgagc    5580
tgagatcacg ccattgcact ctagcctggg caacaaaaga gaaactccat ctcaaaaaaa    5640
aaaacaagga aaaaagaaa cagccctcat gacacttaga aagtagaata gctggctgtt    5700
atctgaacat tgaattgtaa ggcttatcag gtggactttg cattccatca gcagacaatt    5760
tttttttttt tttttttttg agatggagtc tcattctgtc tcccaggctg gagggcagtg    5820
gtgcgatctc ggctcactgc aagctccacc tcctgggttc atgccattct cctgcctcag    5880
cctcccaagt agctgggacc acaggcaccc gccaccatgc ccagttaatt ttttgtattt    5940
ttagtagaga cggggtttca ccatgttagc caagatggtc tcgatctcct gacctcgtga    6000
tccgcccacc tcggcctccc aaagtgctgg gattacaggc atgagccacc gcgcctagcc    6060
tacaaatgtt ttgtaatagc tcttgaggcc catcttggag ttctccttttt gctaaaacca    6120 ctgaactctc taggaggaaa aaggaacttg gttcttgaca tatgtgtgca tgtatttcca    6180
tataaccttt aggaagctat tgcaatggta ctataaacta gaattttaga agatagaagg    6240
aaaatattct ggagatcatt gaagagaaat ggagtccaac actagttaaa gatgatgaag    6300
acagattttt tttttttgacg gagtctcgct ctgtcgccca ggctggagtg cagtggcaca    6360
atctcagctc actgcaaccc tccacctctt gggttcaagt gattctcctg cctcagcctc    6420
ccaagtagct gggactacag gcgcacacca ccacgcccgg ctaattttg tattttttagt    6480 agagacaagg tttcaccata ttcgccaggc tggtctcgaa ctcctgacct tgtaatccgc    6540
ccaccttggc ctcccaaagt gctgggatta caggcatgag ccaccacgcc cggccgatga    6600
agacagattt tattcagtac taccacagta gaggaaagag ccaagttcaa ttccaaatac    6660
aacaaagaca ggtggagatt tatagccaat gagcagattg aggggtcag tggatggaat    6720 atttaagaag acatcaaggg tagggagctt cttgctaaag cttcatgtac ttaaacaaga    6780
agggtggggg atgagggaaa ttgatcagat atcaatggtg gcagtattga cttagcagga    6840
```

```
ttcttgctaa gaggtcttgc taggacagac ataggaagcc aaggtggagg tctagtcgaa    6900
aagaaggctc atcagagaag tctaactaaa gtttggtcaa gaagagtctt tgtcaaggta    6960
aatctatcat ttccctcaaa aggtaatttt caggatccca tcaggaagat tagcatggct    7020
gctagctttc tcctcagttc tgggctatag ctcacatgcc tagtttgaac tagctcagca    7080
gaactggggg atttattctt tgtcttccaa caaactcatc tggatgattt tgggggtttg    7140 tgggaaaag cccccaatac ctggtgaagt aaccttgtct cttcccccag cctggaatgg    7200
ttctctcttt ctgctacctc acgattgtgc ttctacaatg gtgactcttt tcctccctct    7260
catttcaggt tcacagcaaa ggactgaagc tagggattta tgcagatgtt ggaaataaaa    7320
cctgcgcagg cttccctggg agttttggat actacgacat tgatgcccag acctttgctg    7380
actggggagt agatctgcta aaatttgatg gttgttactg tgacagtttg gaaaatttgg    7440
cagatggtaa tgtttcattc cagagattta gccacaaagg aaagaacttt gaggccatgg    7500
tagctgagcc aaagaaccaa tcttcagaat tttaaatacc ctgtcacaat actggaaata    7560
attattctcc atgtgccaga gctcccatct cttctctttc agttcattaa ttaattaatt    7620
aattcatgta aaatccatgc atacctaacc atagctaata ttgtgcactt ataattcaag    7680
agggctctaa gagttaatta gtaattgtaa ctctctataa catcatttag gggagtccag    7740
gttgtcaatc ggtcacagag aaagaagcat cttcattcct gcctttcctc aatatacaca    7800
ccatctctgc actacttcct cagaacaatc ccagcagtct gggaggtact ttacacaatt    7860
taagcacaga gcaactgcct gtccctgctg ctagtttaaa catgaacctt ccaggtagcc    7920
tcttcttaaa atatacagcc ccagctgggc atgatggctc atgcctgtaa tcctagcact    7980
ttgggaggct gaggcgggtg gattacttga ggtcaggagt tcgagaccac cctggccaac    8040
atggtgaaac cccatctcta gtaaaaatac aaaaattagc tgactttggt ggcacatgcc    8100
tgtaatccca gctacttggg aagctgagac agaagagtca cttgaacctg ggaaacagag    8160
gttgcagtga gccaagatcg caccactgca ctccaccctg gatgacagac tgaacccccat    8220 ctcaaaaaat taaaataaaa taaaataaaa taactatata tatagcccca gctggaaatt    8280
catttctttc ccttatttta cccattgttt tctcatacag gttataagca catgtccttg    8340
gccctgaata ggactggcag aagcattgtg tactcctgtg agtggcctct ttatatgtgg    8400 cccttttcaaa aggtgagata gtgagcccag aatccaatag aactgtactg atagatagaa    8460
cttgacaaca aaggaaacca aggtctcctt caaagtccaa cgttacttac tatcatccta    8520
ccatctctcc caggttccaa ccacttctca ccatccccac tgctgtaatt atagcctaag    8580
ctaccatcac ctggaaagtc atccttgtgt cttcccctttt atttccaccat tcatgtcctg    8640 tctatcaaca gtccttccac cagtatctct aaaatatctc ctgaatcagc ccacttcctt    8700
ccatcttcac tacatgcacc ctggccttcc aagctactat cggctctcaa ccagactgct    8760
gggaccacct gatctctctg cttccactct gtctcaaccc ccatctattt tccaagcagc    8820
actagagtta tcatattaaa atgtaaatat cagtttttttt tttaaagaaa aaaccctga    8880 gacttaacag agttataaaa aatataaatg tcatcatcag ttccctgctt aaaacccttta    8940 actcgcttcc aattgcactt ggaatgaaac caaactgcac tgatccagcc cttgcctgcc    9000
tccccaaagt ccaagggggt atggctcttt ccctggctac actggttttc tttctgtccc    9060
tcaacactgc aagcctattg ctgccccagg gcctttacac ttgcttttttt tctgcctaga    9120 acagttcttc cccaaagatt tttaagggggc cgggctcctt aacattgaag tcgcagacca    9180
```

-continued

```
aacgccacat atgcagacag ttcttctcta actactttaa aatagccctc tgtccattca      9240
ttcttcatca cattaacctg tttaattttc ttctcagagc tccacactat ttggaagtat      9300
ttgttgactt gttaccatgt ctccccacta gagtgtaagt ttcatgaggg cagggacctt      9360
gtctgacttt gactgtatct ctcgcatatg gttaagtgtt aaatagttat ttatggaatg      9420
aatccctatt attccctcat tatctctgca aaatagtctt ttttctcaac atcttaaacc      9480
tgatatccca cctgcctatc tacaaacttt ttttttgcga cagagtctca ctgtcaccca      9540
ggctagagtg cagtggcgcc atctcggctc actgcaacct ccgcctcccg gtttaagcg       9600
attctcttgc ctcagcctcc cagtagctgg gattataggc gtgcgctacc acatctggct      9660
aatttttgta ttttagtag atggtttc accatgttgg ccaggcttgt ctcgaactcc        9720
tgacctcaga tgatccacct gcctcggcct cccaaagtgc tgggattaca ggcatgagcc      9780
accgtgccca gcctctacaa acttttatt ccattaacaa actatatgct gggatttaag      9840
ttttcttaat acttgatgga gtcctatgta attttcgagc ttttaatttt actaagacca     9900
ttttagttct gattatagaa gtaaattaac tttaaggat ttcaagttat atggcctact     9960
tctgaagcaa acttcttaca gtgaaaattc attataaggg tttagacctc cttatggaga     10020
cgttcaatct gtaaactcaa gagaaggcta caagtgcctc ctttaaactg ttttcatctc     10080
acaaggatgt tagtagaaag taaacagaag agtcatatct gttttcacag cccaattata     10140
cagaaatccg acagtactgc aatcactggc gaaattttgc tgacattgat gattcctgga     10200
aaagtataaa gagtatcttg gactggacat cttttaacca ggagagaatt gttgatgttg     10260
ctggaccagg gggttggaat gacccagata tggtaaaaac ttgagccctc cttgttcaag     10320
accctgcggt aggcttgttt cctattttga cattcaaggt aaatacaggt aaagttcctg     10380
ggaggaggct ttatgtgaga gtacttagag caggatgctg tggaaagtgg tttctccata     10440
tgggtcatct aggtaacttt aagaatgttt cctcctctct tgtttgaatt atttcattct     10500
ttttctcagt tagtgattgg caactttggc ctcagctgga atcagcaagt aactcagatg     10560
gccctctggg ctatcatggc tgctcccttta ttcatgtcta atgacctccg acacatcagc     10620
cctcaagcca aagctctcct tcaggataag gacgtaattg ccatcaatca ggaccccttg     10680
ggcaagcaag ggtaccagct tagacaggta aataagagta tatattttaa gatggcttta     10740
tatcccaat accaactttg tcttgggcct aaatctattt ttttcccttg ctcttgatgt      10800
tactatcagt aataaagctt cttgctagaa acattacttt atttccaaaa taatgctaca     10860
ggatcatttt aatttttcct acaagtgctt gatagttctg acattaagaa tgaatgccaa     10920
actaacaggg ccacttatca ctagttgcta agcaaccaca cttctttggt tttcaggga     10980
gacaactttg aagtgtggga acgacctctc tcaggcttag cctgggctgt agctatgata     11040
aaccggcagg agattggtgg acctcgctct tataccatcg cagttgcttc cctgggtaaa     11100
ggagtggcct gtaatcctgc ctgcttcatc acacagctcc tccctgtgaa aaggaagcta     11160
gggttctatg aatggacttc aaggttaaga agtcacataa atcccacagg cactgttttg     11220
cttcagctag aaatacaat gcagatgtca ttaaaagact tactttaaaa tgtttattt     11280
attgccaact actacttcct gtccacccttt ttctccattc actttaaaag ctcaaggcta     11340
ggtggctcat gcctgtaatc ccagcacttt gggaggctga ggcgggcaga tcacctgagg     11400
tcgggacttt gagaccccgcc tggacaacat ggtgaaaccc catttctaat aaaaatataa     11460
aaattagcca ggtgtggtgg cgcacctgtg gtcccagcta ctctggggc tgaggcatga     11520
gaatcgcttg aacccgggag tggaggttgc attgagctga gatcatgcca cctcactcca     11580
```

```
gcctgggcaa caaagattcc atctcaaaaa aaaaaaaaaa gccaggcaca gtggctcatg    11640
cctggaatcc cagcactttt ggaagctgag gcaggcagat cacttgaggt taggatttca    11700
agaccagcct ggctaacata gtaaagccct gtctctacta aaatacaaaa aattagccag    11760
gtatggtggc gagcttctgt agccccagct actcaggaga ctgaggcagg agaatcactt    11820
gaacccggga agtgggggggg tgcagtgacc caagatcacg ccactgcatt ccagcctggg    11880
caacagagca agactccatc tcaaaaaaaa aagttctatt tccttgaata aaattttccg    11940
aagtttaaac tttaggaata aaactattaa acccgtattt actcatccag atacccaccc    12000
cccttgttga gattctctcc caattatcaa aatgtgtagc atatttaact accaagagct    12060
aaacatcatt aagactgaaa tgtattaaga aggatgtata ggccaggcac ggtgtctcac    12120
gcctgtaatc ccaacacttt gggaggccaa gtcgggcgga tcacgaggtc aggagatgga    12180
gaccatcctg gccaacatgg tgaaaccccc tctctactaa aaatacaaaa attagccagg    12240
caggtggcag gcacctgtaa tcccagctac tccagaggct gaggcaggac aatcacttga    12300
acctgggagg cagaggctgc agtgagctga ggttgtacca attgcactcc agcctaggta    12360
acgagcaaca ctccatctca aaaaagaaa aaaaaaaga tgtataattt ggaactgtta    12420
agaggcattt taaaga                                                    12436
```

<210> SEQ ID NO 2
<211> LENGTH: 429
<212> TYPE: PRT
<213> ORGANISM: Homo sapiens

<400> SEQUENCE: 2

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
```

```
                   210             215             220
His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
                260                 265                 270

Phe Gly Leu Ser Trp Asn Gln Gln Val Thr Gln Met Ala Leu Trp Ala
                275                 280                 285

Ile Met Ala Ala Pro Leu Phe Met Ser Asn Asp Leu Arg His Ile Ser
                290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
                340                 345                 350

Met Ile Asn Arg Gln Glu Ile Gly Gly Pro Arg Ser Tyr Thr Ile Ala
                355                 360                 365

Val Ala Ser Leu Gly Lys Gly Val Ala Cys Asn Pro Ala Cys Phe Ile
                370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
                420                 425
```